(12) United States Patent
del Pozo Losada et al.

(10) Patent No.: US 7,521,478 B2
(45) Date of Patent: Apr. 21, 2009

(54) TOTAL SYNTHESIS OF MYRIAPORONES

(75) Inventors: Carlos del Pozo Losada, Madrid (ES); Andres Francesch, Madrdid (ES); Carmen Cuevas Marchante, Madrid (ES); Marta Perez Alvarez, Madrid (ES)

(73) Assignee: Pharma Mar, S.A.U., Madrid (ES)

( * ) Notice: Subject to any disclaimer, the term of this patent is extended or adjusted under 35 U.S.C. 154(b) by 329 days.

(21) Appl. No.: 10/523,172

(22) PCT Filed: Jul. 30, 2003

(86) PCT No.: PCT/GB03/03327

§ 371 (c)(1),
(2), (4) Date: Sep. 1, 2005

(87) PCT Pub. No.: WO2004/011458

PCT Pub. Date: Feb. 5, 2004

(65) Prior Publication Data

US 2006/0084819 A1 Apr. 20, 2006
US 2008/0103320 A2 May 1, 2008
US 2008/0269511 A2 Oct. 30, 2008

(30) Foreign Application Priority Data

Jul. 30, 2002 (GB) .................................. 0217638.6

(51) Int. Cl.
*A61K 31/336* (2006.01)
*C07D 301/27* (2006.01)
*C07D 303/12* (2006.01)

(52) U.S. Cl. .......................... 514/475; 549/541; 549/554

(58) Field of Classification Search .................. 514/475; 548/541, 554
See application file for complete search history.

(56) References Cited

U.S. PATENT DOCUMENTS 5,514,708 A 5/1996 Rinehart et al. ............. 514/460

OTHER PUBLICATIONS

Taylor et al, "Divergent Approach to the Myriaporones and Tedanolide: Enantioselective Preparation of the Common Intermediate" Tetrahedron Letters, vol. 39, No. 51, pp. 9361-9364, Dec. 17, 1998.
Rousch et al, "Studies on the Synthesis of Tedanolide: Synthesis of the C(5)-C(21) Segment via a Highly Stereoselective Fragment Assembly Aldol Reaction of a Chiral β,γ-Unsaturated Methyl Ketone" Organic Letters, vol. 1, No. 1, pp. 95-98, 1999.
Taylor et al, "Zirconium-mediated allylations: A diastereoselective approach to the myriaporones" Abstracts of Papers, 218th National Meeting of the American Chemical Society, vol. 218, No. 1-2, p. ORGN 591, Aug. 1999.

Taylor et al, "Synthetic Efforts toward the total synthesis of myriaporone 1" Abstracts of Papers, 218th National Meeting of the American Chemical Society, vol. 218, No. 1-2, p. ORGN 621, Aug. 1999.
Zheng et al, "Studies on the synthesis of myriaporones: stereoselective synthesis of the C5-C13 fragment starting from D-glucose via regioselective reductive opening of methoxybenzylidene acetal" Chemical & Pharmaceutical Bulletin, vol. 48, No. 11, pp. 1761-1765, Nov. 2000.
Moss, G.P., "Basic Terminology of Stereochemistry (IUPAC Recommendations 1996), " Pure & Appl. Chem., vol. 68, No. 12, pp. 2193-2222, 1996.
Rinehart, "The 1994 Japan-U.S Seminar on bioorganic marine chemistry, meeting report," *Journal of Natural Products*, vol. 58, No. 3, pp. 344-358, Mar. 1995.
Evans et al., "Total Synthesis of the Macrolide Antibiotic Cytovaricin," *Journal of American Chemical Society*, vol. 112, pp. 7001-7031, 1990.
Patani et al., "Bioisosterism: A Rational Approach in Drug Design," *Chemical Reviews*, vol. 96, pp. 3147-3176, 1996.
IUPAC Compendium of Chemical Terminology, "Alkylidene Groups," 2nd Edition, p. 1314, 1997.

*Primary Examiner*—Taofiq A Solola
(74) *Attorney, Agent, or Firm*—Kenneth H. Sonnenfeld; Michael A. Willis; King & Spalding, LLP

(57) ABSTRACT

Compounds of the general formula (I) or a pharmaceutically acceptable salt, derivative, prodrug or stereoisomer thereof are provided: wherein the substituent groups defined by R are each independently selected from the group consisting of H, SiR'$_3$, SOR', SO$_2$X, C(=O)R', C(=O)OR', C(=O)NR', substituted or unsubstituted alkyl, substituted or unsubstituted alkenyl, substituted or unsubstituted alkynyl, aryl, heteroaryl or aralkyl; the group R' is selected from substituted or unsubstituted alkyl, substituted or unsubstituted alkenyl, substituted or unsubstituted alkynyl, aminoalkyl, aryl, aralkyl and heterocyclic groups; and the group R" is selected from the group consisting of H, OH, OR', OCOR', SH, SR', SOR', SO$_2$R', NO$_2$, NH$_2$, NHR', N(R')$_2$, NHCOR', N(COR')$_2$, NHSO$_2$R', CN, halogen, C(=O)H, C(=O)R', CO$_2$H, CO$_2$R', CH$_2$OR, substituted or unsubstituted alkyl, substituted or unsubstituted haloalkyl, substituted or unsubstituted alkenyl, substituted or unsubstituted alkylidene, substituted or unsubstituted alkynyl, substituted or unsubstituted aryl, substituted or unsubstituted aralkyl and substituted or unsubstituted heteroaromatic; with the proviso that the compound is not compound 1, 3 or 4 of U.S. Pat. No. 5,514,708. The compounds have antitumour activity. A synthetic route is also provided.

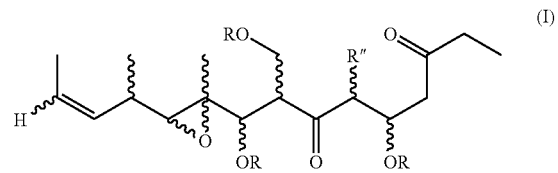

(I)

34 Claims, No Drawings

TOTAL SYNTHESIS OF MYRIAPORONES

BACKGROUND OF THE INVENTION

Myriaporones are a new class of marine polyketide-derived isolated from the bryozoan *Myriapora truncata*.

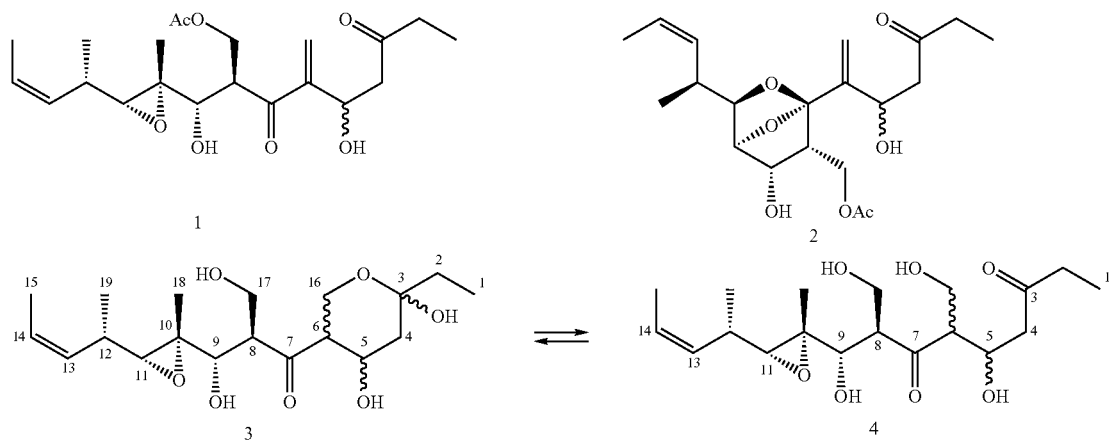

Myriaporones are disclosed to have antitumor activity. The complete structure for these related compounds was given by K. L. Rinehart et al., *J. Nat. Prod.* 1995, 58, 344 and U.S. Pat. No. 5,514,708. Myriaporones 3 and 4 described there are in an equilibrium mixture between the free hydroxy ketone and the hemiketal as indicated in the figure above.

There have been several unsuccessful attempts at the synthesis of myriaporones, see for example Taylor, R. E.; Ciavarri, J. C.; Hearn, B. R. "A Divergent Approach the Myriaporones and Tedanolide: Enantioselective Preparation of the Common Intermediate" *Tetrahedron Lett.* 1998, 39, 9361; Taylor et al., *Org. Lett.* 2002, 4, 2853, available on the Web 2 Aug. 2002.

In view of their interesting biological properties there is a need to provide an efficient, stereocontrolled total synthesis of myriaporones and related compounds.

SUMMARY OF THE INVENTION

In a first aspect, the present invention is directed to compounds of general formula I or a pharmaceutically acceptable salt, derivative, prodrug or stereoisomer thereof

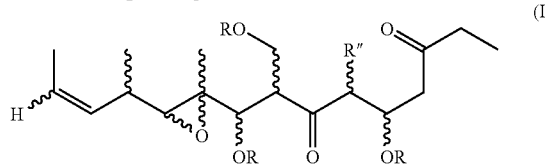

(I)

wherein the substituent groups defined by R are each independently selected from the group consisting of H, SiR'$_3$, SOR', SO$_2$R', C(=O)R', C(=O)OR', C(=O)NR', substituted or unsubstituted alkyl, substituted or unsubstituted alkenyl, substituted or unsubstituted alkynyl, aryl, heteroaryl or aralkyl;

the group R' is selected from substituted or unsubstituted alkyl, substituted or unsubstituted alkenyl, substituted or unsubstituted alkynyl, aminoalkyl, aryl, aralkyl and heterocyclic groups; and the group R" is selected from the group consisting of H, OH, OR', OCOR', SH, SR', SOR', SO$_2$R', NO$_2$, NH$_2$, NHR', N(R')$_2$, NHCOR', N(COR')$_2$, NHSO$_2$R', CN, halogen, C(=O)H, C(=O)R', CO$_2$H, CO$_2$R', CH$_2$OR, substituted or unsubstituted alkyl, substituted or unsubstituted haloalkyl, substituted or unsubstituted alkenyl, substituted or unsubstituted alkylidene, substituted or unsubstituted alkynyl, substituted or unsubstituted aryl, substituted or unsubstituted aralkyl and substituted or unsubstituted heteroaromatic;

with the proviso that the compound is not compound 1, 3 or 4 of U.S. Pat. No. 5,514,708.

Compound 1 of U.S. Pat. No. 5,514,708 corresponds to formula 1 shown above in the description of the prior art.

According to our findings, the natural compounds 3 and 4 of U.S. Pat. No. 5,514,708 correspond to compounds 4a and 3a as described in the examples below.

When R" is CH$_2$OH compounds of formula I may exist as a mixture of the ketone isomer and the hemiketal isomer (5),

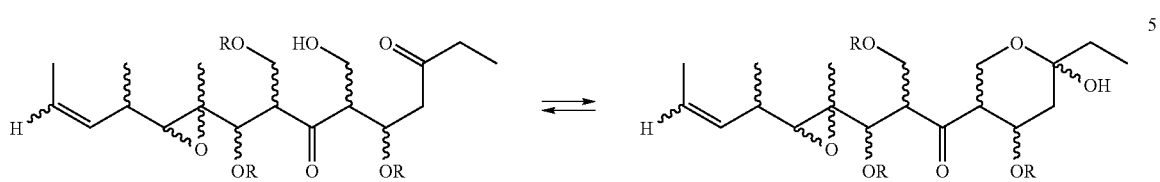

wherein the substituent groups defined by R are as defined above.

In particular, we prefer that at least one of the R substituents is not hydrogen. We have found that these compounds show improved cytotoxicity.

Myriaporones are obtained from natural sources. Another objective of the present invention is to provide a synthetic route to produce myriaporones and derivatives. Therefore, the present invention is directed to the synthesis of the compounds of formula I as defined above, including those where all R groups are H, and to intermediates used in the synthetic process.

According to the present invention, a process of this invention involves removing a protecting group from a compound of formula 5a wherein at least one group R is a protecting group to give the corresponding compound of formula 5b where the said at least one group R is hydrogen. This synthetic route can be applied to new and known myriaporones.

Another embodiment of the present invention is a pharmaceutical composition comprising a compound of formula I or a pharmaceutically acceptable salt, derivative, prodrug or stereoisomer thereof or an intermediate of their synthesis and a pharmaceutically acceptable carrier.

Another embodiment of the present invention is the use of compounds of formula I or pharmaceutically acceptable salts, derivatives, prodrugs or stereoisomers thereof as antitumor agents.

DETAILED DESCRIPTION OF THE INVENTION

The present invention relates to compounds of formula I as defined above.

In these compounds the substituents can be selected in accordance with the following guidance:

Alkyl groups preferably have from 1 to 12 carbon atoms. One more preferred class of alkyl groups has 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 2, 3 or 4 carbon atoms. The terms alkenyl and alkynyl as used herein refer to both cyclic and noncyclic groups, although straight or branched noncyclic groups are generally more preferred.

Alkylidene groups may be branched or unbranched and preferably have from 1 to 12 carbon atoms. One more preferred class of alkylidene groups has from 1 to about 8 carbon atoms, yet more preferably from 1 to about 6 carbon atoms, and most preferably 1, 2, 3 or 4 carbon atoms. Methylidene, ethylidene and propylidene including isopropylidene are particularly preferred alkylidene groups in the compounds of the present invention Preferred alkylsulfinyl groups in the compounds of the present invention include those groups having one or more sulfoxide (SO) groups and from 1 to about 12 carbon atoms, more preferably from 1 to about 8. carbon atoms, and still more preferably 1 to about 6 carbon atoms. Alkylsulfinyl groups having 1, 2, 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about. 8 carbon atoms, and still more preferably 1 to about 6 carbon atoms. Alkylsulfonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable heterocyclic groups include heteroaromatic and heteroalicyclic groups. Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Specifically preferred aryl groups include substituted or unsubstituted phenyl, naphthyl, biphenyl, phenanthryl, and anthracyl.

References herein to substituted groups in the compounds of the present invention refer to the specified moiety, typically alkyl or alkenyl, that may be substituted at one or more available positions by one or more suitable groups, e.g., halogen such as fluoro, chloro, bromo and iodo; cyano; hydroxyl; nitro; azido; carboxamido; alkyl groups including those groups having 1 to about 12 carbon atoms, preferably from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms, preferably from 1 to about 6 carbon atoms; aryloxy such as phenoxy, alkylthio groups including those moieties having one or more thioether linkages and from 1 to about 12 carbon atoms, preferably from 1 to about 6 carbon atoms; alkylsulfinyl groups including those moieties having one or more sulfinyl linkages and from 1 to about 12 carbon atoms, preferably from 1 to about 6 carbon atoms; alkylsulfonyl groups including those moieties having one or more sulfonyl linkages and from 1 to about 12 carbon atoms, preferably from 1 to about 6 carbon atoms; aminoalkyl groups such as groups having one or more N atoms and from 1 to about 12 carbon atoms, preferably from 1 to about 6 carbon atoms; aryl having 6 or more carbons, particularly phenyl; aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteroatoms or with 10 ring atoms and 1 to 3 heteroatoms.

Preferred R groups include alkyl, alkenyl and alkynyl that may be substituted at one or more available positions by one or more suitable groups, e.g., halogen such as fluoro, chloro, bromo and iodo, especially ω-chloro or perfluoro; aminoalkyl groups such as groups having one or more N atoms and from 1 to about 12 carbon atoms, preferably from 1 to about 6 carbon atoms; aryl having 6 or more carbons, particularly phenyl; aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteroatoms or with 10 ring atoms and 1 to 3 heteroatoms, the heterocyclic groups optionally being substituted with one or more of the substituents, especially amino such as dimethylamino or with keto.

The term "pharmaceutically acceptable salts, derivatives, prodrugs" refers to any pharmaceutically acceptable salt, ester, solvate, hydrate or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in crystalline form either as free compounds or as solvates (e.g. hydrates) and it is intended that both forms are within the scope of the present invention. Methods of solvation are generally known within the art.

Any compound that is a prodrug of a compound of formula I is within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester derivative.

The compounds of the present invention represented by the above described formula I may include enantiomers depending on their asymmetry or diastereoisomers. The single isomers and mixtures of the isomers fall within the scope of the present invention.

In one aspect, the present invention extends to compounds of formula I which differ from the known myriaporones in respect of one or more positions of stereochemistry. Thus, in this aspect, the compounds are isomers and isomeric derivatives.

The preferred stereochemistry of compounds of formula I is the following:

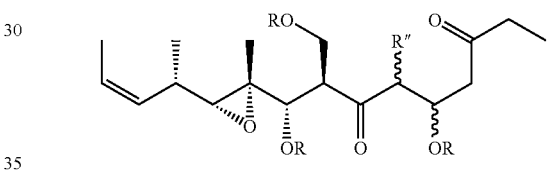

When R" is CH$_2$OH the preferred stereochemistry of compounds of formula 5 is:

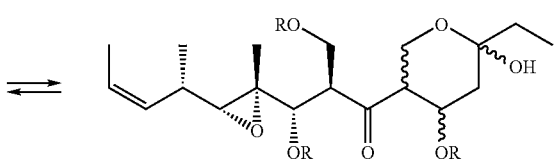

Particularly preferred are compounds having the following stereochemistry:

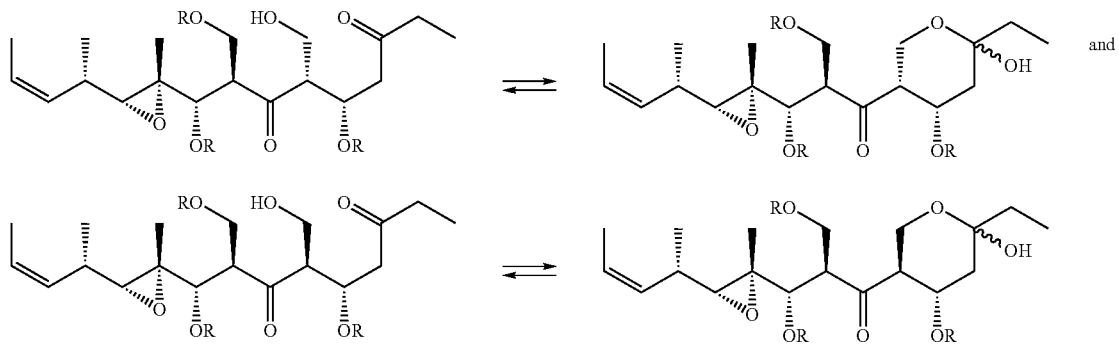

We have found that these particular groups of compounds show improved biological properties.

In another preferred embodiment of the present invention, R″ is a substituted or unsubstituted alkylidene.

In one preferred embodiment of the compounds of formula 5, at least one of the R substituents is C(=O)R′. Particularly preferred is the compound of formula 47:

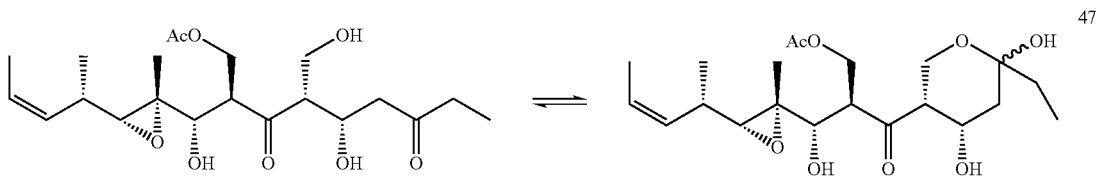

In another embodiment of the compounds of formula I or of formula 5, at least one of the R substituents is not hydrogen. Suitably, each group that is not hydrogen is a protecting group, which may be the same or different.

Compounds of the following formula are preferred:

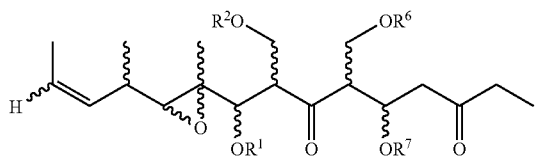

where $R^1$, $R^2$, $R^6$ and $R^7$ are hydroxy protecting groups.

Particularly preferred are compounds of formula 19:

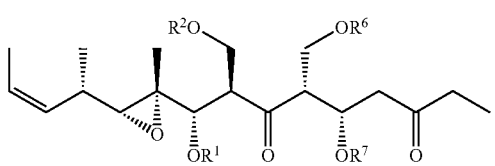

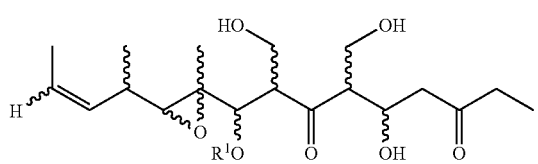

where $R^1$, $R^2$, $R^6$ and $R^7$ are hydroxy protecting groups; and of formula 30:

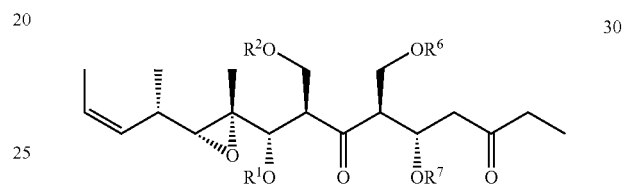

where $R^1$, $R^2$, $R^6$ and $R^7$ are hydroxy protecting groups.

Suitably, $R^1$, $R^2$, $R^6$ and $R^7$ are the same protecting group. They can be chosen from TBS (tBuMe$_2$Si—), TBDPS (tBuPh$_2$Si—), TES (Et$_3$Si—), MOM (CH$_3$OCH$_2$—), MEM (CH$_3$OCH$_2$CH$_2$OCH$_2$—), SEM ((CH$_3$)$_3$SiCH$_2$CH$_2$OCH$_2$—) and Ac—(CH$_3$CO—). Especially preferred is TBS (tBuMe$_2$Si—) or TBDPS (tBuPh$_2$Si—).

Also preferred are compounds of the following formula:

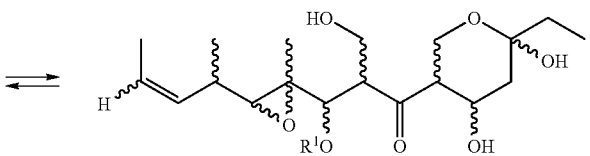

where $R^1$ is a hydroxy protecting group.

Particularly preferred are compounds of formula 20 and 31:

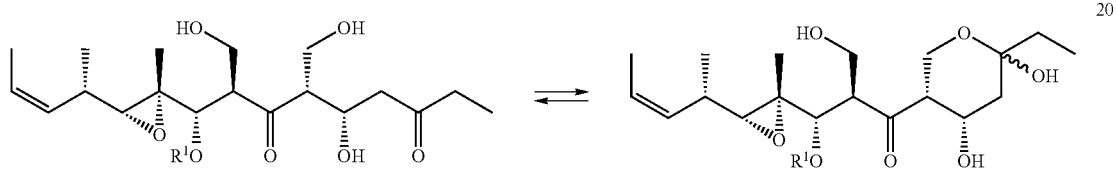

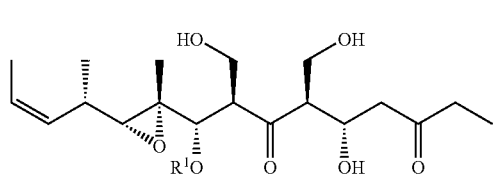 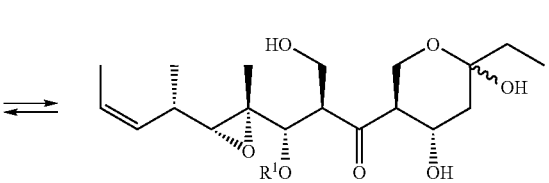

In the above compounds, $R^1$ is suitably TBS (tBuMe$_2$Si—).

The present invention also provides a process for synthesis of a myriaporone compound of formula 5:

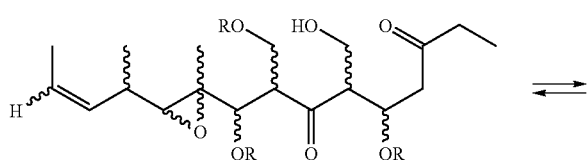

which may exist as a mixture of the ketone isomer and the hemiketal isomer, or as one of the two isomeric forms;

wherein the substituent groups defined by R are each independently selected from the group consisting of H, SiR'$_3$, SOR', SO$_2$R', C(=O)R', C(=O)OR', C(=O)NR', substituted or unsubstituted alkyl, substituted or unsubstituted alkenyl, substituted or unsubstituted alkynyl, aryl, heteroaryl or aralkyl, and wherein at least one group R is hydrogen;

and wherein the group R' is selected from substituted or unsubstituted alkyl, substituted or unsubstituted alkenyl, substituted or unsubstituted alkynyl, aminoalkyl, aryl, aralkyl and heterocyclic groups;

which comprises removing a protecting group from an intermediate compound of formula:

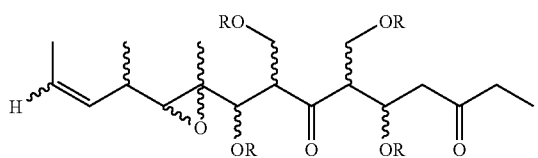

wherein the substituent groups defined by R are each independently selected from the group consisting of H, SiR'$_3$, SOR', SO$_2$R', C(=O)R', C(=O)OR', C(=O)NR', substituted or unsubstituted alkyl, substituted or unsubstituted alkenyl, substituted or unsubstituted alkynyl, aryl, heteroaryl or aralkyl, and wherein the or each group R to become hydrogen in the compound 5 is in the intermediate compound protecting group;

and wherein the group R' is as defined.

Suitably, more than one group R in the intermediate compound is a protecting group.

A process of this invention can comprise removing at least one protecting group from a compound of formula 19:

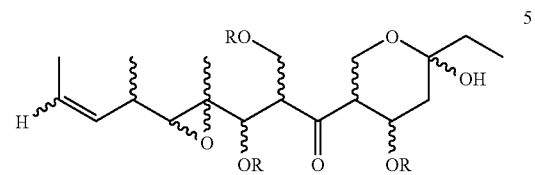

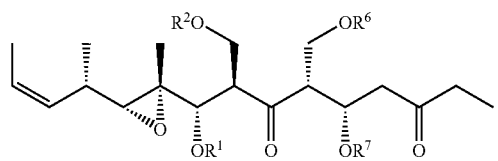

where $R^1$, $R^2$, $R^6$ and $R^7$ are hydroxy protecting groups.

A related process of this invention can comprise removing at least one protecting group from a compound of formula 30:

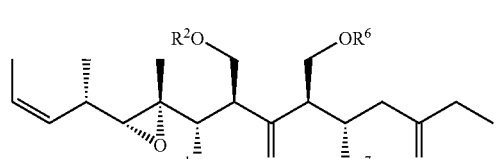

where $R^1$, $R^2$, $R^6$ and $R^7$ are hydroxy protecting groups.

Suitably $R^1$, $R^2$, $R^6$ and $R^7$ are the same protecting group and are removed.

Another process of this invention comprises removing a protecting group from a compound of formula 20:

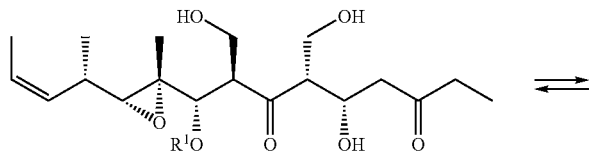

where $R^1$ is a hydroxy protecting group.

A related process comprises removing a protecting group from a compound of formula 31:

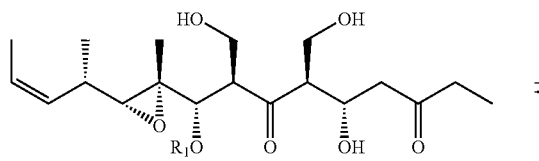

where $R^1$ is a hydroxy protecting group.

The invention further provides a process for synthesis of a myriaporone compound of formula I:

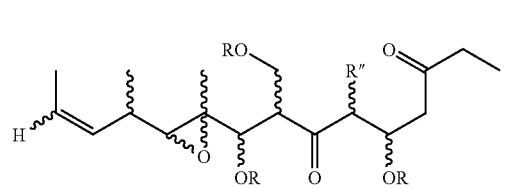

wherein the substituent groups R and R″ are as defined above for the formula I; which comprises derivatisation of a compound of formula 5:

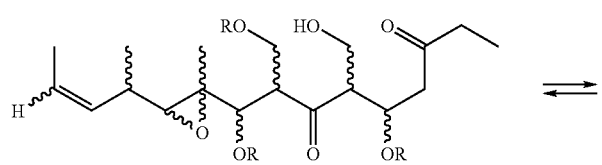

which may exist as a mixture of the ketone isomer and the hemiketal isomer, or as one of the two isomeric forms; and wherein the substituent groups are as defined in claim 25.

The invention further provides compounds of the following formula

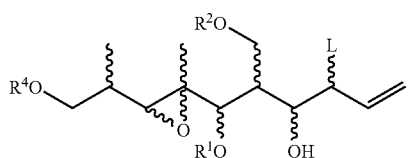

where $R^1$, $R^2$ and $R^4$ are hydroxy protecting groups, and L is a stereospecific leaving group which induces chirality.

Preferred are compounds of formula 10 and 22:

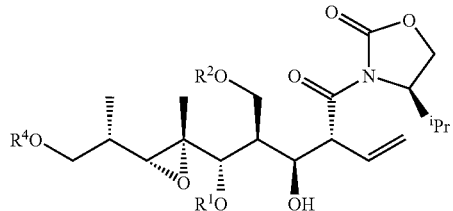

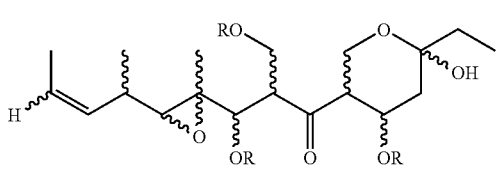

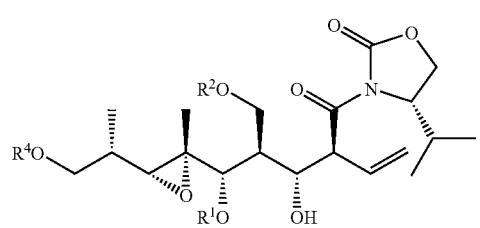

The invention also provides compounds of the following formula:

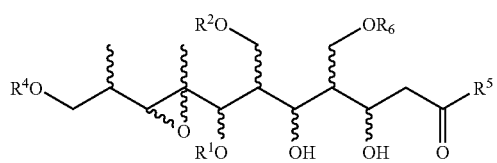

5 wherein $R^1$, $R^2$, $R^4$ and $R^6$ are hydroxy protecting groups;
$R^5$ is selected from the group consisting of H, SOR', $SO_2R'$, C(=O)R', C(=O)OR', C(=O)NR', substituted or unsubstituted alkyl, substituted or unsubstituted alkenyl, substituted or unsubstituted alkynyl, aryl, heteroaryl or aralkyl;
and R' has the same meaning as defined in claim 1.

Preferred are compounds of formula 14 and 26:

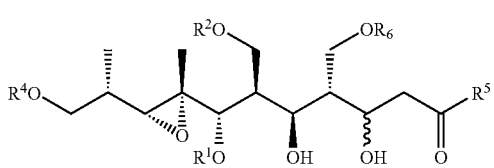

14

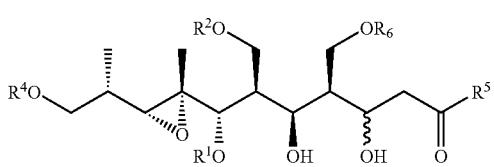

26

The invention also provides a process for preparation of a compound of formula 14 which comprises chain extension of a compound of formula 13; a process for preparation of a compound of formula 26 which comprises chain extension of a compound of formula 25; a process for preparation of a compound of formula 19 which comprises chain extension of a compound of formula 18; and a process for preparation of a compound of formula 30 which comprises chain extension of a compound of formula 29.

The invention also provides compounds of the following formula:

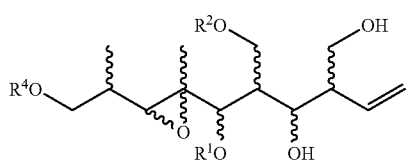

wherein $R^1$, $R^2$ and $R^4$ are hydroxy protecting groups.

Preferred are compounds of formula 11 and 23:

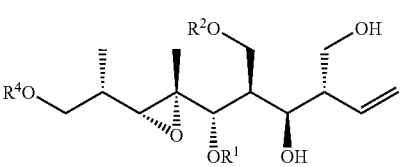

11

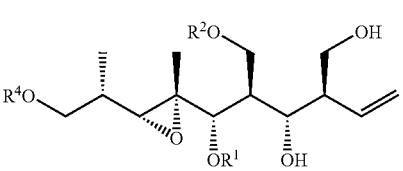

23

The invention also provides compounds of the following formula:

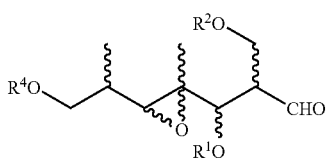

wherein $R^1$, $R^2$ and $R^4$ are hydroxy protecting groups.

Compounds of formula 8 are preferred:

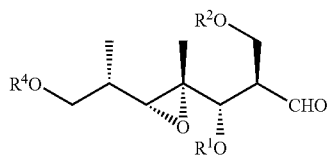

8

The compounds of the present invention can be synthetically prepared from the intermediate compound 6 described by W. R. Roush et al., *Org. Lett.* 1999, 1, 95 or its stereoisomers.

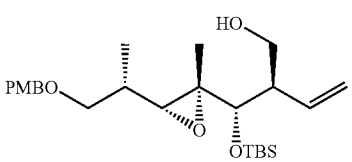

6

A method of producing compounds of formula I is shown in the Scheme 1.

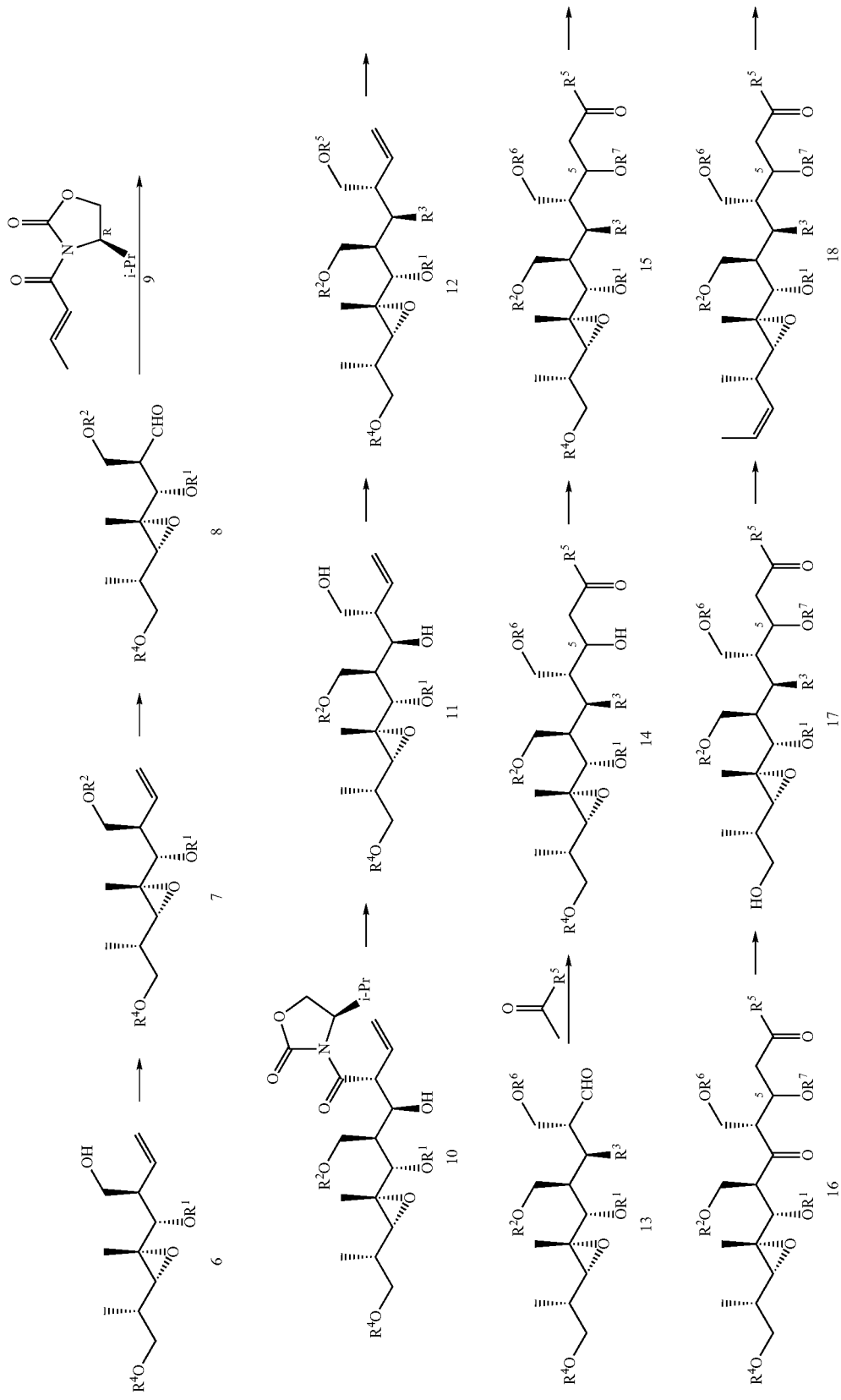

-continued
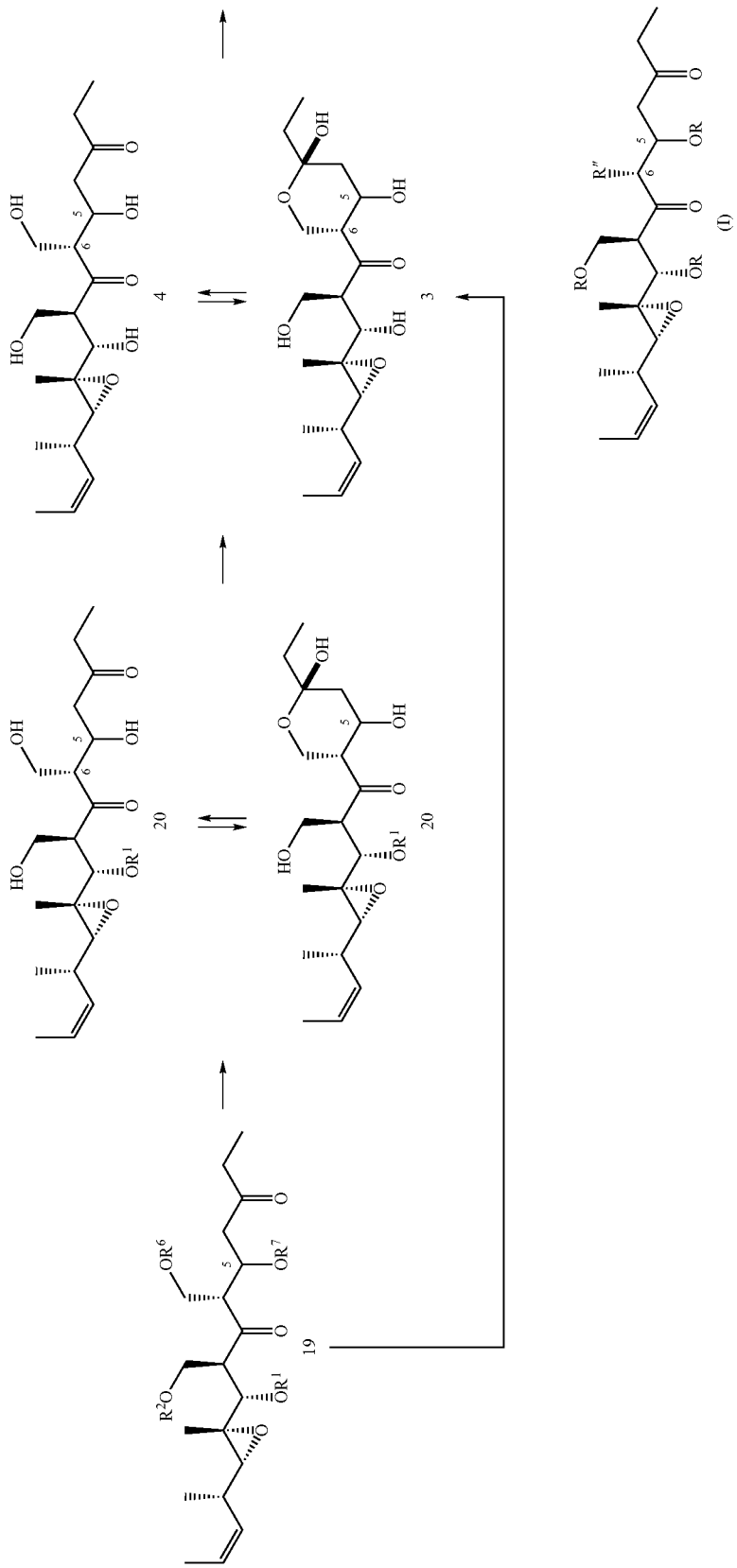

For the purpose of discussing this scheme, the carbons in each respective molecule are assigned with the appropriate number to their final position at the end product of formula I, using the numbering system given previously for the known compound 3/4. The scheme 1 involves:

protecting the compound 6 to give protected compound 7. This protection is carried out with the related reagent of the selected protecting group (such as TBSCl, TESOTf, MOMBr or tBu$_2$Si(OTf)$_2$) in the conditions according to known procedures in organic synthesis (for example: Imidazole, DIPEA or 2,6-lutidine in DMF or CH$_2$Cl$_2$), alternative protecting groups are also contemplated, converting the terminal vinyl group at carbons 6 and 7 to an aldehyde in compound 8. This conversion is carried out by ozonolysis of the vinyl group (for example with O$_3$, in CH$_2$Cl$_2$ at −78° C.) or by formation of the corresponding dihydroxy derivative (for example with NMO, OsO$_4$ in THF:H$_2$O) and the diol is cleavaged (for example with NaIO$_4$ in THF:H$_2$O) to the corresponding aldehyde, reaction with an oxazolidinone 9 to give compound 10. The oxazolidinone 9 is converted into the corresponding enolate (for example with Bu$_2$BOTf and Et$_3$N in CH$_2$Cl$_2$ at −78° C.) and added to 8 at low temperature (−30° C.) to give 10. Other stereospecific leaving groups which induce the desired chirality are also contemplated within the scope of protection of the invention.

reduction of compound 10 to obtain a 17-hydroxymethyl sidechain in the compound 11. This reduction is carried out with the corresponding reagent (such as LiBH$_4$) in the conditions (for example in THF:H$_2$O or CH$_2$Cl$_2$) according to known procedures in organic synthesis, although other reducing agents are also contemplated within the scope of protection of the invention.

further protection at the 17-hydroxy group to give compound 12. This protection is carried out with the related reagent of the selected protecting group (such as TBSCl, TESCl, MEMCl or SMCl) in the conditions according with known procedures in organic synthesis (for example: imidazole, DIPEA, DMAP or Et$_3$N in DMF or CH$_2$Cl$_2$), other protecting groups are also contemplated in the invention, converting the terminal vinyl group at carbons 4 and 5 to an aldehyde in compound 13. This conversion is carried out by ozonolysis of the vinyl group (for example O$_3$, in CH$_2$Cl$_2$ at −78° C.) or by formation of the corresponding dihydroxy derivative (for example NMO, OsO$_4$ in THF:H$_2$O) and the diol was cleavaged (for example NaIO$_4$ in THF:H$_2$O or Pb(OAc)$_4$ in toluene) to the corresponding aldehyde, chain extension at carbon 5 to give compound 14. In the illustrated example, the selected reagent (CH$_3$C(O)N(CH$_3$)OCH$_3$) is converted into the corresponding enolate ([(CH$_3$)$_3$Si]$_2$NLi in THF at −78° C.) and added to 13 at low temperature (−78° C.) to give 14, alternative procedures for chain extension known to the person skilled in the art can also be used to achieve the same purpose, further protection at the 5-hydroxy group to give compound 15. This protection is carried out with the related reagent of the selected protecting group (such as TBSOTf) in the conditions (2,6-lutidine in CH$_2$Cl$_2$) according to known procedures. Alternative protecting groups can also be used, oxidation of the hydroxy group at carbon 7 to afford compound 16. This oxidation is carried out with the corresponding reagent (such as Dess-Martin periodinane) in the conditions according with known procedures in organic synthesis (for example in CH$_2$Cl$_2$), deprotection at the 13-protected hydroxy group to give terminally deprotected compound 17. This deprotection is carried out with the related reagent (for example DDQ) for the selected protecting group (for example PMB) in the conditions according with known procedures (for example in CH$_2$Cl$_2$:H$_2$O), formation of a terminal olefin group by extension with carbons 14 and 15 to give compound 18. This transformation is performed in two steps: a) oxidation of the primary hydroxy group into the corresponding aldehyde with the selected reagent (for example Dess-Martin periodinane) and b) formation of the cis double bound through a Wittig or Horner-Wadsworth-Emmmons reaction in the standard conditions, alternative procedures for chain extension known to the person skilled in the art can also be used to achieve the same purpose, formation, if not already present, of the 7-keto substituent of compound 19. This oxidation is carried out with the corresponding reagent (such as Dess-Martin periodinane) in the conditions according with known procedures in organic synthesis (for example in CH$_2$Cl$_2$), chain extension with carbons 1 and 2 if not already present in compound 19. This extension is carried out with the corresponding reagent (such as BrMgEt) in the conditions according with known procedures in organic synthesis (for example in THF), partial or complete deprotection to a compound 20 or 4/3. This deprotection is carried out with the related reagent (such as TBAF and AcOH) for the selected protecting group (for example TBS) in the conditions according with known procedures (for example in CH$_2$Cl$_2$), and optional derivatisation to a derivative shown as compound (I), where at least one R is not hydrogen, for example by reaction with Ac$_2$O, an alkylcarboxylate chloride or anhydride in the presence of the corresponding base (for example Et$_3$N) in any suitable solvent such as CHCl$_3$.

Additionally, different isomericallyi synthetic myriaporones are prepared from the intermediate compound 8 by using a different stereospecific leaving group, for example by using (S)-oxazolidinone instead of (R)-oxazolidinone. The route for producing these compounds is depicted in Scheme 2.

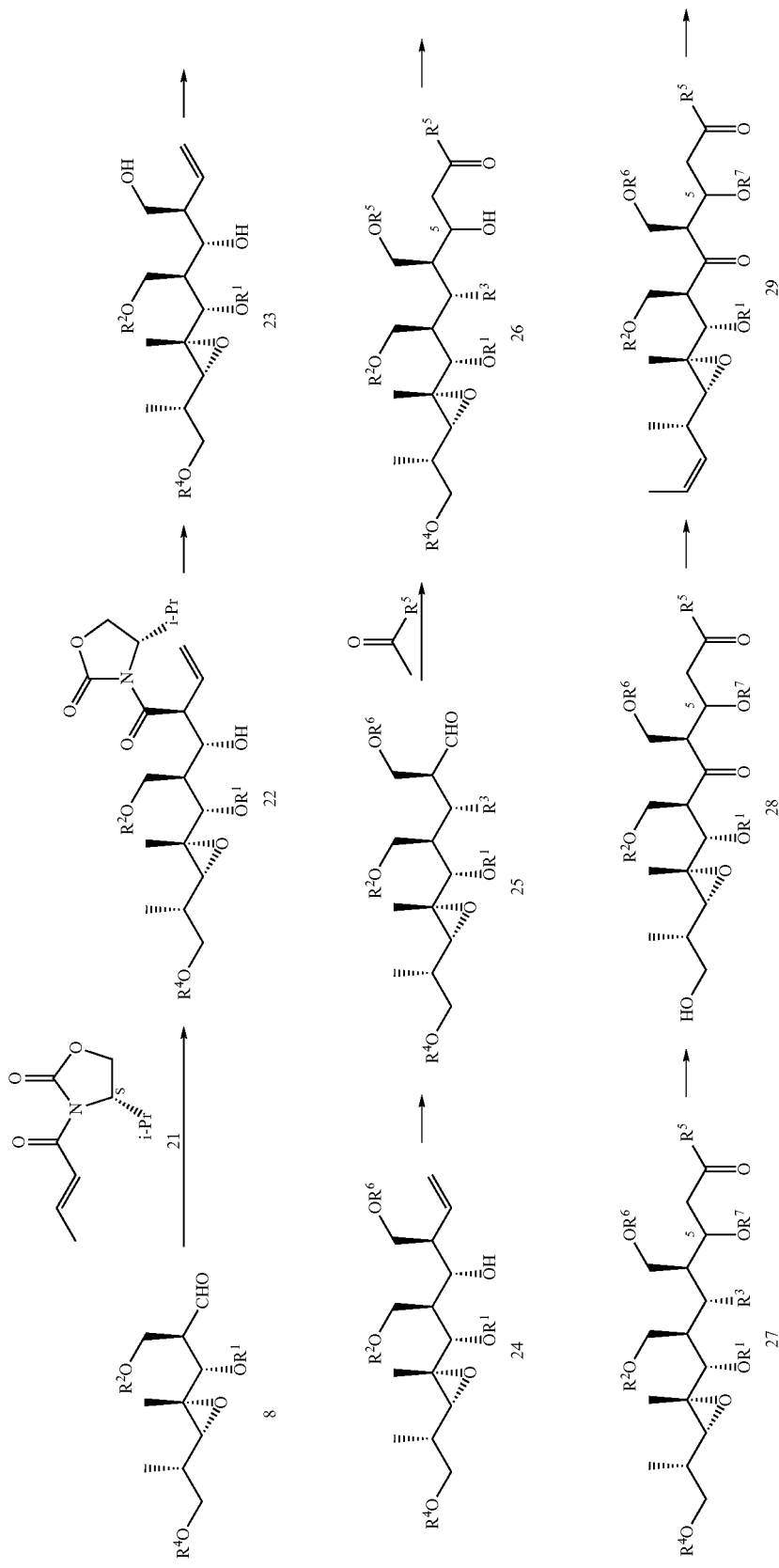

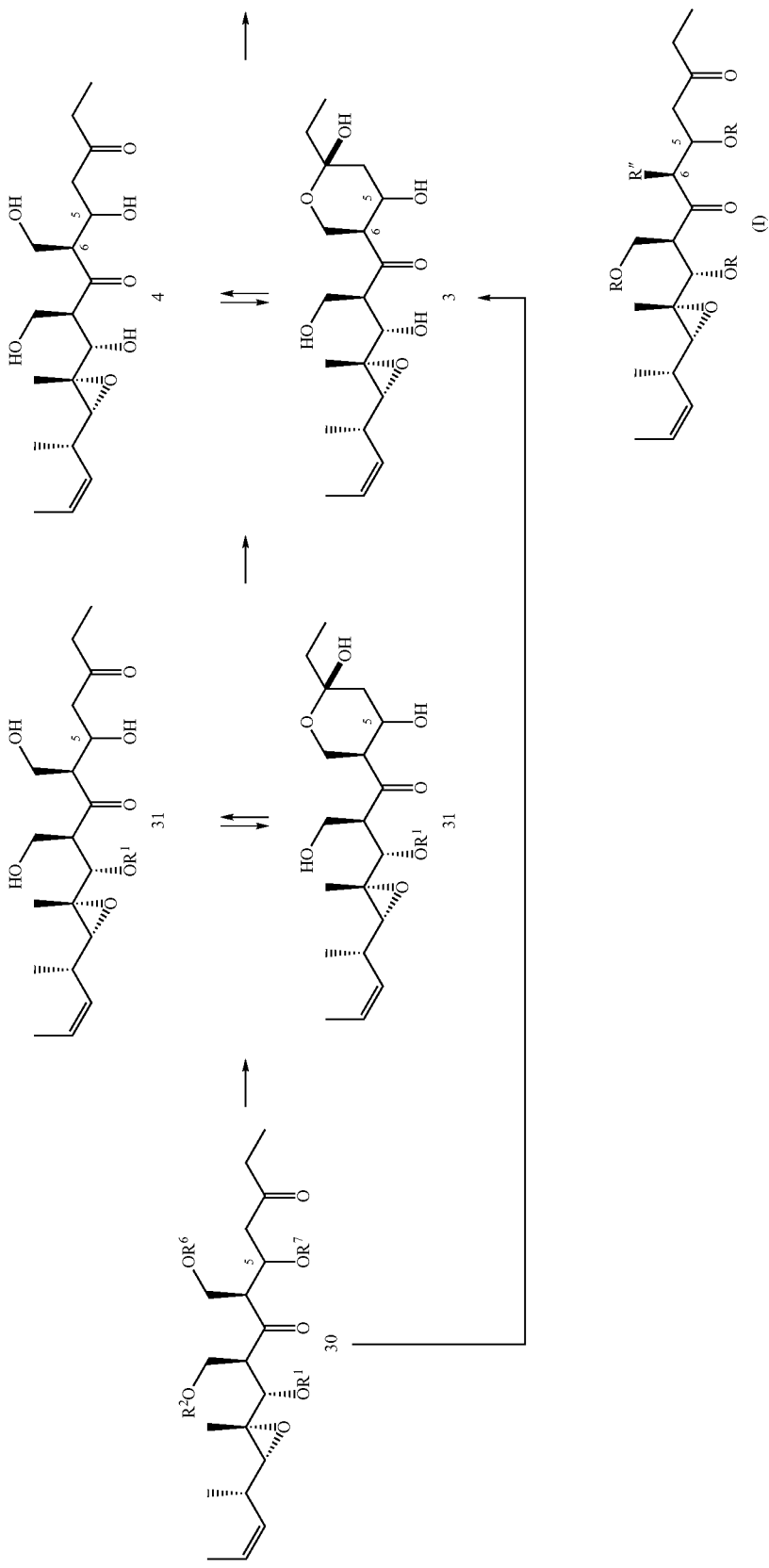

The reaction scheme 2 involves the same reactions as those of scheme I, with a different stereochemistry in the oxazolidinone 9.

A purpose of the invention is to provide a first total synthesis of myriaporones 3 and 4 and from these compounds or previous intermediates obtain other compounds of formula I. The synthesis should preferably make it possible to obtain the largest possible quantities of myriaporones 3 and 4 by simple ways and means. The synthesis should also allow the preparation of the largest possible number of specific derivatives of myriaporones 3 and 4. In addition, the synthesis should preferably proceed stereoselectively, so that four diastereoisomers of myriaporones 3 and 4 can be obtained in pure form. A further purpose of the invention is to provide the kind of total synthesis intermediates that will make the synthesis as flexible as possible and thus enable the preparation of a large number of derivatives.

In the previous reaction schemes, the hydroxy protecting groups $R^1$, $R^2$, $R^4$, $R^6$, and $R^7$ may be any of the examples of hydroxy protecting groups reported in "Protective Groups in Organic Synthesis", T. W. Greene, P. G. Wuts, Ed. Wiley-Interscience, 3$^{rd}$ Edition. Examples of hydroxy protecting groups are given in the following list:

| protection for —OH group | |
|---|---|
| | abbreviation |
| ethers | |
| methyl | |
| methoxymethyl | MOM |
| benzyloxymethyl | BOM |
| methoxyethoxymethyl | MEM |
| 2-(trimethylsilyl)ethoxymethyl | SEM |
| methylthiomethyl | MTM |
| phenylthiomethyl | PTM |
| azidomethyl | |
| cyanomethyl | |
| 2,2-dichloro-1,1-difluoroethyl | |
| 2-chloroethyl | |
| 2-bromoethyl | |
| tetrahydropyranyl | THP |
| 1-ethoxyethyl | EE |
| phenacyl | |
| 4-bromophenacyl | |
| cyclopropylmethyl | |
| allyl | |
| propargyl | |
| isopropyl | |
| cyclohexyl | |
| t-butyl | |
| benzyl | |
| 2,6-dimethylbenzyl | |
| 4-methoxybenzyl | MPM or PMB |
| o-nitrobenzyl | |
| 2,6-dichlorobenzyl | |
| 3,4-dichlorobenzyl | |
| 4-(dimethylamino)carbonylbenzyl | |
| 4-methylsufinylbenzyl | Msib |
| 9-anthrylmethyl | |
| 4-picolyl | |
| heptafluoro-p-tolyl | |
| tetrafluoro-4-pyridyl | |
| trimethylsilyl | TMS |
| t-butyldimethylsilyl | TBDMS |
| t-butyldiphenylsilyl | TBDPS |
| triisopropylsilyl | TIPS |
| esters | |
| aryl formate | |
| aryl acetate | |

| -continued | |
|---|---|
| protection for —OH group | |
| | abbreviation |
| aryl levulinate | |
| aryl pivaloate | ArOPv |
| aryl benzoate | |
| aryl 9-fluorocarboxylate | |
| aryl methyl carbonate | |
| 1-adamantyl carbonate | |
| t-butyl carbonate | BOC-OAr |
| 4-methylsulfinylbenzyl carbonate | Msz-Oar |
| 2,4-dimethylpent-3-yl carbonate | Doc-Oar |
| aryl 2,2,2-trichloroethyl carbonate | |
| aryl vinyl carbonate | |
| aryl benzyl carbonate | |
| aryl carbamate | |
| dimethylphosphinyl | Dmp-OAr |
| dimethylphosphinothioyl | Mpt-OAr |
| diphenylphosphinothioyl | Dpt-Oar |
| aryl methanesulfonate | |
| aryl toluenesulfonate | |
| aryl 2-formylbenzenesulfonate | |

Preferred $R^2$, $R^4$, $R^6$ and $R^7$ are TBS (tBuMe$_2$Si—), TBDPS (tBuPh$_2$Si—), TES (Et$_3$Si—), MOM (CH$_3$OCH$_2$—), MEM (CH$_3$OCH$_2$CH$_2$OCH$_2$—), SEM ((CH$_3$)$_3$SiCH$_2$CH$_2$OCH$_2$—) and Ac—, and more preferred are TBS and TBDPS. It is also preferred that $R^2$, $R^4$, $R^6$ and $R^7$ are the same protecting group. Preferred $R^1$ is PMB (p-MeO-Ph-CH$_2$—). The protecting and deprotecting reactions presented in previous reaction schemes are performed according to the state of the art.

The group $R^3$ shown in the schemes is selected from the group consisting of H, OH, =O, OR', OSiR', OSOR', OSO$_2$R', OCOR', OCOOR', CONR', NHR' and NR'R'. R' has the same meaning as defined in formula I. Preferred $R^3$ is a hydroxy or =O.

The group shown as $R^5$ in the schemes is selected from the group consisting of H, SOR', SO$_2$R', C(=O)R', C(=O)OR', C(=O)NR', substituted or unsubstituted alkyl, substituted or unsubstituted alkenyl, substituted or unsubstituted alkynyl, aryl, heteroaryl or aralkyl. And R' has the same meaning as defined in formula I. Preferred $R^5$ is $C_1$-$C_6$ and more preferred is ethyl.

The identity of compounds 9 and 21 can be changed obtaining for other ways compounds 11 and 23 from compound 8, according to the state of the art.

The relative stereochemistry at C-8-C-12 of compounds 3 and 4 was assumed as the same as described in U.S. Pat. No. 5,514,708, 1996 on the basis of coupling constant comparisons cited there. Besides, the stereochemistry of the starting material 6 written above was already indicated by W. R. Roush et al., *Org. Lett.* 1999, 1, 95.

To support this information, the stereochemistry of these carbons was assigned on the basis of NOESY and COSY studies of the intramolecular epoxide opened product 33 which was prepared from 11a in two steps (Scheme 3).

Scheme 3

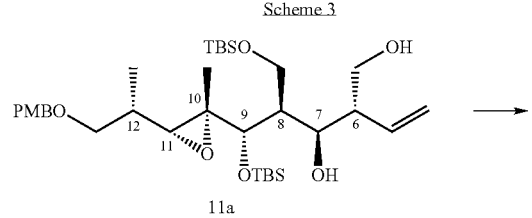

11a

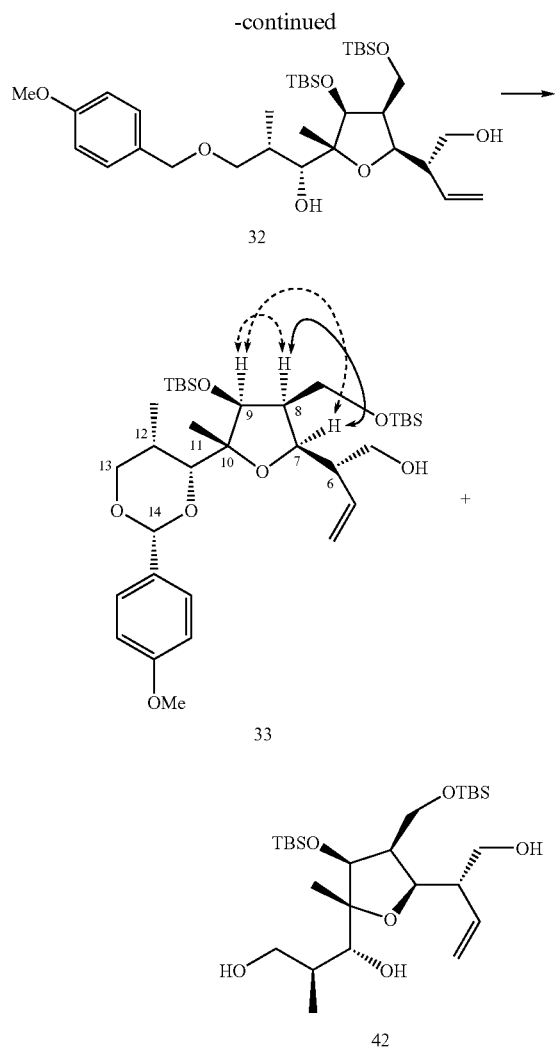

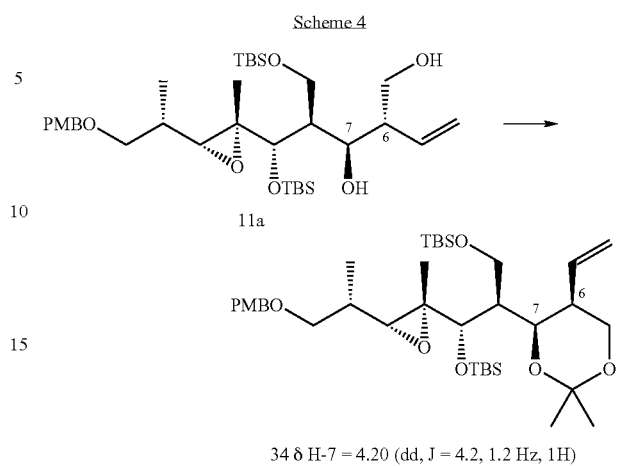

Scheme 4

34 δ H-7 = 4.20 (dd, J = 4.2, 1.2 Hz, 1H)

Finally, the stereochemistry of compounds 3a, 3b, 4a and 4b at C-5 was assigned by conversion of the 1,3 diol of 15a and 15b to the 1,3-syn and anti acetonides respectively (scheme 5).

Scheme 5

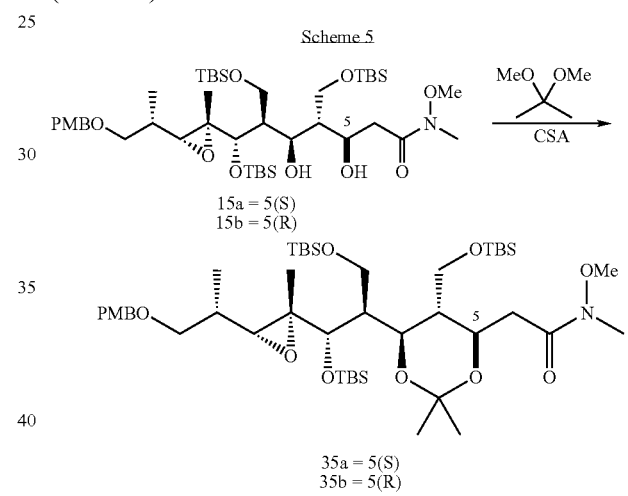

15a = 5(S)
15b = 5(R)

35a = 5(S)
35b = 5(R)

The absolute configuration of C-8 to C-12 has been readily identified by NOE experiments. A syn relative stereochemistry at C-11-C-12 was deduced from the coupling constant (J=1.5 Hz). A NOE signal between H-11 and H-14 indicates both must be in axial position.

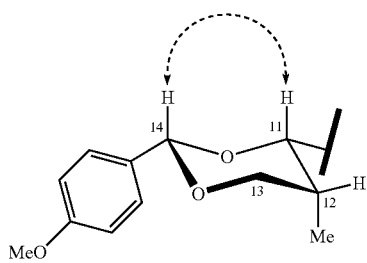

An anti relative stereochemistry at C-6-C-7 was deduced from the small value of the coupling constant of the acetonide 34 prepared from compound 11a (Scheme 4).

The stereochemistry of syn- and anti-1,3-diol acetonides was assigned according to S. D. Rychnovsky et al., *J. Org. Chem.* 1993, 58, 3511-3515, from the $^{13}$C chemical shifts of the acetal methyl groups. In general, the syn-1,3-diol acetonides have acetal methyl shifts at 19 and 30 ppm respectively, while the anti-acetonides have both methyl shifts at about 25 ppm. Indeed, we have tested the reability of this method since the $^{13}$C NMR spectrum of the syn-acetonide 35b shows an axial methyl group at ca 20.2 ppm and an equatorial methyl group at ca. 30.0 ppm, whereas the $^{13}$C spectrum of the anti-acetonide 35a shows both methyl groups at 24.4 and 25.2 ppm.

Unfortunately, it could not be possible to determine the stereochemistry of 3c, 3d, 4c and 4d by preparing the acetonides of 26a and 26b since these compounds could not be separate by conventional methods. In these cases, the configuration at C-5 position was established by conversion of 11a into the 1,3-diols 38a and 38b which can be easily separated. After several reactions, these compounds are leaded to the known intermediates 27c and 27d respectively. The stereochemistry of these compounds was determined from the $^{13}$C chemical shifts of the corresponding acetonides 36a (δ=24.1, 25.0 ppm) and 36b (δ=19.7, 29.9 ppm) (scheme 6).

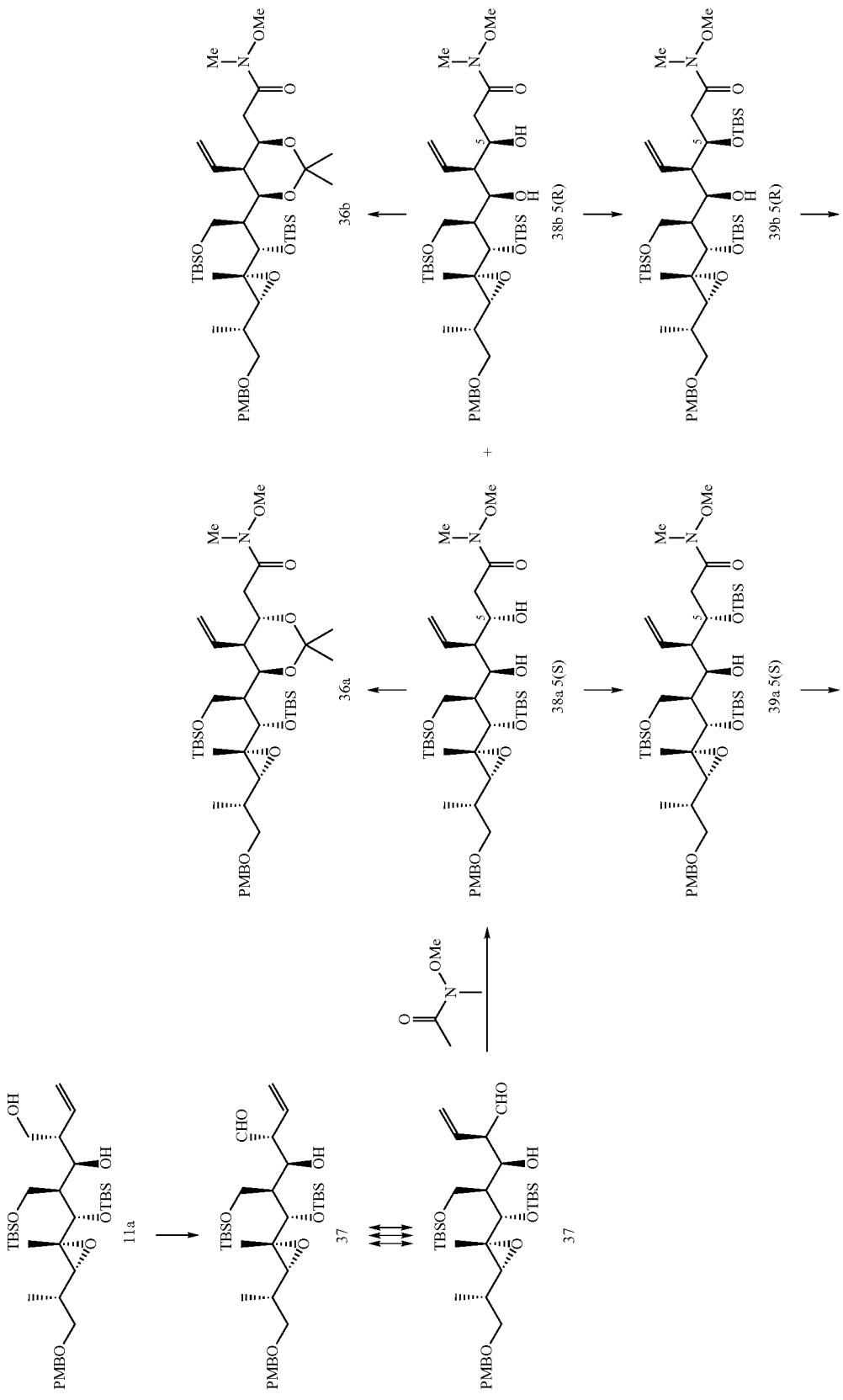
Scheme 6

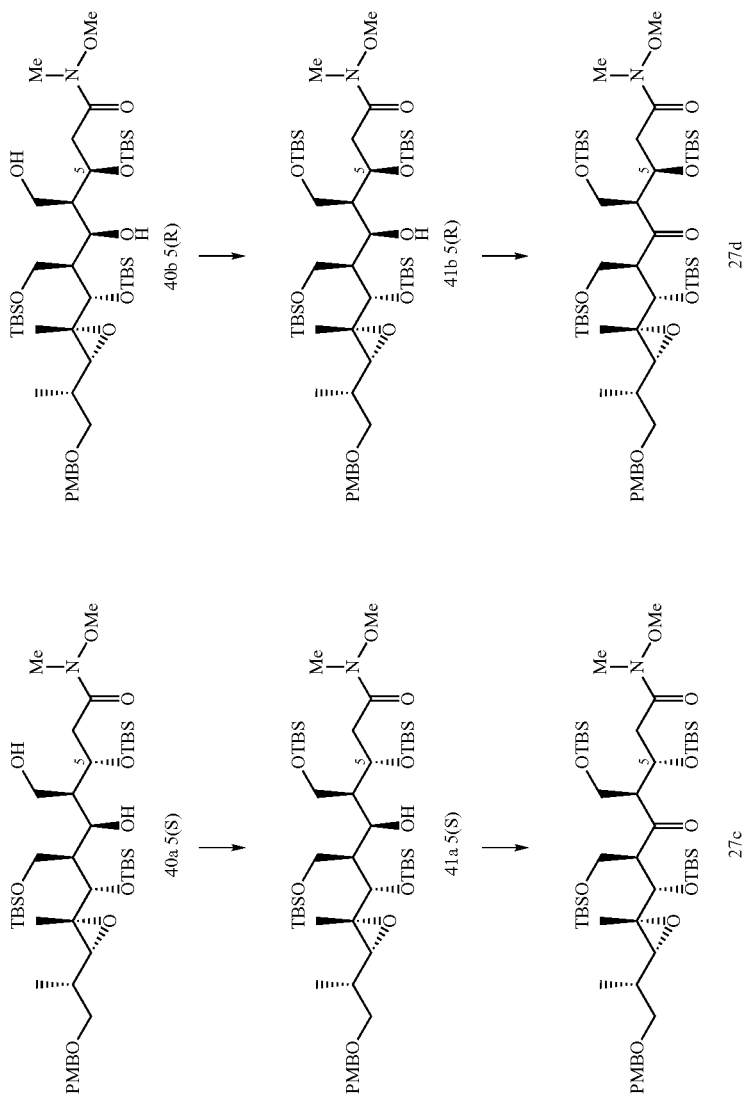

The relative stereochemistry for H-5 and H-6 at myriaporones 3 and 4 was concluded by studying the coupling constants between the protons on the six-membered rings hemiketal monoprotected myriaporones 20 and 31 (scheme 7).

For 20a and 31b, H-4 at δ 1.73 and 1.58 ppm respectively, both with coupling constants of 14.5, 3.5 Hz was assigned to be axial. The others H-4 with upfield chemical shift at δ 2.02 and 2.03 ppm for each compound, have coupling constants of 14.0, 3.5 Hz and 14.5, 3.5 Hz, respectively. These value indicate the proton H-5 should be equatorial.

Similarly, the coupling constants between H-5 and H-6 are, in both cases, around 2 Hz, indicating again that H-5 should be equatorial. Thus, the relative stereochemistry for H-5 and H-6 is concluded to be syn.

On the other hand, the ¹H NMR spectra of compounds 20b and 31a are different from compounds 20a and 31b in coupling constants and, primarily, in the chemical shift. For these compounds, the coupling constants between H-4 (ax) and H-5 are around 12, 13 Hz, indicating H-5 should be in axial.

In addition, the coupling constants between H-5 and H-6 are in concordance with the fact that H-6 is placed in axial to minimize interaction and therefore, the relative stereochemistry for H-5 and H-6 is concluded to be anti.

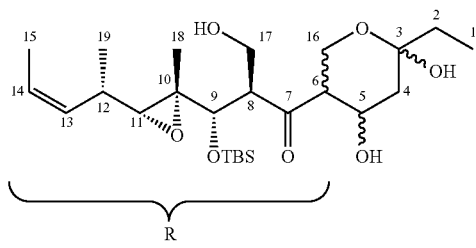

Scheme 7

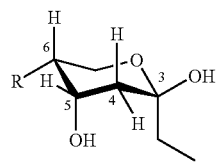

20a

H-4$_{ax}$ δ 1.73 (dd, J = 3, 14 Hz)
H-4$_{eq}$ δ 2.02 (dd, J = 3.5, 14 Hz)
H-5$_{eq}$ δ 4.79 (d, J = 2.5 Hz)
H-6$_{ax}$ δ 2.77 (ddd, J = 2.5, 5, 11.5 Hz)

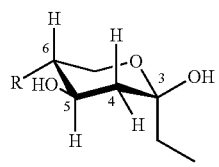

20b

H-4$_{ax}$ δ 1.46 (dd, J = 12, 13 Hz)
H-4$_{eq}$ δ 2.08 (dd, J = 5, 12.5 Hz)
H-5$_{ax}$ δ 4.38 (ddd, J = 5, 11.5, 15.5 Hz)
H-6$_{ax}$ δ 2.77 (ddd, J = 4.5, 11, 14.5 Hz)

-continued

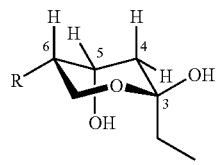

31b

H-4$_{ax}$ δ 1.58 (dd, J = 3, 14 Hz)
H-4$_{eq}$ δ 2.03 (dd, J = 3.5, 14.5 Hz)
H-5$_{eq}$ δ 4.62 (bs)
H-6$_{ax}$ δ 2.94 (ddd, J = 2, 5, 11.5 Hz)

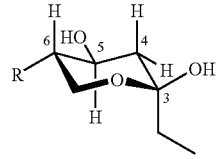

31a

H-4$_{ax}$ δ 1.46 (dd, J = 11.5, 13 Hz)
H-4$_{eq}$ δ 2.09 (dd, J = 4.5, 12.5 Hz)
H-5$_{ax}$ δ 4.79 (ddd, J = 4.5, 11, 12.6 Hz)
H-6$_{ax}$ δ 2.77 (ddd, J = 5.5, 11, 17.5 Hz)

The stereochemistry at C-3 in the hemiketal compounds could not be assigned by NOE experiments. In the scheme 7, the hemiketal hydroxy group at C3 was arbitrarily placed equatorial.

Another especially preferred embodiment of the present invention is pharmaceutical compositions useful as antitumor agents which contain as active ingredient a compound or compounds of the invention, as well as the processes for their preparation.

An important feature of the above described compounds of formula I is their bioactivity and in particular their cytotoxic activity. With this invention we provide novel pharmaceutical compositions of compounds of general formula I that possess cytotoxic activity, and their use as antitumor agents. Thus the present invention further provides pharmaceutical compositions comprising a compound of this invention, a pharmaceutically acceptable salts, derivatives, prodrugs or stereoisomers thereof with a pharmaceutically acceptable carrier.

Examples of pharmaceutical compositions include any solid (tablets, pills, capsules, granules etc.) or liquid (solutions, suspensions or emulsions) with suitable composition for oral, topical or parenteral administration.

Administration of the compounds or compositions of the present invention may be any suitable method, such as intravenous infusion, oral preparation, intraperitoneal and intravenous preparation. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 1 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time.

Antitumoral activities of these compounds include among others leukaemias, lung cancer, colon cancer, kidney cancer, prostate cancer, ovarian cancer, breast cancer, pancreas cancer, cervix cancer, sarcomas and melanomas.

The present invention will be further explained with the following examples which are not limiting. As can be seen, this methodology allows for the synthesis of myriaporone compounds with the desired stereospecificity.

EXAMPLES

Example 1

Compound 7a

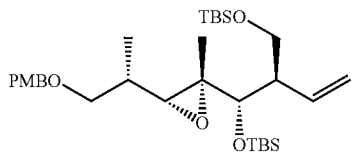

To a solution of 6 (3.51 g, 7.8 mmol) in CH$_2$Cl$_2$ (40 mL) was added imidazole (1.59 g, 23.4 mmol) and TBSCl (1.76 g, 11.7 mmol) at 23° C. The reaction mixture was stirred at 23° C. for 3 h. HCl 0.1 N was added until pH=4-5, and the mixture was extracted with CH$_2$Cl$_2$ (2×). The combined organic layers were dried over Na$_2$SO$_4$, filtered, and concentrated under reduced pressure. The residue was purified by chromatography on silica gel (Hex:EtOAc, 10:1) to obtain compound 7a (3.44 g, 78%) as a colourless oil.

$^1$H NMR (300 MHz, CDCl$_3$) δ 7.23 (d, J=8.7 Hz, 2H), 6.86 (d, J=8.7 Hz, 2H), 5.83 (m, 1H), 4.99 (dd, J=10.5, 1.8 Hz, 1H), 4.86 (dd, J=17.4, 2.1 Hz, 1H), 4.42 (s, 2H), 3.80 (s, 3H), 3.44 (m, 2H), 3.33 (d, J=6.6 Hz, 1H), 2.47 (d, J=9.6 Hz, 1H), 2.24 (m, 1H), 1.75 (m, 1H), 1.08 (d, J=6.6 Hz, 3H), 0.91 (s, 9H), 0.88 (s, 9H), 0.13 (s, 3H), 0.04 (s, 3H), 0.02 (s, 3H), 0.01 (s, 3H). $^{13}$C NMR (75 MHz, CDCl$_3$) δ 159.1, 136.2, 130.3, 129.1, 117.1, 113.7, 72.9, 72.6, 64.9, 64.6, 63.9, 55.2, 51.3, 33.1, 25.9, 25.8, 18.2, 18.1, 14.9, 13.3, −4.2, −5.3, −5.4, −5.5. MS (ESI) m/z: 587 (M+23)$^+$.

[α]$^{25}_D$ −9.5 (c 0.52, CH$_2$Cl$_2$).
R$_f$=0.61 (Hex:EtOAc, 4:1).

Example 2

Compound 7b

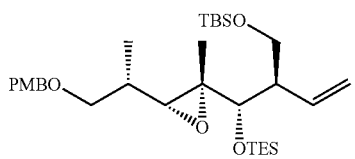

Compound 7b was prepared as a colourless oil, in the same way as 7b from the corresponding precursor of 6, according to the procedure described by W. Roush et al., *Org. Lett.* 1999, 1, 95) by using TESOTf instead of TBSOTf in equivalent amounts for the secondary alcohol protection step.

$^1$H NMR (300 MHz, CDCl$_3$) δ 7.24 (d, J=8.7 Hz, 2H), 6.87 (d, J=8.7 Hz, 2H), 5.92-5.80 (m, 1H), 5.02 (dd, J=10.2, 1.8 Hz, 1H), 4.90 (dd, J=17.4, 1.8 Hz, 1H), 4.42 (s, 2H), 3.78 (s, 3H), 3.56-3.42 (m, 3H), 3.38-3.34 (m, 2H), 2.52 (d, J=9.0 Hz, 1H), 2.27-2.23 (m, 1H), 1.81-1.76 (m, 1H), 1.27 (s, 3H), 1.10 (d, J=6.6 Hz, 3H), 0.98 (t, J=7.8 Hz, 9H), 0.90 (s, 9H), 0.71-0.62 (m, 6H), 0.05 (s, 3H), 0.04 (s, 3H).

$^{13}$C NMR (75 MHz, CDCl$_3$) δ 159.1, 136.4, 130.2, 129.0, 116.8, 113.6, 76.9, 72.8, 72.6, 64.7, 64.6, 63.8, 55.0, 51.1, 33.2, 25.7, 18.0, 14.8, 13.1, 6.9, 4.8, −5.3, −5.5.

MS (ESI) m/z: 587 (M+23)$^+$, 565 (M+1)$^+$.
R$_f$=0.62 (Hexane:EtOAc, 4:1).

Example 3

Compound 7c

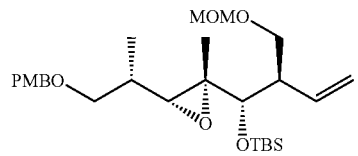

To a solution of 6 (450 mg, 1 mmol) in CH$_2$Cl$_2$ (20 mL) was added DIPEA (1.74 mL, 10 mmol) and MOMBr (0.45 mL, 5 mmol) at 0° C. The reaction mixture was stirred at 0° C. for 4 h. Then, a saturated aqueous solution of NH$_4$Cl was added and the mixture was extracted with CH$_2$Cl$_2$ (2×30 mL). The combined organic layers were dried over Na$_2$SO$_4$, filtered, and concentrated under reduced pressure. The residue was purified by chromatography on silica gel (Hex:EtOAc, 10:1) to obtain compound 7c (250 mg, 51%) as a colourless oil.

$^1$H NMR (300 MHz, CDCl$_3$) δ 7.24 (d, J=8.4 Hz, 2H), 6.87 (d, J=8.4 Hz, 2H), 5.90-5.78 (m, 1H), 5.04 (dd, J=10.2, 2.1 Hz, 1H), 4.95 (dd, J=17.4, 2.1 Hz, 1H), 4.56 (s, 2H), 4.43 (s, 2H), 3.80 (s, 3H), 3.51-3.40 (m, 3H), 3.37-3.34 (m, 4H), 3.33 (s, 3H), 2.52 (d, J=9.3 Hz, 1H), 2.43-2.40 (m, 1H), 1.79-1.65 (m, 1H), 1.25 (s, 3H), 1.09 (d, J=6.6 Hz, 3H), 0.91 (s, 9H), 0.14 (s, 3H), 0.04 (s, 3H).

$^{13}$C NMR (75 MHz, CDCl$_3$) δ 159.4, 136.4, 130.6, 129.4, 117.6, 114.0, 96.8, 78.2, 73.1, 72.7, 69.0, 64.8, 64.7, 55.6, 55.5, 49.2, 33.4, 26.2, 18.5, 15.2, 13.5, −3.9, −5.3.

R$_f$=0.52 (Hex:EtOAc, 4:1).

Example 4

Compound 7d

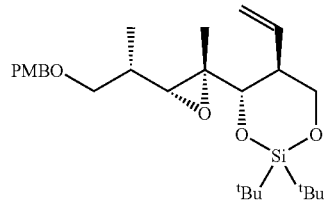

To a solution of the corresponding diol (581 mg, 1.73 mmol) in CH$_2$Cl$_2$ (20 mL) was added 2,6-lutidine (0.61 g, 5.2 mmol) and t-Bu$_2$Si(OTf)$_2$ (9.48 mL, 2.6 mmol) at 0° C. The reaction mixture was stirred at 0° C. for 2 h. Then, a saturated aqueous solution of NH$_4$Cl was added and the mixture was extracted with CH$_2$Cl$_2$ (2×30 mL). The combined organic layers were dried over Na$_2$SO$_4$, filtered, and concentrated under reduced pressure. The residue was purified by flash column chromatography on silica gel (Hex:EtOAc, 10:1) to obtain compound 7d (330 mg, 40%) as a colourless oil.

$^1$H NMR (300 MHz, CDCl$_3$) d 7.23 (d, J=8.7 Hz, 2H), 6.87 (d, J=8.7 Hz, 2H), 6.40 (ddd, J=17.1, 9.9, 8.7 Hz, 1H), 5.10 (dd, J=10.5, 1.8 Hz, 1H), 5.06 (dd, J=17.1, 1.8 Hz, 1H), 4.41 (s, 2H), 4.35 (dd J=11.1, 3.0 Hz, 1H), 4.06 (d, J=3.0 Hz, 1H), 4.00 (dd, J=11.1, 2.4 Hz, 1H), 3.80 (s, 3H), 3.34 (d, J=6.3 Hz, 2H), 2.72 (d, J=9.3 Hz, 1H), 2.41-2.37 (m, 1H), 1.78-1.73 (m, 1H), 1.28 (s, 3H), 1.09 (d, J=6.6 Hz, 3H), 1.07 (s, 9H), 1.05 (s, 9H).

$^{13}$C NMR (75 MHz, CDCl$_3$) δ 159.4, 136.9, 130.7, 129.2, 116.9, 114.0, 79.6, 73.1, 72.8, 70.4, 63.7, 62.3, 55.5, 47.0, 33.3, 28.6, 27.7, 23.5, 21.0, 15.1.

MS (ESI) m/z: 499 (M+23)$^+$.

R$_f$=0.41 (Hex:EtOAc, 4:1).

Example 5

Compound 8a

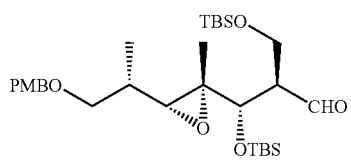

Over a solution of 7a (21.94 g, 38.7 mmol) in CH$_2$Cl$_2$ (150 mL) was bubbled a current of O$_3$ during 50 min at −78° C. Then, Ph$_3$P (30.45 g, 116.1 mmol) was added and the mixture was allowed to warm to room temperature, and the stirring was continued for 12h. The mixture was concentrated under reduced pressure and the residue was purified by flash column chromatography on silica gel (Hex:EtOAc, 20:1) to afford compound 8a (15.82 g, 72%) as a colourless oil.

$^1$H NMR (300 MHz, CDCl$_3$) δ 9.67 (d, J=3.0 Hz, 1H), 7.20 (d, J=8.4 Hz, 2H), 6.84 (d, J=8.4 Hz, 2H), 4.38 (m, 2H), 3.84 (dd, J=10.2, 5.1 Hz, 1H), 3.80 (s, 3H), 3.69 (m, 2H), 3.41 (dd, J=9.3, 5.1 Hz, 1H), 3.31 (t, J=9.0 Hz, 1H), 2.59 (d, J=9.3 Hz, 1H), 2.50 (m, 1H), 1.81 (m, 1H), 1.30 (s, 3H), 1.06 (d, J=6.3 Hz, 3H), 0.86 (s, 18H), 0.14 (s, 3H), 0.04 (s, 3H), 0.02 (s, 3H), 0.01 (s, 3H).

$^{13}$C NMR (75 MHz, CDCl$_3$) δ 203.8, 159.5, 130.3, 129.4, 114.0, 76.5, 73.2, 73.0, 65.1, 64.0, 60.1, 57.9, 55.4, 33.6, 26.0, 26.0, 18.3, 15.0, 13.0, −4.0, −5.2, −5.3, −5.5.

MS (ESI) m/z: 589 (M+23)$^+$.

[α]$^{25}$$_D$ −11.6 (c 0.50, CH$_2$Cl$_2$).

R$_f$=0.59 (Hex:EtOAc, 4:1).

Example 6

Compound 8b

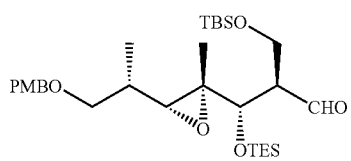

To a solution of 7b (0.86 g, 1.52 mmol) in THF:H$_2$O (10:1, 22 mL) was added NMO (0.623 g, 5.32 mmol) and OsO$_4$ (4.56 mL, 0.456 mmol, 0.1 M in $^t$BuOH) at 23° C. and the reaction mixture was stirred at 23° C. overnight. Florisil (6 g), NaHSO$_3$ (6 g), and EtOAc (100 mL) were added and the mixture was stirred vigorously during 30 min. The mixture was filtered through a pad of Celite, and the filtrate was concentrated to provide the corresponding diol. To a solution of this diol in THF (10 mL) was added a solution of NaIO$_4$ (1.95 g, 9.12 mmol) in H$_2$O (8 mL) at 0° C. and the mixture was stirred at 23° C. for 1 h. The reaction was quenched by addition of a saturated aqueous solution of NH$_4$Cl (20 mL) and then, extracted with CH$_2$Cl$_2$ (2×20 mL). The combined organic layers were dried over Na$_2$SO$_4$, filtered, and concentrated under reduced pressure. The residue was purified by flash column chromatography on silica gel (Hex:EtOAc, 10:1) to afford compound 8b (0.67 g, 78%) as a colourless oil.

$^1$H NMR (300 MHz, CDCl$_3$) δ 9.68 (d, J=2.4 Hz, 1H), 7.17 (d, J=8.4 Hz, 2H), 6.83 (d, J=8.4 Hz, 2H), 4.36 (q, J=11.4 Hz, 2H), 3.83 (dd, J=10.2, 5.1 Hz, 1H), 3.76 (s, 3H), 3.74 (d, J=6.3 Hz, 1H), 3.67 (dd, J=10.2, 5.7 Hz, 1H), 3.39 (dd, J=9.3, 5.1 Hz, 1H), 3.30 (t, J=9.0 Hz, 1H), 2.60 (d, J=9.3 Hz, 1H), 2.47-2.40 (m, 1H), 1.82-1.78 (m, 1H), 1.28 (s, 3H), 1.04 (d, J=6.6 Hz, 3H), 0.92 (t, J=7.8 Hz, 9H), 0.85 (s, 9H), 0.62 (q, J=7.8 Hz, 6H), 0.01, (s, 3H), 0.00 (s, 3H).

$^{13}$C NMR (75 MHz, CDCl$_3$) δ 203.4, 159.1, 129.9, 129.0, 113.6, 75.9, 73.8, 72.6, 64.9, 63.5, 59.7, 57.4, 55.0, 33.3, 25.6, 17.9, 14.6, 12.5, 6.7, 4.6, −5.5, −5.7.

MS (ESI) m/z: 589 (M+23)$^+$.

R$_f$=0.54 (Hexane:EtOAc, 4:1).

Example 7

Compound 9

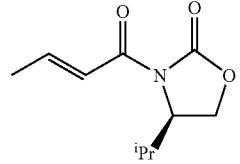

Compound 9 was prepared following the procedure described by D. A. Evans et al, *J. Am. Chem. Soc.* 1984, 106, 4261-4263.

$^1$H NMR (300 MHz, CDCl$_3$) δ 7.21 (m, 1H), 7.12 (m, 1H), 4.44 (m, 1H), 4.20 (m, 2H), 2.36 (m, 1H), 1.91 (dd, J=6.6, 1.2 Hz, 3H), 0.88 (d, J=6.9 Hz, 3H), 0.83 (d, J=6.9 Hz, 3H).

Example 8

Compound 10a

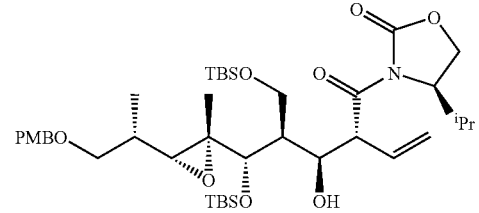

To a solution of 9 (17.75 g, 0.09 mol) in CH$_2$Cl$_2$ (270 mL) was added Bu$_2$BOTf (99 mL, 1M in CH$_2$Cl$_2$, 0.099 mol) and Et$_3$N (17.56 mL, 0.126 mol) at −78° C. The reaction mixture was stirred 1 h at −78° C., 15 min at 0° C. and recooled at −78°

C. This solution was added in three portion in 5 h over a solution of 8a (17.18 g, 0.03 mol) in CH₂Cl₂ (100 mL) at 0° C. and the mixture was stirred at −30° C. for an additional 12 h. Then, saturated aqueous solution of NH₄Cl (300 mL) was added and the reaction was extracted with CH₂Cl₂ (2×200 mL). The combined organic layers were dried over Na₂SO₄, filtered, and concentrated under reduced pressure. The residue was dissolved in 400 mL of ether, 200 mL of buffer solution and 200 mL of H₂O₂ and the mixture was stirred at 0° C. for 1 h. Then, the reaction was extracted and the organic phase was washed with a saturated aqueous solution of NaHCO₃ (200 mL) and brine (200 mL). The organic layer were dried over Na₂SO₄, filtered, and concentrated under reduced pressure. The residue was purified by flash column chromatography on silica gel (Hex:EtOAc, from 10:1 to 2:1) to afford compound 10a (21 g, 92%) as a colourless oil.

$^1$H NMR (300 MHz, CDCl₃) δ 7.19 (d, J=8.4 Hz, 2H), 6.85 (d, J=8.4 Hz, 2H), 5.93 (m, 1H), 5.41 (d, J=17.1 Hz, 1H), 5.28 (d, J=9.3 Hz, 1H), 4.92 (t, J=9.6 Hz, 1H), 4.63 (dddd, J=9.3, 6.3, 5.1, 1.5 Hz, 1H), 4.43 (s, 3H), 4.34 (m, 1H), 4.12 (m, 2H), 3.85 (m, 1H), 3.80 (s, 3H), 3.73 (m, 2H), 4.44 (m, 2H), 2.58 (d, J=9.3 Hz, 1H), 2.30 (m, 1H), 1.81 (m, 1H), 1.38 (s, 3H), 1.10 (d, J=6.6 Hz, 3H), 0.93 (s, 9H), 0.87 (s, 9H), 0.84 (d, J=7.5 Hz, 3H), 0.80 (d, J=6.9 Hz, 3H), 0.17 (s, 3H), 0.12 (s, 3H), 0.09 (s, 3H), 0.04 (s, 3H).

$^{13}$C NMR (75 MHz, CDCl₃) δ 172.0, 159.0, 153.3, 135.3, 129.9, 128.6, 113.7, 77.4, 72.6, 71.0, 64.0, 63.4, 62.6, 59.8, 58.4, 58.0, 55.2, 51.2, 45.2, 40.1, 33.6, 26.7, 28.3, 27.8, 26.1, 25.8, 18.3, 17.9, 15.1, 14.6, 14.3, 13.1, −4.4, −5.4, −5.5, −5.6.

MS (ESI) m/z: 786 (M+23)$^+$.

$[\alpha]^{25}_D$ +3.1 (c 0.53, CH₂Cl₂).

$R_f$=0.35 (Hex:EtOAc, 4:1).

Example 9

Compound 10b

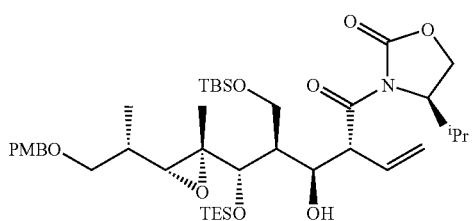

The title compound was prepared as described above from 8b (1.2 g, 2.11 mmol). Chromatography (SiO₂,) provided 10b (1.16 g, 80%) as a colourless oil.

$^1$H NMR (300 MHz, CDCl₃) δ 7.20 (d, J=8.4 Hz, 2H), 6.84 (d, J=8.4 Hz, 2H), 5.85-6.03 (m, 1H), 5.19-5.44 (m, 2H), 4.93 (t, J=9.3 Hz, 1H), 4.59-4.64 (m, 1H), 4.42-4.46 (m, 1H), 4.42 (s, 2H), 4.19-4.36 (m, 4H), 4.05-4.15 (m, 2H), 3.80 (s, 3H), 3.65-3.83 (m, 3H), 3.40-3.46 (m, 1H), 2.57 (d, J=9.3 Hz, 1H), 2.27-2.36 (m, 1H), 1.78-1.86 (m, 1H), 1.56-1.64 (m, 1H), 1.37 (s, 3H), 1.28-1.38 (m, 6H), 0.92 (s, 9H), 0.88-0.99 (m, 6H), 0.62-0.68 (m, 9H), 0.09 (s, 3H), 0.04 (s, 3H).

$R_f$=0.42 (Hex:EtOAc, 4:1).

Example 10

Compound 11a

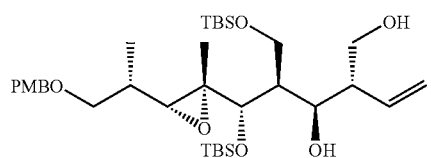

To a solution of 10a (14.5 g, 18.9 mmol) in THF:H₂O (5:1, 120 mL), LiBH₄ (141.9 mL, 2.0 M in THF, 283.7 mmol,) was added at 0° C. The reaction mixture was stirred 30 min at 0° C. and 6 h at 23° C. Saturated aqueous solution of NH₄Cl (150 mL) was added and the mixture was extracted with EtOAc (3×150 mL). The combined organic layers were dried over Na₂SO₄, filtered, and concentrated under reduced pressure. The residue was dissolved in 400 mL of ether, 200 mL of buffer solution and 200 mL of H₂O₂ and the mixture was stirred at 0° C. for 2 h. Then, the reaction was extracted and the organic phase was washed with a saturated aqueous solution of NaHCO₃ (2×200 mL). The organic layer were dried over Na₂SO₄, filtered, and concentrated under reduced pressure. The residue was purified by flash column chromatography on silica gel (Hex:EtOAc 5:1) to afford compound 11a (10.5 g, 87%) as a colourless oil.

$^1$H NMR (300 MHz, CDCl₃) δ 7.22 (d, J=8.4 Hz, 2H), 6.87 (d, J=8.4 Hz, 2H), 5.84 (m, 1H), 5.21 (d, J=8.7 Hz, 1H), 5.14 (d, J=17.4 Hz, 1H), 4.42 (s, 2H), 4.19 (m, 1H), 3.84 (m, 1H), 3.80 (s, 3H), 3.75 (m, 1H), 3.61 (m, 2H), 3.48 (m, 2H), 3.36 (m, 2H), 2.53 (d, J=9.3 Hz, 1H), 2.27 (m, 1H), 1.80 (m, 1H), 1.32 (s, 3H), 1.05 (d, J=6.9 Hz, 3H), 0.91 (s, 9H), 0.88 (s, 9H), 0.15 (s, 3H), 0.09 (s, 3H), 0.05 (s, 3H), 0.04 (s, 3H).

$^{13}$C NMR (75 MHz, CDCl₃) δ 159.5, 137.6, 130.3, 129.4, 118.3, 114.0, 73.2, 73.0, 71.2, 64.9, 64.4, 60.4, 55.5, 51.1, 47.0, 33.5, 29.9, 26.4, 26.3, 26.0, 18.4, 18.2, 15.0, 14.0, −4.2, −5.1, −5.2.

MS (ESI) m/z: 662 (M+23)$^+$.

$[\alpha]^{25}_D$ +0.7 (c 0.54, CH₂Cl₂).

$R_f$=0.2 (Hex:EtOAc, 4:1).

Example 11

Compound 11b

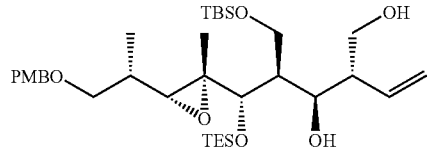

The title compound was prepared as described above from 10b (1.53 g, 2 mmol). Chromatography (SiO₂,) provided 11b (1 g, 80%) as a colourless oil.

$^1$H NMR (300 MHz, CDCl₃) δ 7.22 (d, J=8.7 Hz, 2H), 6.87 (d, J=8.7 Hz, 2H), 5.92-5.80 (m, 1H), 5.92-5.80 (m, 1H), 5.21 (dd, J=10.2, 2.1 Hz, 1H), 5.14 (dd, J=17.1, 2.1 Hz, 1H), 4.40 (s, 2H), 4.19-4.16 (m, 1H), 3.84 (dd, J=6.0, 1.5, 3H), 3.80 (s, 3H), 3.72 (dd, J=6.3, 2.4 Hz, 1H), 3.62 (d, J=4.5 Hz, 1H), 3.56 (d, J=3.6, 1H), 3.52-3.48 (m, 1H), 3.38-3.33 (m, 2H), 2.53 (d, J=9.0 Hz, 1H), 2.27-2.22 (m, 1H), 1.83-1.78 (m, 1H), 1.73-

1.67 (m, 1H), 1.30 (s, 3H), 1.04 (d, J=6.9 Hz, 3H), 0.95 (t, J=7.8 Hz, 9H), 0.87 (s, 9H), 0.67 (q, J=7.8 Hz, 6H), 0.05 (s, 3H), 0.04 (s, 3H).

$^{13}$C NMR (75 MHz, CDCl$_3$) δ 159.2, 137.4, 130.1, 129.1, 118.0, 113.7, 77.4, 72.9, 72.7, 71.1, 64.9, 64.3, 64.2, 60.2, 55.2, 51.0, 46.6, 33.3, 25.7, 17.9, 14.8, 13.5, 6.8, 4.7, −5.3, −5.5.

R$_f$=0.18 (Hex:EtOAc 4:1).

Example 12

Compound 12a

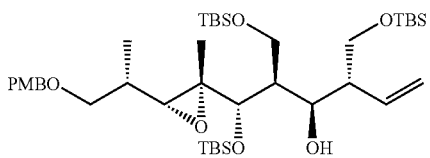

To a solution of 11a (7.43 g, 11.6 mmol) in CH$_2$Cl$_2$ (100 mL) was added imidazole (3.16 g, 46.4 mmol) and TBSCl (3.48 g, 23.2 mmol) at 23° C. The reaction mixture was stirred at 23° C. for 4 h. 0.1N HCl was added until pH=4-5, and the reaction was extracted with CH$_2$Cl$_2$ (2×150 mL). The combined organic layers were dried over Na$_2$SO$_4$, filtered, and concentrated under reduced pressure. The residue was purified by flash column chromatography on silica gel (Hex:EtOAc, from 10:1 to 4:1) to obtain compound 12a (8.47 g, 97%) as a colourless oil.

$^1$H NMR (300 MHz, CDCl$_3$) δ 7.22 (d, J=8.6 Hz, 2H), 6.86 (d, J=8.6 Hz, 2H), 5.86 (m, 1H), 5.07 (m, 2H), 4.41 (m, 2H), 4.29 (br s, 1H), 3.88 (m, 1H), 3.80 (s, 3H), 3.74 (m, 1H), 3.62 (m, 2H), 3.48 (m, 1H), 3.34 (d, J=6.8 Hz, 2H), 3.17 (d, J=4.9 Hz, 1H), 2.55 (d, J=9.2 Hz, 1H), 2.26 (m, 1H), 1.78 (m, 2H), 1.32 (s, 3H), 1.06 (d, J=6.6 Hz, 3H), 0.92 (s, 9H), 0.88 (s, 9H), 0.87 (s, 9H), 0.16 (s, 3H), 0.10 (s, 3H), 0.05 (s, 3H), 0.03 (s, 9H).

$^{13}$C NMR (75 MHz, CDCl$_3$) δ 159.4, 138.0, 130.5, 129.2, 117.1, 114.0, 77.4, 73.1, 72.8, 69.4, 65.0, 64.8, 64.5, 60.7, 55.4, 51.9, 46.9, 33.7, 29.9, 26.3, 26.2, 26.1, 18.6, 18.5, 18.1, 15.1, 13.5, −4.3, −5.0, −5.1, −5.2.

MS (ESI) m/z: 775 (M+23)$^+$, 753 (M+1)$^+$.

[α]$^{25}_D$+3.0 (c 0.54, CH$_2$Cl$_2$).

R$_f$=0.66 (Hex:EtOAc, 4:1).

Example 13

Compound 12b

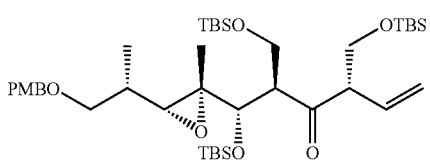

To a solution of 12a (500 mg, 0.663 mmol) in CH$_2$Cl$_2$ (30 mL) was added Dess-Martin periodinane (562 mg, 1.32 mmol) at 23° C. The reaction mixture was stirred at 23° C. for 3 h. Then, saturated aqueous solution of NaHCO$_3$ (30 mL) was added and the mixture was extracted with CH$_2$Cl$_2$ (3×40 mL). The combined organic layers were dried over Na$_2$SO$_4$, filtered, and concentrated under reduced pressure. The residue was purified by flash column chromatography on silica gel (Hex:EtOAc, 10:1) to obtain compound 12b (414 mg, 83%) as a colourless oil.

$^1$H NMR (300 MHz, CDCl$_3$) δ 7.24 (d, J=8.4 Hz, 2H), 6.87 (d, J=8.4 Hz, 2H), 5.78 (m, 1H), 5.23 (m, 2H), 4.42 (dd, J=16.2, 11.4, 2H), 4.02 (dd, J=10.2, 4.8 Hz, 1H), 3.81 (s, 3H), 3.74 (m, 1H), 3.61 (m, 2H), 3.33 (m, 3H), 2.48 (d, J=9.3 Hz, 1H), 1.77 (m, 1H), 1.29 (s, 3H), 1.06 (d, J=6.6 Hz, 3H), 0.87 (s, 9H), 0.86 (s, 9H), 0.84 (s, 9H), 0.11 (s, 3H), 0.04 (s, 3H), 0.03, (s, 3H), 0.02, (s, 3H), −0.01, (s, 3H), −0.03 (s, 3H).

$^{13}$C NMR (75 MHz, CDCl$_3$) δ 209.2, 159.1, 134.3, 130.2, 129.0, 119.3, 113.7, 77.5, 72.7, 72.2, 64.3, 63.0, 62.3, 62.2, 61.1, 55.9, 55.2, 33.6, 29.7, 26.0, 25.9, 25.8, 18.2, 18.1, 15.0, 12.2, −4.5, −5.2, −5.3, −5.4, −5.4, −5.5.

MS (ESI) m/z: 773 (M+23)$^+$.

Example 14

Compound 12c

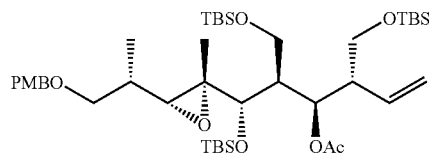

To a solution of 12a (1.5 g, 1.99 mmol) in CH$_2$Cl$_2$ (30 mL) was added Et$_3$N (5.55 mL, 39.82 mmol), DMAP (24 mg, 0.119 mmol) and Ac$_2$O (1.88 mL, 19.91 mmol) at 0° C. The reaction mixture was stirred at 23° C. for 12 h. Then, a saturated aqueous solution of NaHCO$_3$ (50 mL) was added and the mixture was extracted with CH$_2$Cl$_2$ (3×30 mL). The combined organic layers were washed with HCl 0.1 N, dried over Na$_2$SO$_4$, filtered, and concentrated. The residue was purified by chromatography on silica gel (Hex:EtOAc, 10:1) to obtain compound 12c (1.12 g, 71%) as a colourless oil.

$^1$H NMR (300 MHz, CDCl$_3$) δ 7.23 (d, J=8.5 Hz, 2H), 6.86 (d, J=8.5 Hz, 2H), 5.66 (m, 1H), 5.48 (m, 2H), 5.09 (m, 2H), 4.42 (m, 2H), 3.80 (s, 3H), 3.60 (m, 2H), 3.46 (m, 2H), 3.34 (m, 4H), 2.61 (m, 1H), 2.48 (d, J=9.1 Hz, 1H), 1.95 (s, 3H), 1.77 (m, 1H), 1.34 (s, 3H), 1.06 (d, J=6.6 Hz, 3H), 0.91 (s, 9H), 0.88 (s, 9H), 0.86 (s, 9H), 0.11 (s, 3H), 0.05 (s, 3H), 0.03 (s, 6H), 0.01 (s, 3H), −0.01 (s, 3H).

$^{13}$C NMR (75 MHz, CDCl$_3$) δ 169.8, 159.4, 136.7, 130.6, 129.3, 118.3, 114.0, 76.9, 73.0, 72.6, 70.6, 64.4, 59.9, 55.4, 52.5, 47.1, 33.4, 26.3, 26.1, 26.1, 21.4, 18.6, 18.3, 15.2, 13.3, −4.1, −4.9, −5.0, −5.1, −5.2, −5.2.

MS (ESI)m/z: 817 (M+23)$^+$, 812 (M+18)$^+$.

R$_f$=0.63 (Hex:EtOAc, 4:1).

Example 15

Compound 12d

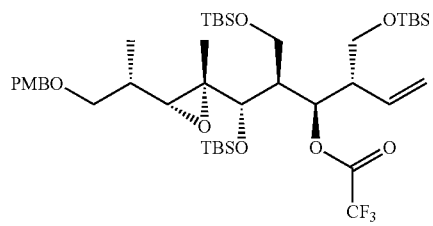

To a solution of 12a (215 mg, 0.285 mmol) in THF (5 mL) was added Py (0.46 mL, 5.7 mmol), DMAP (53 mg, 0.427 mmol) and (CF$_3$CO)$_2$O (0.40 mL, 2.85 mmol) at 0° C. The reaction mixture was stirred at 23° C. for 12 h. Then, a saturated aqueous solution of NaHCO$_3$ (7 mL) was added and the reaction was extracted with CH$_2$Cl$_2$ (3×10 mL). The combined organic layers were washed with HCl 0.1N (2×4 mL), dried over Na$_2$SO$_4$, filtered, and concentrated under reduced pressure. The residue was purified by flash column chromatography on silica gel (Hex:EtOAc, 18:1) to obtain compound 12d (221 mg, 91%) as a colourless oil.

$^1$H NMR (300 MHz, CDCl$_3$) δ 7.22 (d, J=8.7 Hz, 2H), 6.87 (d, J=8.7 Hz, 2H), 5.75 (m, 1H), 5.65 (m, 1H), 5.09 (m, 2H), 4.42 (s, 2H), 3.81 (s, 3H), 3.47 (m, 8H), 2.78 (m, 1H), 2.51 (d, J=9.0 Hz, 1H), 2.11 (m, 1H), 1.78 (m, 1H), 1.33 (s, 3H), 1.06 (d, J=6.9 Hz, 3H), 0.91 (s, 9H), 0.88 (s, 18H), 0.12 (s, 3H), 0.06 (s, 3H), 0.03 (s, 3H), 0.01 (s, 6H), 0.00 (s, 3H).

$^{13}$C NMR (75 MHz, CDCl$_3$) δ 159.2, 156.0 (d, J$_{C-F}$=41.0 Hz), 134.6, 130.2, 129.1, 119.4, 113.8, 76.0, 75.4, 72.9, 72.7, 64.3, 64.0, 63.8, 59.3, 55.2, 51.6, 46.2, 33.1, 26.1, 25.9, 18.3, 18.0, 14.8, 14.1, 13.2, −4.5, −5.0, −5.4, −5.5, −5.6, −5.7.

MS (ESI) m/z: 866 (M+18)$^+$.

R$_f$=0.45 (Hex:EtOAc, 4:1).

Example 16

Compound 12e

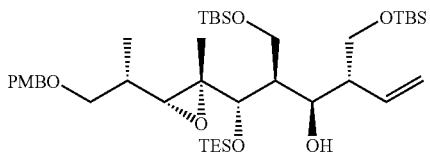

The title compound was prepared as described above in example 12, starting from 11b (0.7 g, 1.09 mmol). Chromatography (SiO$_2$, Hex:EtOAc, 15:1) provided 12e (661 g, 80%) as a colourless oil.

$^1$H NMR (300 MHz, CDCl$_3$) δ 7.22 (d, J=8.7 Hz, 2H), 6.86 (d, J=8.7 Hz, 2H), 5.95-5.82 (m, 1H), 5.13-5.03 (m, 2H), 4.41 (dd, J=15.6, 11.7 Hz, 2H), 4.3, 04.26 (m 1H), 3.86 (dd, J=13.8, 3.6 Hz, 1H), 3.79 (s, 3H), 3.74 (dd, J=10.5, 6.3 Hz, 1H), 3.64 (d, J=5.7 Hz, 1H), 3.61 (d, J=6.3 Hz, 1H), 3.50 (dd, J=9.9, 5.1 Hz, 1H), 3.34 (d, J=7.5 Hz, 2H), 3.18 (d, J=4.8 Hz, 1H), 2.56 (d, J=9.0 Hz, 1H), 2.32-2.23 (m, 1H), 1.85-1.79 (m 1H), 1.74-1.71 (m, 1H), 1.31 (s, 3H), 1.06 (d, J=6.9 Hz, 3H), 0.97 (t, J=7.5 Hz, 9H), 0.89 (s, 9H), 0.88 (s, 9H), 0.68 (q, 7.2, 6H), 0.05 (s, 3H), 0.04 (s, 6H), 0.03 (s, 3H).

$^{13}$C NMR (75 MHz, CDCl$_3$) δ 158.9, 137.6, 130.0, 128.8, 116.6, 113.5, 77.0, 72.6, 72.4, 69.1, 64.7, 64.6, 64.0, 60.2, 54.9, 51.3 46.2, 33.3, 25.7, 25.6, 18.0, 17.7, 14.7, 12.9, 6.7, 4.5, −5.5, −5.7.

MS (ESI) m/z: 775 (M+23)$^+$, 773 (M+1)$^+$.

R$_f$=0.6 (Hex:EtOAc, 4:1).

Example 17

Compound 12f

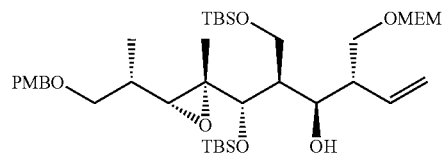

To a solution of 11a (500 mg, 0.78 mmol) in CH$_2$Cl$_2$ (10 mL) was added DIPEA (327 μL, 1.87 mmol) and MEMCl (107 μL, 0.94 mmol) at 0° C. The reaction mixture was stirred at 23° C. for 14 h. Then, the reaction was extracted with HCl 0.1N (10 mL) and the organic layer was dried over Na$_2$SO$_4$, filtered, and concentrated under reduced pressure. The residue was purified by flash column chromatography on silica gel (Hex:EtOAc 10:1) to obtain compound 12f (445 mg, 78%) as a colourless oil.

$^1$H NMR (300 MHz, CDCl$_3$) δ 7.22 (d, J=8.7 Hz, 2H), 6.87 (d, J=8.7 z, 2H), 5.92-5.79 (m, 1H), 5.16-5.09 (m, 2H), 4.67 (s, 2H), 4.42 (dd, J=15.3, 11.7 Hz, 2H), 4.23-4.18 (m, 1H), 4.85 (dd, J=10.5, 4.8 Hz, 1H), 3.80 (s, 3H), 3.67-3.64 (m, 2H), 3.60 (d, J=5.7 Hz, 2H), 3.57-3.51 (m, 2H), 3.49-3.40 (m, 2H), 3.37 (3, 3H), 2.56 (d, J=9.3 Hz, 1H), 2.45-2.40 (m, 1H), 1.85-1.77 (m, 1H), 1.74-1.72 (m, 1H), 1.30 (s, 3H), 1.06 (d, J=6.6 Hz, 3H), 0.91 (s, 9H), 0.87 (s, 9H), 0.15 (s, 3H), 0.09 (s, 3H), 0.05 (s, 3H), 0.04 (s, 3H).

MS (ESI) m/z: 749 (M+23)$^+$.

R$_f$=0.25 (Hex:EtOAc, 4:1).

Example 18

Compound 12 g

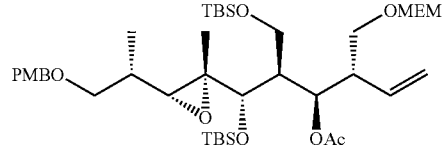

To a solution of 12f (438 mg, 0.6 mmol) in CH$_2$Cl$_2$ (10 mL) was added Et$_3$N (1.67 mL, 12 mmol), DMAP (74 mg, 0.6 mmol) and Ac$_2$O (567 μL, 6 mmol) at 0° C. The reaction mixture was stirred at 23° C. for 12 h. Then, the reaction was extracted with HCl 0.1N (10 mL) and the organic layer was dried over Na$_2$SO$_4$, filtered, and concentrated under reduced pressure. The residue was purified by flash column chromatography on silica gel (Hex:EtOAc 7:1) to obtain compound 12 g (343 mg, 74%) as a colourless oil. $^1$H NMR (300 MHz, CDCl$_3$) δ 7.23 (d, J=8.1 Hz, 2H), 6.87 (d, J=8.7 Hz, 2H), 5.74 (dt, J=19.8, 9.9 Hz, 1H), 5.52-5.49 (m, 1H), 5.13-5.07 (m, 2H), 4.65 (s, 2H), 4.42 (dd, J=13.5, 12.0 Hz, 2H), 3.80 (s, 3H), 3.66-3.62 (m, 2H), 3.60-3.57 (m, 1H), 3.54-3.47 (m, 4H), 3.40-3.34 (m, 1H), 3.38 (s, 3H), 3.28 (d, J=5.7 Hz, 1H), 2.81-2.76 (m, 1H), 2.48 (d, J=8.7 Hz, 1H), 1.97 (s, 3H), 1.83-1.73 (m, 1H), 1.56 (bs, 1H), 1.31 (s, 3H), 1.07 (d, J=6.9 Hz, 3H), 0.91 (s, 9H), 0.88 (s, 9H), 0.12 (s, 3H), 0.06 (s, 3H), 0.03 (s, 6H).

MS (ESI) m/z: 791 (M+23)$^+$.

R$_f$=0.26 (Hex:EtOAc, 4:1).

Example 19

Compound 12h

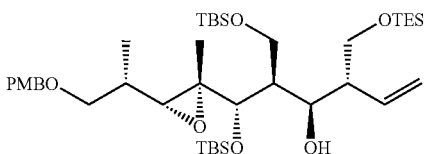

To a solution of 11a (75 mg, 0.117 mmol) in CH$_2$Cl$_2$ (3 mL) was added DIPEA (82 µL, 0.47 mmol) and TESCl (40 µL, 0.234 mmol) at 0° C. The reaction mixture was stirred at 23° C. for 3 h. Then, 0.1N HCl was added until pH=4-5, and the reaction was extracted with CH$_2$Cl$_2$ (2×10 mL). The combined organic layers were dried over Na$_2$SO$_4$, filtered, and concentrated under reduced pressure. The residue was purified by flash column chromatography on silica gel (Hex: EtOAc, 12:1) to obtain compound 12h (77 mg, 87%) as a pale yellow oil.

$^1$H NMR (300 MHz, CDCl$_3$) δ 7.22 (d, J=8.4 Hz, 2H), 6.87 (d, J=8.4 Hz, 2H), 5.94-5.82 (m, 1H), 5.11 (dd, J=9.9, 2.1 Hz, 1H), 5.08 (dd, J=16.8, 2.1 Hz, 1H), 4.41 (dd, J=17.1, 11.7 Hz, 2H), 4.33-4.29 (m, 1H), 3.87 (dd, 1H), 3.80 (s, 3H), 3.65-3.60 (m, 2H), 3.49 (dd, J=9.9, 5.1 Hz, 1H), 3.33 (d, J=6.9 Hz, 2H), 3.24 (d, J=4.5 Hz, 1H), 2.56 (d, J=9.3 Hz, 1H), 2.30-2.25 (m, 1H), 1.82-1.75 (m, 2H), 1.31 (s, 3H), 1.03 (d, J=6.6 Hz, 3H), 0.93-0.90 (r, 9H), 0.92 (s, 9H), 0.87 (s, 9H), 0.57 (q, J=7.8 Hz, 6H), 0.16 (s, 3H), 0.10 (s, 3H), 0.07 (s, 3H), 0.05 (s, 3H).

MS (ESI) m/z: 775 (M+23)$^+$.

R$_f$=0.58 (Hex:EtOAc, 4:1).

Example 20

Compound 12i

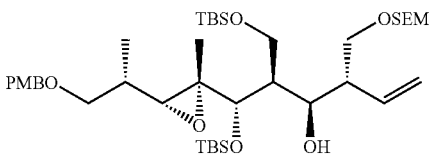

To a solution of 11a (128 mg, 0.2 mmol) in CH$_2$Cl$_2$ (10 mL) was added DIPEA (104 µL, 0.6 mmol), DMAP (2 mg, 0.02 mmol) and SEMCl (53 µL, 0.3 mmol) at 23° C. The reaction mixture was stirred at 23° C. for 6 h. Then, 0.1N HCl was added until pH=4-5, and the reaction was extracted with CH$_2$Cl$_2$ (2×20 mL). The combined organic layers were dried over Na$_2$SO$_4$, filtered, and concentrated under reduced pressure. The residue was purified by flash column chromatography on silica gel (Hex:EtOAc, 10:1) to obtain compound 12i (142 mg, 92%) as a pale yellow oil.

$^1$H NMR (300 MHz, CDCl$_3$) δ 7.22 (d, J=8.5 Hz, 2H), 6.86 (d, J=8.5 Hz, 2H), 5.79-5.88 (m, 1H), 5.10-5.17 (m, 2H), 4.61 (s, 2H), 4.42 (dd, J=15.9, 11.5 Hz, 2H), 4.17-4.22 (m, 1H), 3.76-3.87 (m, 1H), 3.79 (s, 3H), 3.42-3.62 (m, 3H), 3.36 (d, J=6.8 Hz, 1H), 2.56 (d, J=9.3 Hz, 1H), 2.40-2.45 (m, 1H), 1.72-1.83 (m, 2H), 1.25 (s, 3H), 1.06 (d, J=6.6 Hz, 3H), 0.91 (s, 9H), 0.87 (s, 9H), 0.15 (s, 3H), 0.09 (s, 3H), 0.05 (s, 3H), 0.04 (s, 3H), 0.00 (s, 9H). $^{13}$C-NMR (75 MHz, CDCl3): δ 159.4, 137.8, 130.4, 129.3, 117.4, 114.0, 95.2, 73.1, 72.8, 70.3, 69.4, 65.3, 64.8, 64.2, 60.6, 55.4, 49.2, 47.0, 33.8, 29.9, 26.3, 26.0, 18.5, 18.3, 18.1, 15.1, 13.7, −1.2, −4.2, −5.1, −5.2.

MS (ESI) m/z: 792 (M+23)$^+$.

R$_f$=0.56 (Hex:EtOAc, 4:1).

Example 21

Compound 12j

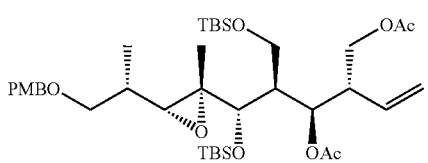

To a solution of 11a (600 mg, 0.93 mmol) in CH$_2$Cl$_2$ (10 mL) was added Et$_3$N (2.61 mL, 18.76 mmol), DMAP (115 mg, 0.93 mmol) and Ac$_2$O (887 µL, 9.39 mmol) at 0° C. The reaction mixture was stirred at 23° C. for 3 h. Then, 0.1N HCl was added until pH=4-5, and the reaction was extracted with CH$_2$Cl$_2$ (2×20 mL). The combined organic layers were dried over Na$_2$SO$_4$, filtered, and concentrated under reduced pressure. The residue was purified by flash column chromatography on silica gel (Hex:EtOAc, from 10:1 to 5:1) to obtain compound 12j (592 mg, 87%) as a pale yellow oil.

$^1$H NMR (300 MHz, CDCl$_3$) δ 7.22 (d, J=8.7 Hz, 2H), 6.87 (d, J=8.7 Hz, 2H), 5.72-5.60 (m, 1H), 5.53-5.50 (m, 1H), 5.16-5.07 (m, 2H), 4.42 (s, 2H), 4.03 (dd, J=11.1, 6.3 Hz, 1H), 3.90 (dd, J=11.1, 6.9 Hz, 1H), 3.80 (s, 3H), 3.58 (dd, J=10.2, 5.7 Hz, 1H), 3.47 (dd, J=10.2, 6.3 Hz, 1H), 3.38-3.34 (m, 3H), 2.88-2.83 (m, 1H), 2.48 (d, J=9.3 Hz, 1H), 2.01 (s, 3H), 1.98 (s, 3H), 1.95-1.90 (m, 1H), 1.83-1.74 (m, 1H), 1.32 (s, 3H), 1.06 (d, J=6.6 Hz, 3H), 0.88 (s, 9H), 0.87 (s, 9H), 0.12 (s, 3H), 0.06 (s, 3H), 0.03 (s, 3H), 0.02 (s, 3H).

MS (ESI) m/z: 745 (M+23)$^+$.

R$_f$=0.34 (Hex:EtOAc, 4:1).

Example 22

Compound 12k

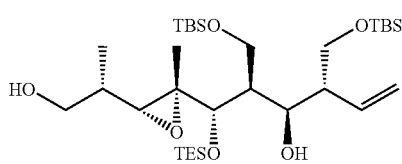

To a solution of crude 12e (545 mg, 0.73 mmol) in a mixture of CH$_2$Cl$_2$:H$_2$O (8:0.4 mL) was added 2,3-dichloro-5,6-dicyano-1,4-benzoquinone (329 mg, 1.45 mmol) at 23° C. The reaction mixture was stirred at 23° C. for 45 min. Saturated aqueous solution of NaHCO$_3$ (30 mL) was added and the mixture was extracted with CH$_2$Cl$_2$ (3×40 mL). The combined organic layers were dried over Na$_2$SO$_4$, filtered, and concentrated under reduced pressure. The residue was solved in MeOH and NaBH$_4$ (70 mg, 1.9 mmol) was added. The mixture was stirred at 23° C. for 2 h and then, the reaction was concentrated under reduced pressure. A saturated aqueous solution of NaHCO$_3$ (20 mL) was added and the mixture was extracted with CH$_2$Cl (3×30 mL). The combined organic layers were dried over Na$_2$SO$_4$, filtered, and concentrated under reduced pressure. The residue was purified by flash column chromatography on silica gel (Hex:EtOAc, 10:1) to obtain 12k (300 mg, 65%) as a pale yellow oil.

$^1$H NMR (300 MHz, CDCl$_3$) δ 5.88-5.80 (m, 1H), 5.15-5.09 (m, 2H), 4.18.4.17 (m, 1H), 3.92 (dd, J=10.5, 4.5 Hz, 1H), 3.86-3.68 (m, 1H), 3.66-3.56 (m, 3H), 3.50-3.47 (m, 1H), 3.33 (d, J=3.9, 1H), 2.54 (d, J=9.3 Hz, 1H), 2.38-2.34 (m, 1H), 1.87-1.86 (m, 1H), 1.71-1.62 (m, 1H), 1.33 (s, 3H), 1.03 (d, J=6.9 Hz, 3H), 0.95 (t, J=8.1 Hz, 9H), 0.87 (s, 9H), 0.87 (s, 9H), 0.67 (q, J=8.4 Hz, 6H), 0.05 (s, 3H), 0.04 (s, 3H), 0.03 (s, 3H), 0.02 (s, 3H).

MS (ESI) m/z: 655 (M+23)$^+$, 633 (M+1)$^+$.

R$_f$=0.38 (Hex:EtOAc, 4:1).

Example 23

Compound 12l

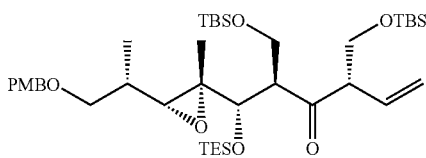

To a solution of 12e (100 mg, 0.13 mmol) in CH$_2$Cl$_2$ (6 mL) was added Dess-Martin periodinane (113 mg, 0.26 mmol) and catalytic amount of NaHCO$_3$ at 23° C. The reaction mixture was stirred at 23° C. for 2 h. Saturated aqueous solution of NaHCO$_3$ (10 mL) was added and the mixture was extracted with CH$_2$Cl$_2$ (3×10 mL). The combined organic layers were dried over Na$_2$SO$_4$, filtered, and concentrated under reduced pressure. The residue was purified by flash column chromatography on silica gel (Hex:EtOAc, 20:1) to obtain 12l (110 mg, 96%) as a pale yellow oil.

$^1$H NMR (300 MHz, CDCl$_3$) δ 7.27 (d, J=8.7 Hz, 2H), 6.90 (d, J=8.7 Hz, 2H), 5.78 (ddd, J=16.8, 10.2, 9.0 Hz, 1H), 5.29-5.22 (m, 2H), 4.43 (q, J=11.4 Hz, 2H), 4.04 (dd, J=10.2, 4.2 Hz, 1H), 3.84 (s, 3H), 3.77-3.72 (m, 1H), 3.66-3.60 (m, 2H), 3.45-3.30 (m, 5H), 2.50 (d, J=9.3 Hz, 1H), 1.85-1.75 (m, 1H), 1.32 (s, 3H), 1.09 (d, J=6.6 Hz, 1H), 0.95 (t, J=7.8 Hz, 9H), 0.91 (s, 9H), 0.87 (s, 9H), 0.63 (q, J=7.8 Hz, 6H), 0.08 (s, 3H), 0.07 (s, 3H), 0.01 (s, 3H), 0.00 (s, 3H).

$^{13}$C NMR (75 MHz, CDCl$_3$) δ 209.9, 159.1, 134.3, 130.2, 129.0, 119.3, 113.7, 78.0, 72.3, 72.1, 64.8, 63.0, 62.6, 62.3, 61.1, 56.1, 55.2, 33.6, 29.7, 25.9, 25.8, 18.2, 18.1, 15.1, 11.9, 6.8, 4.6, −5.3, −5.4, −5.5.

MS (ESI) m/z: 773 (M+23)$^+$.

R$_f$=0.57 (Hex:EtOAc, 4:1).

Example 24

Compound 12m

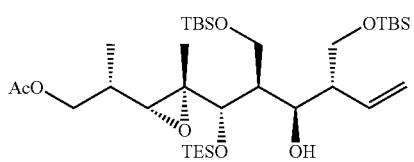

To a solution of 12k (280 mg, 0.44 mmol) in THF (5 mL) was added E$_3$N (368 μL, 2.64 mmol), DMAP (5 mg, 0.04 mmol) and Ac$_2$O, (125 μL, 1.32 mmol) at 0° C. The reaction mixture was stirred at 23° C. for 1 h. Then, 0.1N HCl was added until pH=4-5, and the reaction was extracted with CH$_2$Cl$_2$ (2×10 mL). The combined organic layers were dried over Na$_2$SO$_4$, filtered, and concentrated under reduced pressure. The residue was purified by flash column chromatography on silica gel (Hex:EtOAc, 15:1) to obtain compound 12m (258 mg, 87%) as a pale yellow oil.

$^1$H NMR (300 MHz, CDCl$_3$) δ 5.90 (ddd, J=17.1, 10.8, 9.6 Hz, 1H), 5.16-5.09 (m, 2H), 4.32-4.28 (m, 1H), 4.09 (dd, J=11.1, 5.7 Hz, 1H), 3.89-3.76 (m, 3H), 3.70-3.67 (m, 2H), 3.56 (dd, J=9.9, 5.1 Hz, 1H), 3.08, (d, J=4.5 Hz, 1H), 2.57 (d, J=9.3 Hz, 1H), 2.40-2.31 (m, 1H), 2.05 (s, 3H), 1.30 (s, 3H), 1.10 (d, J=6.9 Hz, 3H), 0.96 (t, J=8.1 Hz, 9H), 0.88 (s, 9H), 0.87 (s, 9H), 0.69 (q, J=8.1 Hz, 6H), 0.05 (s, 3H), 0.03 (s, 6H), 0.02 (s, 3H).

R$_f$=0.66 (Hex:EtOAc, 4:1).

Example 25

Compound 12n

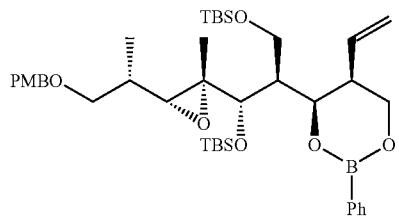

To a solution of 11a (110 mg, 0.17 mmol) in CH$_2$Cl$_2$ (5 mL) was added PhB(OH)$_2$ (33 mg, 0.26 mmol) and the reaction mixture was stirred at 23° C. for 1 h. Then, the solution was filtered through a pad of celite. The filtrate was dried over Na$_2$SO$_4$, filtered, and concentrated under reduced pressure. The residue was purified by flash column chromatography on silica gel (Hex:EtOAc, from 20:1 to 10:1) to obtain compound 12n (94 mg, 75%) as a pale yellow oil.

$^1$H NMR (300 MHz, CDCl$_3$) δ 7.81 (dd, J=7.8, 1.2 Hz, 2H), 7.65-7.60 (m, 1H), 7.56-7.42 (m, 2H), 7.24 (d, J=8.7 Hz, 2H), 6.83 (d, J=8.7 Hz, 2 Hz), 5.88 (ddd, J=18.9, 10.2, 8.7 Hz, 1H), 5.23-5.17 (m, 2H), 4.54 (dd, J=6.6, 2.4 Hz, 1H), 4.39 (dd, J=18.0, 11.1 Hz, 2H), 4.27 (dd, J=11.1, 3.3 Hz, 1H), 4.03 (brd, J=0.5 Hz, 1H), 3.97 (dd, J=10.2, 6.3 Hz, 1H), 3.82 (d, J=5.1 Hz, 1H), 3.68 (s, 3H), 3.65 (dd, J=10.5, 3.6 Hz, 1H), 3.46-3.35 (m, 2H), 2.87 (brd, J=8.4 Hz, 1H), 2.70 (d, J=9.3 Hz, 1H), 1.93-1.83 (m, 2H), 1.30 (s, 3H), 1.11 (d, J=6.6 Hz, 3H), 0.95 (s, 9H), 0.92 (s, 9H), 0.18 (s, 3H), 0.14 (s, 3H), 0.08 (s, 3H), 0.07 (s, 3H).

R$_f$=0.46 (Hex:EtOAc, 4:1).

Example 26

Compound 12o

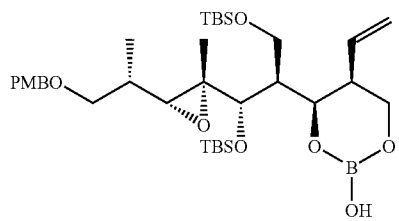

The title compound was obtained as precursor of 11a in the reduction reaction of 10a before the treatment with H$_2$O$_2$. $^1$H NMR (300 MHz, CDCl$_3$) δ 7.20 (d, J=8.4 Hz, 2H), 6.85 (d, J=8.4 Hz, 2H), 5.87-5.79 (m, 1H), 5.22-5.17 (m, 2H), 4.38 (dd, J=10.8 Hz, 13.2 Hz, 2H), 4.30 (dd J=6.6, 2.7 Hz, 1H), 4.07 (dd, J=10.8, 3.0 Hz, 1H), 3.83-3.72 (m, 2H), 3.80 (s, 3H), 3.69 (d, J=5.1 Hz, 1H), 3.50 (dd, J=9.9, 3.0 Hz, 1H), 3.37-3.32

(m, 2H), 2.67 (brd, J=8.4 Hz, 1H), 2.62 (d, J=9.3 Hz, 1H), 1.81-1.76 (m, 2H), 1.21 (s, 3H), 1.06 (d, J=6.9 Hz, 3H), 0.91 (s, 9H), 0.89 (s, 9H), 0.12 (s, 3H), 0.05 (s, 3H), 0.03 (s, 3H), 0.02 (s, 3H).

$^{13}$C NMR (75 MHz, CDCl$_3$) δ 159.1, 134.0, 130.2, 129.1, 118.4, 113.7, 76.2, 72.9, 70.0, 67.1, 64.8, 59.5, 55.2, 45.7, 43.9, 33.4, 26.4, 26.0, 25.9, 25.5, 18.2, 14.9, 14.0, 13.3, −4.3, −4.9, −5.3, −5.4.

MS (ESI) m/z: 661 (M+23)$^+$.

R$_f$=0.50 (Hex:EtOAc, 4:1).

Example 27

Compound 12p

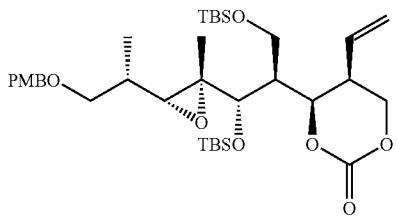

To a solution of 11a (119 mg, 0.18 mmol) in THF (10 mL) was added CDI (49 mg, 0.3 mmol) and NaH (8 mg, 0.2 mmol) and the reaction mixture was stirred at 23° C. for 3 h. Then, a saturated aqueous solution of NaHCO$_3$ (10 mL) was added and the mixture was extracted with CH$_2$Cl$_2$ (3×10 mL). The combined organic layers were dried over Na$_2$SO$_4$, filtered, and concentrated under reduced pressure. The residue was purified by flash column chromatography on silica gel (Hex:EtOAc, 5:1) to obtain 12 p (97 mg, 78%) as a pale yellow oil.

$^1$H NMR (300 MHz, CDCl$_3$) δ 7.19 (d, J=8.4 Hz, 2H), 6.87 (d, J=8.4 Hz, 2H), 5.79-5.70 (m, 1H), 5.32-5.26 (m, 2H), 4.67 (dd, J=7.5, 2.4 Hz, 1H), 4.43 (dd, J=10.5, 3.6 Hz, 1H), 4.35 (q, J=10.2 Hz, 2H), 4.25 (dd, J=16.2, 15.3 Hz, 2H), 3.80 (s, 3H), 3.77-3.69 (m, 2H), 3.54 (dd, J=10.5, 3.0 Hz, 1H), 3.42 (dd, J=9.3, 4.8 Hz, 1H), 3.30 (t, J=9.3 Hz, 1H), 2.92 (br d, J=8.4 Hz, 1H), 2.66 (d, J=9.6 Hz, 1H), 1.95-1.92 (m, 1H), 1.21 (s, 3H), 1.05 (d, J=6.9 Hz, 3H), 0.89 (s, 9H), 0.88 (s, 9H), 0.11 (s, 3H), 0.07 (s, 6H), 0.05 (s, 3H).

$^{13}$C NMR (75 MHz, CDCl$_3$) δ 173.8, 159.4, 154.1, 130.5, 129.4, 114.0, 99.3, 76.5, 73.0, 72.6, 68.0, 66.0, 64.7, 64.6, 63.6, 61.2, 59.5, 58.8, 55.4, 44.5, 42.1, 41.6, 33.7, 29.7, 28.8, 26.3, 26.3, 26.2, 26.1, 19.0, 18.6, 18.3, 18.2, 15.2, 14.9, 13.7, −4.1, −4.2, −5.1, −5.2.

MS (ESI) m/z: 687 (M+23)$^+$.

R$_f$=0.47 (Hex:EtOAc, 4:1).

Example 28

Compound 12q

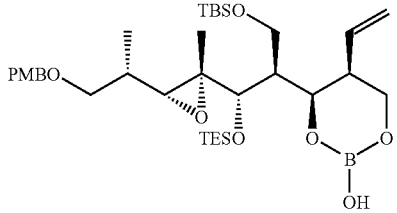

The title compound was obtained as precursor of 11 b in the reduction reaction of 10 b before the treatment with H$_2$O$_2$. $^1$H NMR (300 MHz, CDCl$_3$) δ 7.16 (d, J=8.4 Hz, 2H), 6.82 (d, J=8.7 Hz, 2H), 5.86-5.74 (m, 1H), 5.20-5.15 (m, 2H), 4.40-4.34 (m, 2H), 4.18-4.15 (m, 1H), 4.09-4.03 (m, 1H), 3.85-3.79 (m, 1H), 3.76 (s, 3H), 3.66 (d, J=7.8 Hz, 1H), 3.58 (q, J=7.2 Hz, 1H), 3.47 (dd, J=9.9, 2.4 Hz, 1H), 3.37-3.27 (m, 1H), 2.87 (br d, J=8.7 Hz, 1H), 2.74 (q, J=7.5 Hz, 1H), 2.63 (d, J=9.3 Hz, 1H), 1.72-1.65 (m, 2H), 1.18 (s, 3H), 1.03 (d, J=6.3 Hz, 3H), 0.91-0.85 (m, 9H), 0.84 (s, 9H), 0.60 (q, J=7.8 Hz, 6H), −0.01 (s, 3H), −0.02 (s, 3H).

R$_f$=0.65 (Hex:EtOAc, 4:1).

Example 29

Compound 13a

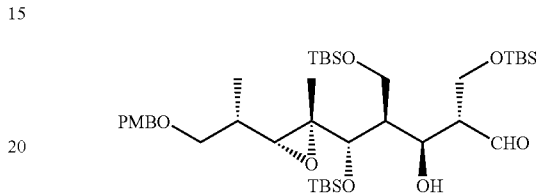

Over a solution of 12a (5.91 g, 7.85 mmol) in CH$_2$Cl$_2$ (80 mL) was bubbled a current of O$_3$ during 15 min at −78° C. Then, Ph$_3$P (6.29 g, 24 mmol) was added and the mixture was allowed to warm to room temperature, and the stirring was continued for 12 h. The mixture was concentrated under reduced pressure and the residue was purified by flash column chromatography on silica gel (Hex:EtOAc, 20:1) to afford compound 13a (4.99 g, 84%) as a white solid. $^1$H NMR (300 MHz, CDCl$_3$) δ 9.80 (d, J=3.0 Hz, 1H), 7.20 (d, J=8.7 Hz, 2H), 6.85 (d, J=8.7 Hz, 2H), 4.66 (m, 1H), 0.439 (s, 2H), 3.84 (m, 2H), 3.78 (s, 3H), 3.68 (m, 2H), 3.61 (m, 2H), 3.37 (m, 2H), 2.58 (d, J=9.0 Hz, 1H), 2.44 (m, 1H), 1.82 (m, 1H), 1.72 (m, 1H), 1.29 (s, 3H), 1.05 (d, J=6.6 Hz, 3H), 0.91 (s, 9H), 0.87 (s, 9H), 0.85 (s, 9H), 0.15 (s, 3H), 0.11 (s, 3H), 0.06 (s, 6H), 0.00 (s, 6H).

$^{13}$C NMR (75 MHz, CDCl$_3$) δ 205.3, 159.2, 130.0, 129.0, 113.7, 76.4, 72.8, 72.7, 67.9, 64.6, 63.9, 60.8, 60.1, 57.7, 55.1, 44.4, 33.5, 26.1, 25.7, 18.3, 18.1, 17.8, 14.8, 12.9, −4.6, −5.3, −5.5, −5.5, −5.7, −5.7.

[α]$^{25}_D$+2.3 (c 0.50, CH$_2$Cl$_2$).

R$_f$=0.46 (Hex:EtOAc, 4:1).

Example 30

Compound 13b

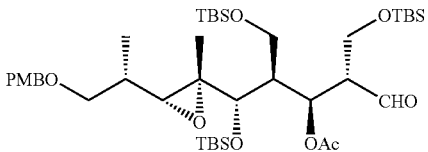

To a solution of 12c (2.25 g, 2.84 mmol) in THF:H$_2$O (70:30, 105 mL) was added NMO (1.16 g, 9.94 mmol) and OsO$_4$ (5.68 mL, 0.568 mmol, 0.1 M in $^t$BuOH) at 23° C. and the reaction mixture was stirred at 23° C. overnight. Florisil (16 g), NaHSO$_3$ (16 g), and EtOAc (160 mL) were added and the mixture was stirred vigorously during 30 min. The mixture was filtered through a pad of Celite, and the filtrate was concentrated to provide the corresponding diol. This diol was dissolved in anhydrous Toluene (50 mL) and Pb(OAc)$_4$ (1.57 g, 3.55 mmol) was added at 0° C., stirred for 30 min, filtered through a pad of Celite, washed with EtOAc and concentrated under reduced pressure. The residue was purified by flash column chromatography on silica gel (Hex:EtOAc, 20:1) to afford compound 13b (0.97 g, 43%) as a colourless oil.

$^{1}$H NMR (300 MHz, CDCl$_{3}$) δ 9.61 (d, J=3.9 Hz, 1H), 7.22 (d, J=8.5 Hz, 2H), 6.87 (d, J=8.5 Hz, 2H), 5.56 (dd, J=10.3, 6.6 Hz, 1H), 4.42 (s, 2H), 3.95 (m, 1H), 3.80 (s, 3H), 3.54 (m, 2H), 3.38 (d, J=7.0 Hz, 2H), 3.24 (d, J=6.8 Hz, 1H), 3.04 (m, 1H), 2.49 (d, J=9.0 Hz, 1H), 1.98 (s, 3H), 1.79 (m, 1H), 1.31 (s, 3H), 1.06 (d, J=6.8 Hz, 3H), 0.92 (s, 9H), 0.88 (s, 9H), 0.85 (s, 9H), 0.13 (s, 3H), 0.06 (s, 6H), 0.04 (s, 3H), 0.03 (s, 6H).

$^{13}$C NMR (75 MHz, CDCl$_{3}$) δ 203.3, 170.1, 159.4, 130.4, 129.3, 114.0, 76.6, 73.1, 72.7, 69.1, 64.4, 63.9, 61.3, 60.0, 58.4, 55.4, 46.4, 33.4, 29.9, 26.4, 26.1, 26.0, 21.2, 18.6, 18.4, 18.3, 15.1, 12.8, −4.1, −5.0, −5.1, −5.2, −5.3, −5.4.

MS (ESI) m/z: 819 (M+23)$^{+}$.

R$_{f}$=0.47 (Hex:EtOAc, 4:1).

Example 31

Compound 13c

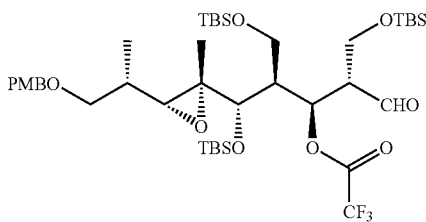

To a solution of 13a (90 mg, 0.12 mmol) in CH$_{2}$Cl$_{2}$ (10 mL) was added Py (0.19 mL, 2.4 mmol), DMAP (22 mg, 0.18 mmol) and (CF$_{3}$CO)$_{2}$O (0.17 mL, 1.2 mmol) at 0° C. and the reaction mixture was stirred at 0° C. for 2 h. Then, the reaction was concentrated under reduced pressure to obtain 13c which was used in subsequent steps with no further purification. $^{1}$H NMR (300 MHz, CDCl$_{3}$) δ 9.63 (d, J=2.4 Hz, 1H), 7.19 (d, J=8.6 Hz, 2H), 6.85 (d, J=8.6 Hz, 2H), 5.75-5.79 (m, 1H), 4.34-4.42 (m, 2H), 3.86-3.90 (m, 2H), 3.78 (s, 3H), 3.48 (d, J=5.4 Hz, 1H), 3.30-3.38 (m, 3H), 3.08-3.13 (m, 1H), 2.51 (d, J=9.0 Hz, 1H), 2.21-2.27 (m, 1H), 1.77-1.82 (m, 1H), 1.25 (s, 3H), 1.05 (d, J=6.8 Hz, 3H), 0.91 (s, 9H), 0.86 (s, 9H), 0.85 (s, 9H), 0.13 (s, 3H), 0.07 (s, 3H), 0.06 (s, 3H), 0.02 (s, 6H), 0.00 (s, 3H).

R$_{f}$=0.70 (Hex:EtOAc, 4:1).

Example 32

Compound 13d

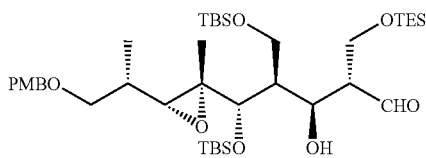

Following the procedure described in example 29, 12h (1 g, 1.32 mol) was converted to 13d (715 mg, 72%, colourless oil) after purification of the crude product by flash column chromatography (Hex:EtOAc, 20:1).

$^{1}$H NMR (300 MHz, CDCl$_{3}$) δ 9.81 (d, J=3.0 Hz, 1H), 7.21 (d, J=8.7 Hz, 2H), 6.86 (d, J=8.4 Hz, 2H), 4.70-4.64 (m, 1H), 4.40 (s, 2H), 3.89-3.81 (m, 1H), 3.80 (s, 3H), 3.75-3.66 (m, 2H), 3.64 (d, J=6.6 Hz, 2H), 3.38-3.35 (m, 2H), 2.60 (d, J=9.3 Hz, 1H), 2.50-2.46 (m, 1H), 1.85-1.80 (m, 1H), 1.77-1.68 (m, 1H), 1.29 (s, 3H), 1.06 (d, J=6.6 Hz, 3H), 0.94-087 (m, 9H), 0.92 (s, 9H), 0.87 (s, 9H), 0.55 (q, J=7.8 Hz, 6H), 0.16 (s, 3H), 0.11 (s, 3H), 0.07 (s, 3H), 0.06 (s, 3H).

MS (ESI) m/z: 777 (M+23)$^{+}$.

R$_{f}$=0.5 (Hex:EtOAc, 4:1).

Example 33

Compound 13e

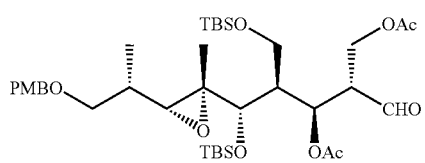

Following the procedure described in example 29, 12j (590 mg, 0.81 mol) was converted to 13e (420 mg, 71%, pale yellow oil) after purification of the crude product by flash column chromatography (Hex:EtOAc, 10:1).

$^{1}$H NMR (300 MHz, CDCl$_{3}$) δ 9.58 (d, J=20.0 Hz, 1H), 7.19 (d, J=8.4 Hz, 2H), 6.82 (d, J=8.4 Hz, 2H), 5.58 (dd, J=5.1, 4.6 Hz, 1H), 4.38 (s, 2H), 4.30-4.23 (m, 2H), 3.76 (s, 3H), 3.50 (dd, J=6.9, 5.1 Hz, 2H), 3.30 (d, J=7.0 Hz, 2H), 3.25-3.22 (m, 2H), 2.44 (d, J=9.3 Hz, 1H), 2.15-2.12 (m, 1H), 1.93 (s, 3H), 1.92 (s, 3H), 1.23 (s, 3H), 1.12 (d, J=6.6 Hz, 3H), 0.84 (s, 9H), 0.82 (s, 9H), 0.09 (s, 3H), 0.02 (s, 3H), 0.01 (s, 3H), 0.00 (s, 3H).

R$_{f}$=0.26 (Hex:EtOAc, 4:1).

Example 34

Compound 13f

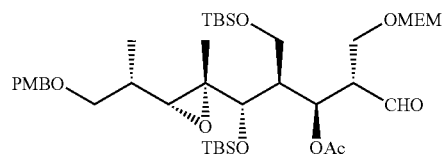

Following the procedure described in example 29, 12 g (342 mg, 0.44 mol) was converted to 13f (306 mg, 90%, pale yellow oil) after purification of the crude product by flash column chromatography (Hex:EtOAc from 4:1 to 0:1).

$^{1}$H NMR (300 MHz, CDCl$_{3}$) δ 9.64 (d, J=3.3 Hz, 1H), 7.22 (d, J=8.1 Hz, 2H), 6.86 (d, J=8.4 Hz, 2H), 5.64 (dd, J=6.6, 3.9 Hz, 1H), 4.63 (s, 2H), 4.40 (s, 2H), 3.86 (dd, J=9.9, 7.5 Hz, 1H), 3.79 (s, 3H), 3.74 (dd, J=10.2, 4.5 Hz, 1H), 3.65-3.61 (m, 2H), 3.53-3.50 (m, 4H), 3.85-3.34 (m, 1H), 3.37 (s, 3H), 3.21 (d, J=7.2 Hz, 1H), 3.15-3.13 (m, 1H), 2.48 (d, J=9.0 Hz, 1H), 1.98 (s, 3H), 1.80-1.75 (m, 1H), 1.28 (s, 3H), 1.05 (d, J=6.9 Hz, 3H), 0.90 (s, 9H), 0.87 (s, 9H), 0.11 (s, 3H), 0.05 (s, 3H), 0.04 (s, 3H), 0.03 (s, 3H).

MS (ESI) m/z: 793 (M+23)$^{+}$.

R$_{f}$=0.1 (Hex:EtOAc, 4:1).

Example 35

Compound 13 g

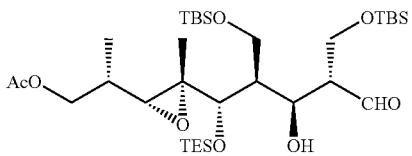

Following the procedure described in example 29, 12 m (200 mg, 0.3 mmol) was converted to 13 g (173 mg, 86%, pale yellow oil) after purification of the crude product by flash column chromatography (Hex:EtOAc, 15:1).

$^1$H NMR (300 MHz, CDCl$_3$) δ 9.84 (d, J=2.7 Hz, 1H), 4.67-4.61 (m, 1H), 4.08 (dd, J=11.1, 5.7 Hz, 1H), 3.95-3.84 (m, 3H), 3.81 (d, J=5.1 Hz, 2H), 3.70 (d, J=6.9 Hz, 1H), 3.47 (d. J=5.4 Hz, 1H), 2.64-2.61 (m, 1H), 2.26 (d, J=9.3 Hz, 1H), 2.04 (s, 3H), 1.85-1.80 (m, 1H), 1.30 (s, 3H), 1.11 (d, J=6.6 Hz, 3H), 0.96 (t, J=8.1 Hz, 9H), 0.87 (s, 9H), 0.85 (s, 9H), 0.68 (q, J=8.1 Hz, 6H), 0.07 (s, 3H), 0.06 (s, 3H), 0.03 (s, 6H).
MS (ESI) m/z: 699 (M+23)$^+$, 677 (M+1)$^+$.
R$_f$=0.52 (Hex:EtOAc, 4:1).

Example 36

Compounds 14a and 14b

To a solution of N-methoxy-N-methylacetamide (0.8 mL g, 7.56 mmol) in THF (2 mL) at −78° C. was added bis-(trimethylsilyl)-lithiumamide (7.56 mL, 1.0 M in THF, 7.56 mmol) and the reaction mixture was stirred for 1 h at −78° C. Then, a solution of 13a (1.61 g, 2.13 mmol) in THF (10 mL) was added over the previous solution and the reaction mixture was stirred for an additional 1 h at −78° C. Then, a saturated aqueous solution of NH$_4$Cl (50 mL) was added and the reaction was extracted with EtOAc (3×60 mL). The combined organic layers were dried over Na$_2$SO$_4$, filtered, and concentrated under reduced pressure. The residue was purified by flash column chromatography on silica gel (Hex:EtOAc from 4:1 to 2:1) to yield 14a and 14b (25:75) as colourless oils (1.67 g, in a combined 91% of yield).

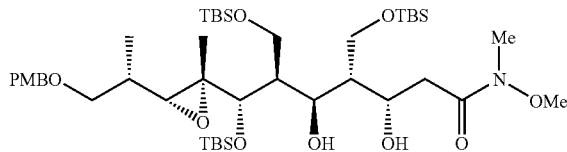

14a: $^1$H NMR (300 MHz, CDCl$_3$) δ 7.20 (d, J=8.7 Hz, 2H), 6.85 (d, J=8.7 Hz, 2H), 4.46-4.43 (m, 1H), 4.39 (s, 2H), 4.33 (m, 1H), 4.14 (d, J=7.2 Hz, 1H), 3.92-3.88 (m, 2H), 3.83 (d, J=3.6 Hz, 1H), 3.78 (s, 3H), 3.63 (s, 3H), 3.61-3.57 (m, 3H), 3.41-3.30 (m, 2H), 3.17 (s, 3H), 3.0-2.91 (m, 1H), 2.63-2.62 (m, 1H), 2.58 (d, J=9.0 Hz, 1H), 2.02-1.96 (m, 1H), 1.85-1.78 (m, 1H), 1.75-1.72 (m, 1H), 1.27 (s, 3H), 1.06 (d, J=6.6 Hz, 3H), 0.91 (s, 9H), 0.86 (s, 18H), 0.14 (s, 3H), 0.11 (s, 3H), 0.08 (s, 3H), 0.05 (s, 3H), 0.02 (s, 3H), 0.01 (s, 3H).
$^{13}$C NMR (75 MHz, CDCl$_3$) δ 173.8, 159.4, 130.3, 129.3, 114.0, 76.3, 73.0, 72.6, 70.4, 70.1, 64.8, 64.0, 61.9, 61.4, 60.6, 55.4, 47.9, 44.4, 36.9, 34.0, 32.1, 29.9, 26.5, 26.4, 26.1, 26.0, 18.6, 18.3, 18.0, 15.3, 12.8, −4.3, −5.0, −5.1, −5.2, −5.4.
MS (ESI) m/z: 858 (M+1)$^+$.
[α]$^{25}$$_D$−10.7 (c 0.5, CH$_2$Cl$_2$).

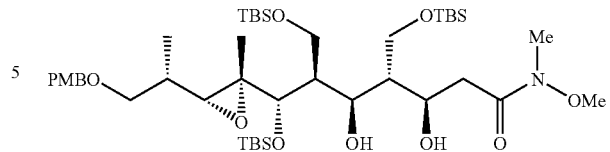

14b: $^1$H NMR (300 MHz, CDCl$_3$) δ 7.17 (d, J=8.4 Hz, 2H), 6.83 (d, J=8.4 Hz, 2H), 4.52-4.51 (m, 1H), 4.45 (s, 3H), 4.37 (s, 2H), 4.28-4.23 (m, 1H), 3.91-3.88 (m, 1H), 3.81 (m, 1H), 3.76 (s, 3H), 3.64 (s, 3H), 3.61-3.52 (m, 3H), 3.48-3.43 (dd, J=10.5, 3.3 Hz, 1H), 3.38-3.35 (m, 2H), 3.15 (s, 3H), 2.84-2.79 (m, 1H), 2.57 (d, J=9.0 Hz, 1H), 1.94-1.92 (m, 1H), 1.83-1.81 (m, 1H), 1.72-1.69 (m, 1H), 1.24 (s, 3H), 1.05 (d, J=6.3 Hz, 3H), 0.89 (s, 9H), 0.86 (s, 9H), 0.85 (s, 9H), 0.13 (s, 3H), 0.08 (s, 3H), 0.07 (s, 3H), 0.04 (s, 3H), 0.01 (s, 3H), −0.01 (s, 3H).
$^{13}$C NMR (75 MHz, CDCl$_3$) δ 174.8, 159.4, 130.3, 129.2, 113.9, 76.4, 73.0, 72.8, 69.2, 68.5, 64.9, 64.1, 61.4, 60.8, 60.1, 55.4, 47.8, 43.7, 34.1, 26.5, 26.3, 26.2, 26.1, 26.0, 25.9, 18.7, 18.2, 17.9, 15.2, 12.7, −4.6, 4.9, −5.0, −5.2, −5.4, −5.5.
MS (ESI) m/z: 880 (M+23)$^+$, 858 (M+1)$^+$.
[α]$^{25}$$_D$+12.8 (c 0.50, CH$_2$Cl$_2$).
R$_f$ 0.44 (Hex:EtOAc, 2:1).

Example 37

Compounds 14c and 14d

To a solution of benzyl acetate (38 μL, 0.53 mmol) in dry THF (5 mL) at −78° C. was added lithium bis(trimethylsilyl) amide (264 μL, 1.0 M in THF, 0.264 mmol) and the reaction mixture was stirred for 1 h at −78° C. Then, a solution of 13a (150 mg, 0.17 mmol) in THF (5 mL) was added over the previous solution and the reaction mixture was stirred for 5 h at −78° C. Then, a saturated aqueous solution of NH$_4$Cl (30 mL) was added and the crude reaction was extracted with EtOAc (3×50 mL). The combined organic layers were dried over Na$_2$SO$_4$, filtered and concentrated in vacuo. The residue was purified by flash column chromatography on silica gel (Hex:EtOAc from 20:1 to 5:1) to yield 14c (34 mg, 20%) and 14d (77 mg, 44%) as colourless oils.

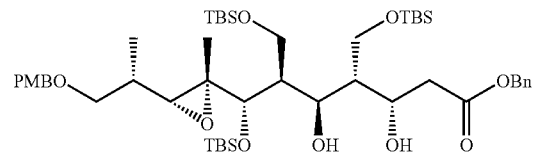

14c: $^1$H NMR (300 MHz, CDCl$_3$) δ 7.28-7.39 (m, 5H), 7.19 (d, J=8.7 Hz, 2H), 6.82 (d, J=8.7 Hz, 2H), 5.20 (s, 2H), 5.17 (s, 2H), 4.58-4.64 (m, 1H), 4.38 (s, 2H), 3.78 (s, 3H), 3.58-3.82 (m, 4H), 3.50 (s, 2H), 3.28-3.41 (m, 3H), 2.60 (dd, J=15.0 and 9.6 Hz, 1H), 2.53 (d, J=9.3 Hz, 1H), 2.25 (dd, J=153, 4.7 Hz, 1H), 1.76-1.86 (m, 1H), 1.59-1.62 (m, 1H), 1.26 (s, 3H), 1.05 (d, J=6.6 Hz, 3H), 0.91 (s, 9H), 0.88 (s, 9H), 0.17 (s, 3H), 0.11 (s, 3H), 0.05 (s, 3H), 0.04 (s, 3H).
R$_f$=0.33 (Hex:EtOAc, 4:1).

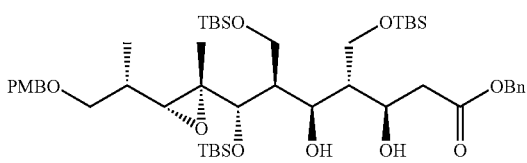

14d: $^1$H NMR (300 MHz, CDCl$_3$) δ 7.32-7.55 (m, 5H), 7.20 (d, J=8.7 Hz, 2H), 6.84 (d, J=8.7 Hz, 2H), 5.19 (s, 2H), 4.43-4.48 (m, 1H), 4.40 (s, 2H), 4.32-4.40 (m, 1H), 4.19-4.23 (m, 1H), 3.81 (s, 3H), 3.75-3.98 (m, 3H), 3.42-3.64 (m, 3H), 3.39 (d, J=7.8 Hz, 2H), 2.60 (d, J=9.3 Hz, 1H), 2.61-2.79 (m, 1H), 1.78-1.93 (m, 2H), 1.74-1.77 (m, 1H), 1.25 (s, H), 1.05 (d, J=6.7 Hz, 3H), 0.92 (s, 9H), 0.88 (s, 9H), 0.82-0.92 (m, 6H), 0.49-0.60 (m, 12H), 0.09 (s, 3H), 0.05 (s, 3H), 0.04 (s, 3H), 0.03 (s, 3H).

MS (ESI) m/z: 927 (M+23)$^+$.

R$_f$=0.30 (Hex:EtOAc, 4:1).

Example 38

Compound 15a

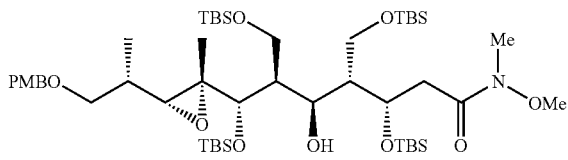

To a solution of 14a (1.09 g, 1.26 mmol) in CH$_2$Cl$_2$ (20 mL) was added 2,6-lutidine (443 μL, 3.8 mmol) and TBSOTf (437 μL, 1.9 mmol) at 0° C. The reaction mixture was stirred at 0° C. for 40 min. Then, a saturated aqueous solution of NH$_4$Cl (30 mL) was added, and the reaction was extracted with CH$_2$Cl$_2$ (2×15 mL). The combined organic layers were dried over Na$_2$SO$_4$, filtered, and concentrated under reduced pressure. The residue was purified by flash column chromatography on silica gel (Hex:EtOAc, from 20:1 to 4:1) to obtain compound 15a (1.05 g, 85%) as a pale yellow oil.

$^1$H NMR (300 MHz, CDCl$_3$) δ 7.23 (d, J=8.4 Hz, 2H), 6.87 (d, J=8.4 Hz, 2H), 4.87-4.83 (m, 1H), 4.48-4.37 (m, 2H), 4.17-4.14 (m, 2H), 3.86 (dd, J=10.2, 7.0 Hz, 1H), 3.80 (s, 3H), 3.66 (s, 3H), 3.64-3.63 (m, 1H), 3.54 (dd, J=10.2, 3.6 Hz, 1H), 3.53 (dd, J=9.0, 5.1 Hz, 1H), 3.35-3.29 (m, 2H), 3.17 (s, 3H), 3.11-3.05 (m, 1H), 2.56-2.55 (m, 1H), 2.52 (d, J=8.1 Hz, 1H), 2.31-2.28 (m, 1H), 1.84-1.82 (m, 1H), 1.81-1.78 (m, 1H), 1.29 (s, 3H), 1.09 (d, J=6.6 Hz, 3H), 0.92 (s, 9H), 0.89 (s, 9H), 0.88 (s, 9H), 0.87 (s, 9H), 0.15 (s, 6H), 0.1 (s, 3H), 0.09 (s, 3H), 0.06 (s, 3H), 0.04 (s, 6H), 0.02 (s, 3H).

$^{13}$C NMR (75 MHz, CDCl$_3$) δ 173.4, 159.4, 130.4, 129.4, 114.0, 76.0, 72.9, 72.4, 69.5, 68.8, 64.6, 64.1, 61.4, 61.0, 59.3, 55.4, 50.1, 43.6, 34.3, 29.9, 26.5, 26.2, 26.1, 26.0, 18.7, 18.3, 17.9, 15.4, 12.7, −4.4, −4.5, −4.6, −4.9, −5.0, −5.2, −5.4, −5.5.

MS (ESI) m/z: 994 (M+23)$^+$, 972 (M+1)$^+$.

[α]$^{25}_D$ −20.0 (c 0.5, CH$_2$Cl$_2$).

R$_f$=0.43 (Hex:EtOAc, 4:1)

Example 39

Compound 15b

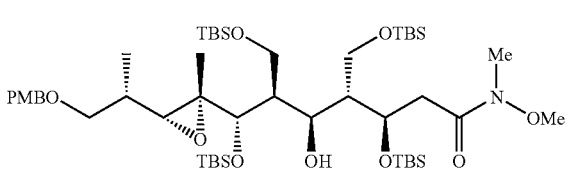

Following the procedure described in example 38, 14b (2.18 g, 2.52 mmol) was converted to 15b (2.02 g, 82%, white solid) after purification of the crude product by flash column chromatography (Hex:EtOAc 10:1).

$^1$H NMR (300 MHz, CDCl$_3$) δ 7.20 (d, J=8.7 Hz, 2H), 6.86 (d, J=8.7 Hz, 2H), 4.85-4.82 (m, 1H), 4.44-4.35 (m, 2H), 4.09 (t, J=9.0 Hz, 1H), 3.80 (s, 3H), 3.77-3.73 (m, 1H), 3.65 (s, 3H), 3.63-3.60 (m, 1H), 3.42-3.30 (m, 3H), 3.15 (s, 3H), 2.75-2.72 (m, 1H), 2.61 (d, J=9.3 Hz, 1H), 2.48 (dd, J=15.3, 2.1 Hz, 1H), 1.93-1.88 (m, 1H), 1.84-1.81 (m, 1H), 1.77-1.74 (m, 1H), 1.27 (s, 3H), 1.08 (d, J=6.6 Hz, 3H), 0.90 (s, 3H), 0.88 (s, 18H), 0.85 (s, 9H), 0.13, (s, 3H), 0.09 (s, 3H), 0.08 (s, 6H), 0.04 (s, 3H), 0.03 (s, 3H), 0.01 (s, 6H).

$^{13}$C NMR (75 MHz, CDCl$_3$) δ 173.3, 159.4, 130.4, 129.4, 114.0, 76.0, 72.9, 69.5, 68.8, 64.6, 64.1, 61.3, 61.1, 59.3, 55.4, 50.1, 43.5, 34.3, 29.9, 26.5, 26.2, 26.1, 26.0, 18.7, 18.3, 18.2, 17.9, 15.4, 12.7, −4.4, −4.5, −4.6, 4.9, −5.0.

MS (ESI) m/z: 994 (4+23)$^+$, 972 (M+1)$^+$.

[α]$^{25}_D$ +23.1 (c 0.50, CH$_2$Cl$_2$).

R$_f$=0.37 (Hex:EtOAc, 4:1).

Example 40

Compound 16a

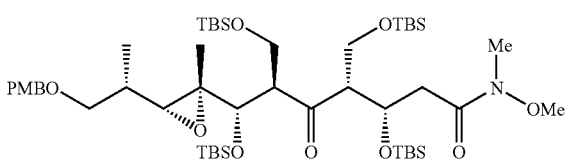

To a solution of 15a (184 mg, 0.189 mmol) in CH$_2$Cl$_2$ (5 mL) was added Dess-Martin periodinane (325 mg, 0.76 mmol) and catalytic amount of NaHCO$_3$ at 23° C. The reaction mixture was stirred at 23° C. for 3 h. Saturated aqueous solution of NaHCO$_3$ (20 mL) was added and the mixture was extracted with CH$_2$Cl$_2$ (3×30 mL). The combined organic layers were dried over Na$_2$SO$_4$, filtered, and concentrated under reduced pressure. The residue was purified by flash column chromatography on silica gel (Hex:EtOAc, 10:1) to obtain 16a (150 mg, 81%) as a colourless oil.

$^1$H NMR (300 MHz, CDCl$_3$) δ 7.23 (d, J=8.7 Hz, 2H), 6.87 (d, J=8.7 Hz, 2H), 4.72-4.67 (m, 1H), 4.43 (q, J=11.7 Hz, 2H), 3.80 (s, 3H), 3.78-3.77 (m, 2H), 3.72-3.66 (m, 3H), 3.63 (s, 3H), 3.43-3.38 (m, 1H), 3.32-3.26 (m, 3H), 3.15 (s, 3H), 2.72 (d, J=9.0 Hz, 1H), 2.65 (brd, J=8.7 Hz, 1H), 2.59-2.51 (m, 1H), 1.79-1.72 (m, 1H), 1.32 (s, 3H), 1.06 (d, J=6.6 Hz, 3H), 0.89 (s, 9H), 0.87 (s, 9H), 0.86 (s, 18H), 0.14 (s, 3H), 0.09 (s, 3H), 0.06 (s, 3H), 0.05 (s, 6H), 0.04 (s, 3H), 0.00 (s, 6H).

$^{13}$C NMR (75 MHz, CDCl$_3$) δ 210.7, 172.1, 159.1, 130.3, 129.0, 113.7, 75.9, 72.6, 72.1, 68.1, 63.7, 63.3, 61.4, 61.1, 60.1, 59.9, 57.6, 55.1, 37.2, 33.8, 29.7, 26.1, 26.0, 25.9, 25.8, 18.2, 18.1, 18.0, 15.2, 13.2, −4.3, −4.5, −4.7, −4.9, −5.2, −5.3, −5.4, −5.5.

MS (ESI) m/z: 993 (M+23)+.
$[\alpha]^{25}_D$ −20.3 (c 0.50, $CH_2Cl_2$).
$R_f$=0.40 (Hex:EtOAc, 4:1).

Example 41

Compound 16b

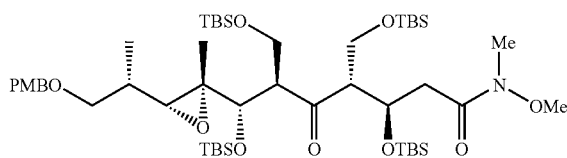

To a solution of 15b (725 mg, 0.745 mmol) in $CH_2Cl_2$ (15 mL) was added Dess-Martin periodinane (1.26 g, 2.98 mmol) and catalytic amount of $NaHCO_3$ at 23° C. The reaction mixture was stirred at 23° C. for 2 h. A saturated aqueous solution of $NaHCO_3$ (30 mL) was added and the mixture was extracted with $CH_2Cl_2$ (3×40 mL). The combined organic layers were dried over $Na_2SO_4$, filtered, and concentrated under reduced pressure. The residue (720 mg) was used in the next reaction without further purification.

$^1$H NMR (300 MHz, $CDCl_3$) δ 7.21 (d, J=8.7 Hz, 2H), 6.83 (d, J=8.7 Hz, 2H), 4.68-4.64 (m, 1H), 4.41 (q, J=11.7 Hz, 2H), 3.98-3.85 (m, 3H), 3.76 (s, 3H), 3.67 (dd, J=9.9, 3.0 Hz, 1H), 3.63 (s, 3H), 3.58 (d, J=7.8 Hz, 1H), 3.43 (dd, J=9.3, 6.9 Hz, 1H), 3.30-3.23 (m, 2H), 3.11 (s, 3H), 3.93-2.88 (m, 1H), 2.62-2.57 (m, 2H), 2.55 (d, J=9.3 Hz, 1H), 1.75-1.70 (m, 1H), 1.26 (s, 3H), 1.03 (d, J=6.6 Hz, 3H), 0.87 (s, 9H), 0.84 (s, 9H), 0.83 (s, 9H), 0.82 (s, 9H), 0.10 (s, 3H), 0.08 (s, 3H), 0.05 (s, 6H), 0.01 (s, 3H), 0.00 (s, 3H), −0.02 (s, 3H), −0.03 (s, 3H).

$^{13}$C NMR (75 MHz, $CDCl_3$) δ 208.4, 171.3, 159.4, 130.6, 129.3, 114.0, 76.0, 72.9, 66.9, 64.1, 63.0, 61.4, 60.7, 60.6, 58.7, 58.5, 55.4, 34.1, 26.4, 26.3, 26.2, 26.1, 26.0, 18.5, 18.4, 18.3, 18.2, 15.5, 14.4, 13.0, −4.3, −4.4, −4.6, −4.7, −4.9, −5.1, −5.2.

MS (ESI) m/z: 992 (M+23)+.
$[\alpha]^{25}_D$ +39.7 (c 0.5, $CH_2Cl_2$).
$R_f$=0.45 (Hex:EtOAc, 4:1).

Example 42

Compound 17a

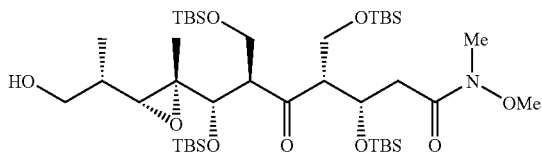

To a solution of 16a (289 mg, 0.3 mmol) in a mixture of $CH_2Cl_2$:$H_2O$ (10:0.5 mL) was added 2,3-dichloro-5,6-dicyano-1,4-benzoquinone (200 mg, 0.89 mmol) at 23° C. The reaction mixture was stirred at 23° C. for 45 min. Saturated aqueous solution of $NaHCO_3$ (30 mL) was added and the mixture was extracted with $CH_2Cl_2$ (3×40 mL). The combined organic layers were dried over $Na_2SO_4$, filtered, and concentrated under reduced pressure. The residue was solved in MeOH and $NaBH_4$ (35 mg, 0.95 mmol) was added and the reaction was stirred at 23° C. for 30 min. Then, the reaction was concentrated under reduced pressure. A saturated aqueous solution of $NaHCO_3$ (20 mL) was added and the mixture was extracted with $CH_2Cl_2$ (3×30 mL). The combined organic layers were dried over $Na_2SO_4$, filtered, and concentrated under reduced pressure. The residue was purified by flash column chromatography on silica gel (Hex:EtOAc, 6:1) to obtain 17a (153 mg, 60%) as a colourless oil.

$^1$H NMR (300 MHz, $CDCl_3$) δ 4.56-4.51 (m, 1H), 3.98-3.74 (m, 4H), 3.64 (s, 3H), 3.61 (bs, 1H), 3.53 (d, J=3.9 Hz, 1H), 3.51-3.46 (m, 1H), 3.42-3.37 (m, 1H), 3.23-3.18 (m, 1H), 3.14 (s, 3H), 2.69 (brd, J=6.3 Hz, 1H), 2.65 (brd, J=5.1 Hz, 1H), 2.58 (d, J=9.6 Hz, 1H), 1.72-1.64 (m, 1H), 1.32 (s, 3H), 0.95 (d, J=6.9 Hz, 3H), 0.90 (s, 9H), 0.88 (s, 9H), 0.87 (s, 9H), 0.85 (s, 9H), 0.13 (s, 3H), 0.09 (s, 3H), 0.05 (s, 9H), 0.04 (s, 3H), 0.03 (s, 3H), 0.00 (s, 3H).

$^{13}$C NMR (75 MHz, $CDCl_3$) δ 212.7, 171.9, 75.6, 67.6, 65.5, 64.2, 63.2, 61.4, 61.1, 60.9, 60.6, 60.4, 38.1, 35.7, 32.1, 31.9, 29.7, 26.0, 25.9, 18.4, 18.3, 18.1, 18.0, 14.2, 14.2, −4.5, −4.6, −4.7, −5.2, −5.3, −5.4, −5.5.

MS (ESI) m/z: 872 (M+23)+.
$[\alpha]^{25}_D$ −29.5 (c 0.5, $CH_2Cl_2$).
$R_f$=0.20 (Hex:EtOAc, 4:1).

Example 43

Compound 17b

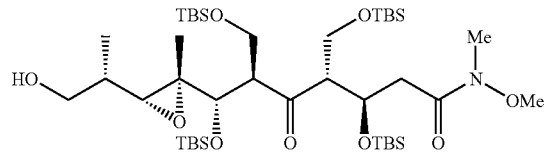

To a solution of crude 16b (0.745 mmol) in a mixture of $CH_2Cl_2$:$H_2O$ (10:0.5 mL) was added 2,3-dichloro-5,6-dicyano-1,4-benzoquinone (507 mg, 2.23 mmol) at 23° C. The reaction mixture was stirred at 23° C. for 40 min. Saturated aqueous solution of $NaHCO_3$ (30 mL) was added and the mixture was extracted with $CH_2Cl_2$ (3×40 mL). The combined organic layers were dried over $Na_2SO_4$, filtered, and concentrated under reduced pressure. The residue was solved in MeOH and $NaBH_4$ (35 mg, 0.95 mmol) was added in portions during 2 h at 23° C. Then, the reaction was concentrated under reduced pressure. Saturated aqueous solution of $NaHCO_3$ (20 mL) was added and the mixture was extracted with $CH_2Cl_2$ (3×30 mL). The combined organic layers were dried over $Na_2SO_4$, filtered, and concentrated under reduced pressure. The residue was purified by flash column chromatography on silica gel (Hex:EtOAc, 6:1) to obtain 17b (474 mg, 75% for 2 steps) as a colourless oil.

$^1$H NMR (300 MHz, $CDCl_3$) δ 4.58 (dt, J=9.9, 3.0 Hz, 1H), 4.13-3.99 (m, 3H), 3.88 (td, J=9.0, 2.4 Hz, 2H), 3.64 (s, 3H), 3.60 (dd, J=8.7, 4.0 Hz, 1H), 3.54-3.45 (m, 1H), 3.43 (d, J=3.6 Hz, 1H), 3.24 (dt, J=9.9, 3.0 Hz, 1H), 3.15-3.13 (m, 1H), 3.11 (s, 3H), 2.56-2.48 (m, 1H), 2.42 (d, J=9.6 Hz, 1H), 2.30 (dd, J=16.2, 2.4 Hz, 1H), 1.27 (s, 3H), 0.93 (s, 9H), 0.91 (m, 3H), 0.88 (s, 9H), 0.86 (s, 18H), 0.15 (s, 3H), 0.14 (s, 3H), 0.12 (s, 3H), 0.07 (s, 6H), 0.04 (s, 6H), 0.01 (s, 3H).

13C NMR (75 MHz, $CDCl_3$) δ 213.0, 171.4, 74.6, 65.7, 65.5, 64.1, 63.6, 63.5, 62.3, 61.1, 60.1, 59.1, 35.9, 34.8, 32.0, 29.6, 26.1, 26.0, 25.8, 25.7, 18.5, 18.3, 17.9, 14.2, 14.0, −4.5, −4.7, −5.0, −5.2, −5.3, −5.5, −5.6.

MS (ESI) m/z: 872 (M+23)+.
$[\alpha]^{25}_D$ −14.4 (c 0.5, $CH_2Cl_2$).
$R_f$ 0.30 (Hex:EtOAc, 4:1).

Example 44

Compound 17c

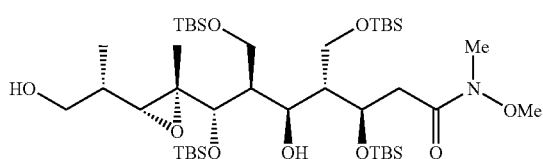

To a solution of 15b (289 mg, 0.3 mmol) in a mixture of CH$_2$Cl$_2$:H$_2$O (10:0.5 mL) was added 2,3-dichloro-5,6-dicyano-1,4-benzoquinone (200 mg, 0.89 mmol) at 23° C. The reaction mixture was stirred at 23° C. for 30 min. Saturated aqueous solution of NaHCO$_3$ (30 mL) was added and the mixture was extracted with CH$_2$Cl$_2$ (3×40 mL). The combined organic layers were dried over Na$_2$SO$_4$, filtered, and concentrated under reduced pressure. The residue was solved in MeOH and NaBH$_4$ (35 mg, 0.95 mmol) was added and the reaction was stirred at 23° C. for 30 min. Then, the reaction was concentrated under reduced pressure. A saturated aqueous solution of NaHCO$_3$ (20 mL) was added and the mixture was extracted with CH$_2$Cl$_2$ (3×30 mL). The combined organic layers were dried over Na$_2$SO$_4$, filtered, and concentrated under reduced pressure. The residue was purified by flash column chromatography on silica gel (Hex:EtOAc, 7:1) to obtain 17c (61 mg, 24%) as a white solid.

$^1$H NMR (300 MHz, CDCl$_3$) δ 4.70-4.66 (m, 1H), 4.05-4.03 (m, 2H), 3.85-3.81 (m, 3H), 3.68 (s, 3H), 3.67-3.65 (m, 1H), 3.50 (br t, J=9.3 Hz, 2H), 3.38 (d, J=7.5 Hz, 1H), 3.18 (bs, 3H), 2.64 (d, J=8.7 Hz, 1H), 2.50 (dd, J=15.0, 1.8 Hz, 1H), 2.09-2.07 (m, 1H), 2.00-1.95 (m, 1H), 1.78-1.77 (m, 1H), 1.27 (s, 3H), 1.09 (d, J=6.9 Hz, 3H), 0.91 (s, 9H), 0.88 (s, 9H), 0.87 (s, 9H), 0.85 (s, 9H), 0.84 (s, 9H), 0.14 (s, 3H), 0.08 (s, 3H), 0.07 (s, 3H), 0.06 (s, 3H), 0.05 (s, 3H), 0.04 (s, 3H), 0.03 (s, 3H), −0.02 (s, 3H).

MS (ESI) m/z: 874 (M+23)$^+$.

R$_f$=0.26 (Hex:EtOAc, 4:1).

Example 45

Compound 18a

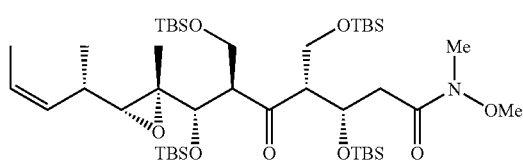

To a solution of 17a (113 mg, 0.13 mmol) in CH$_2$Cl$_2$ (2 mL) was added Dess-Martin periodinane (141 mg, 1.33 mmol) and catalytic amount of NaHCO$_3$ at 23° C. The reaction mixture was stirred at 23° C. for 40 min. A saturated aqueous solution of NaHCO$_3$ (10 mL) was added and the mixture was extracted with CH$_2$Cl$_2$ (3×10 mL). The combined organic layers were dried over Na$_2$SO$_4$, filtered, and concentrated under reduced pressure to give the corresponding aldehyde (Rf=0.33 Hex:EtOAc 4:1). Meanwhile, to a suspension of ethyl triphenylphosphonium bromide (395 mg) in toluene (7 mL) was added 1M/THF potassium t-butoxide (0.85 mL) at 0° C. The resulting orange solution was stirred at 0° C. for 25 min and then cooled to −78° C. Then, a solution of the fresh crude aldehyde in toluene (5 mL) was added dropwise to the previous suspension at −78° C. and the mixture was allowed to reach 23° C. during 14 h. The reaction mixture was diluted with CH$_2$Cl$_2$ (10 mL) and washed with a saturated NaHCO$_3$ solution (15 mL). The organic phase was dried over MgSO4, filtered, and concentrated in vacuo. The residue was purified by flash column chromatography on silica gel (Hex:EtOAc, 15:1) to obtain 18a (80 mg, 70% for 2 steps) as a colourless oil.

$^1$H NMR (300 MHz, CDCl$_3$) δ 5.52-5.41 (m, 1H), 5.26 (td, J=10.2, 1.5 Hz, 1H), 4.73-4.68 (m, 1H), 3.81 (dd, J=10.5, 4.5 Hz, 1H), 3.75-3.69 (m, 2H), 3.63 (s, 3H), 3.60 (s, 2H), 3.29-3.24 (m, 1H), 3.22-3.16 (m, 1H), 3.14 (s, 3H), 2.71 (d, J=9.3 Hz, 1H), 2.65 (brd, J=7.2 Hz, 1H), 2.52 (dd, J=15.9, 3.3 Hz, 1H), 2.44-2.35 (m, 1H), 1.61 (dd, J=6.9, 1.5 Hz, 3H), 1.29 (s, 3H), 1.10 (d, J=6.3 Hz, 3H), 0.89 (s, 9H), 0.88 (s, 9H), 0.87 (s, 9H), 0.86 (s, 9H), 0.14 (s, 3H), 0.10 (s, 3H), 0.06 (s, 3H), 0.05 (s, 6H), 0.04 (s, 3H), 0.01 (s, 3H), 0.00 (s, 3H).

$^{13}$C NMR (75 MHz, CDCl$_3$) δ 211.2, 172.2, 130.9, 124.2, 76.7, 67.7, 64.9, 62.8, 62.2, 61.1, 60.7, 59.5, 57.3, 37.7, 31.8, 29.7, 26.2, 26.0, 25.9, 25.8, 18.9, 18.3, 18.2, 18.1, 18.1, 13.1, 12.3, −4.3, −4.4, −4.7, −4.9, −5.3, −5.4, −5.5.

MS (ESI) m/z: 882 (M+23)$^+$.

R$_f$=0.52 (Hex:EtOAc, 4:1).

Example 46

Compound 18b

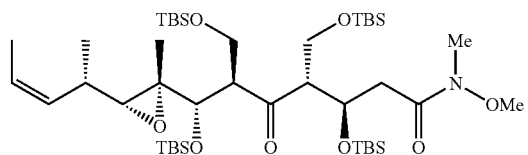

To a solution of 17b (474 mg, 0.557 mmol) in CH$_2$Cl$_2$ (10 mL) was added Dess-Martin periodinane (590 mg, 1.39 mmol) and catalytic amount of NaHCO$_3$ at 23° C. The reaction mixture was stirred at 23° C. for 40 min. A saturated aqueous solution of NaHCO$_3$ (30 mL) was added and the mixture was extracted with CH$_2$Cl$_2$ (3×40 mL). The combined organic layers were dried over Na$_2$SO$_4$, filtered, and concentrated under reduced pressure to give the corresponding aldehyde (R$_f$=0.38 Hex:EtOAc 4:1). Meanwhile, to a suspension of ethyl triphenylphosphonium bromide (1.64 g) in toluene (15 mL) was added 1M/THF potassium t-butoxide (3.56 mL) at 0° C. The resulting orange solution was stirred at 0° C. for 25 min and then cooled to −78° C. Then, a solution of the fresh crude aldehyde in toluene (10 mL) was added dropwise to the previous suspension at −78° C. and the mixture was allowed to reach 23° C. during 14 h. The reaction mixture was diluted with CH$_2$Cl$_2$ (20 mL) and washed with a saturated NaHCO$_3$ solution (30 mL). The organic phase was dried over MgSO$_4$, filtered, and concentrated in vacuo. The residue was purified by flash column chromatography on silica gel (Hex:EtOAc, from 15:1 to 10:1) to obtain 18b (347 mg, 72% for 2 steps) as a colourless oil.

$^1$H NMR (300 MHz, CDCl$_3$) δ 5.51-5.45 (m, 1H), 5.29 (td, J=11.1, 1.5 Hz, 1H), 4.76-4.71 (m, 1H), 3.98 (dd, J=9.6, 3.3 Hz, 1H), 3.90 (dd, J=9.6, 7.2 Hz, 1H), 3.69-3.68 (m, 2H), 3.65 (s, 3H), 3.59 (d, J=8.7 Hz, 1H), 3.36-3.30 (m, 1H), 3.15 (s, 3H), 2.92-2.88 (m, 1H), 2.62 (d, J=9.3 Hz, 1H), 2.58 (d, J=2.1 Hz, 1H), 2.55-2.52 (m, 1H), 2.43-2.35 (m, 1H), 1.61 (dd, J=6.6, 1.5 Hz, 3H), 1.26 (s, 3H), 1.10 (d, J=6.6 Hz, 3H), 0.92 (s, 9H), 0.86 (s, 9H), 0.85 (s, 9H), 0.84 (s, 9H), 0.12 (s, 3H), 0.09 (s, 9H), 0.03 (s 3H), 0.00 (s, 9H).

¹³C NMR (75 MHz, CDCl₃) δ 208.63, 172.3, 130.9, 124.2, 76.2, 66.7, 65.0, 62.5, 61.3, 61.1, 60.0, 56.8, 36.7, 31.8, 29.7, 26.2, 25.9, 25.9, 18.9, 18.3, 18.2, 18.1, 18.0, 13.1, 12.0, −4.5, −4.7, −4.8, −4.9, −5.2, −5.3, −5.5.
MS (ESI) m/z: 882 (M+23)⁺.
[α]²⁵_D +73.9 (c 0.5, CH₂Cl₂).
R_f=0.50 (Hex:EtOAc, 4:1).

Example 47

Compound 18c

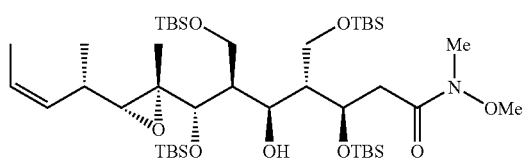

Following the procedure described in example 45, 17c (60 mg, 0.07 mmol) was converted to 18c (30 mg, 50%, pale yellow oil) after purification of the crude product by flash column chromatography (Hex:EtOAc 10:1).
¹H NMR (300 MHz, CDCl₃) δ 5.48-5.40 (m, 1H), 5.32-5.25 (m, 1H), 4.85-4.80 (m, 1H), 4.10 (dd, J=11.1, 2.4 Hz, 1H), 4.01 (brt, J=9.0 Hz, 1H), 3.83 (dd, J=10.2,−5.4 Hz, 1H), 3.76 (br d, J=10.8 Hz, 1H), 3.66 (s, 3H), 3.62 (d, J=10.2 Hz, 1H), 3.52 (dd, J=10.2. 6.0 Hz, 1H), 3.37 (d, J=8.4 Hz, 1H), 3.16 (s, 3H), 2.71 (d, J=9.3 Hz, 1H), 2.61-2.58 (m, 1H), 2.50-2.39 (m, 2H), 2.03-2.00 (m, 1H), 1.77 (br d, J=8.4 Hz, 1H), 1.59 (dd, J=6.6, 1.5 Hz, 3H), 1.24 (s, 3H), 1.13 (d, J=6.9 Hz, 3H), 0.91 (s, 9H), 0.90 (s, 9H), 0.86 (s, 9H), 0.85 (s, 9H), 0.15 (s, 3H), 0.13 (s, 3H), 0.10 (s, 6H), 0.08 (s, 3H), 0.03 (s, 3H), 0.01 (s, 3H).
MS (ESI) m/z: 862 (M+1)⁺.
R_f=0.48 (Hex:EtOAc, 4:1).

Example 48

Compound 19a

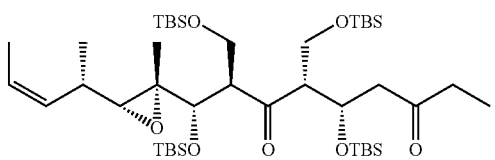

To a solution of 18a (80 mg, 0.093 mmol) in THF (1.5 mL) was added BrMgEt (0.28 mL, 1.0 M in THF, 0.28 mmol) at 23° C. The reaction mixture was stirred at 23° C. for 3 h. Saturated aqueous solution of NaHCO₃ (10 mL) was added and the mixture was extracted with CH₂Cl₂ (3×15 mL). The combined organic layers were dried over Na₂SO₄, filtered, and concentrated under reduced pressure. The residue was purified by flash column chromatography on silica gel (Hex:EtOAc, 30:1) to obtain 19a (57 mg, 75%) as a white solid.

¹H NMR (300 MHz, CDCl₃) δ 5.53-5.43 (m, 1H), 5.26 (td, J=10.2, 1.5 Hz, 1H), 4.71-4.66 (m, 1H), 3.77 (dd, J=10.8, 4.5 Hz, 1H), 3.67 (d, J=5.7 Hz, 2H), 3.60 (t, J=9.3 Hz, 1H), 3.50 (d, J=8.7 Hz, 1H), 3.34-3.27 (m, 1H), 3.20-3.14 (m, 1H), 2.64 (d, J=9 Hz, 1H), 2.58-2.56 (m, 2H), 2.41-2.34 (m, 3H), 1.61 (dd, J=6.6, 1.8 Hz, 3H), 1.29 (s, 3H), 1.10 (d, J=6.3 Hz, 3H), 1.00 (t, J=7.5 Hz, 3H), 0.89 (s, 18H), 0.87 (s, 9H), 0.86 (s, 9H), 0.15 (s, 3H), 0.10 (s, 3H), 0.05 (s, 3H), 0.04 (s, 6H), 0.03 (s, 6H), 0.00 (s, 3H).
¹³C NMR (75 MHz, CDCl₃) δ 211.9, 209.2, 130.9, 124.4, 77.3, 67.4, 65.0, 62.7, 62.1, 60.8, 59.8, 57.6, 47.2, 37.1, 31.7, 29.7, 26.3, 26.0, 25.9, 25.8, 18.9, 18.4, 18.3, 18.1, 18.0, 13.1, 12.2, 7.5, −4.2, −4.3, 4.7, −5.0, −5.3, −5.5, −5.6.
MS (ESI) m/z: 851 (M+23)⁺.
[α]²⁵_D −11.3 (c 0.5, CH₂Cl₂).
R_f=0.74 (Hex:EtOAc, 4:1).

Example 49

Compound 19b

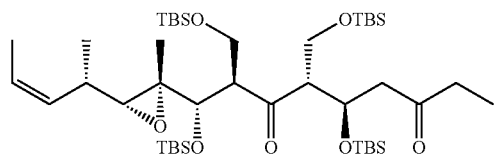

To a solution of 18b (347 mg, 0.4 mmol) in THF (4 mL) was added 1M/THF BrMgEt (1.5 mL, 1.5 mmol) at 23° C. The reaction mixture was stirred at 23° C. for 3 h. Saturated aqueous solution of NaHCO₃ (30 mL) was added and the mixture was extracted with CH₂Cl₂ (3×30 mL). The combined organic layers were dried over Na₂SO₄, filtered, and concentrated under reduced pressure. The residue was purified by flash column chromatography on silica gel (Hex:EtOAc, 40:1) to obtain 19b (280 mg, 84%) as a colourless oil.
¹H NMR (300 MHz, CDCl₃) δ 5.54-5.44 (m, 1H), 5.30 (td, J=10.2, 1.5 Hz, 1H), 4.71-4.67 (m, 1H), 3.95 (dd, J=9.6, 3.3 Hz, 1H), 3.91-3.85 (m, 1H), 3.69 (d, J=1.5 Hz, 1H), 3.67 (s, 3H), 3.57 (d, J=9.0 Hz, 1H), 3.34-3.27 (m, 1H), 2.89-2.84 (m, 1H), 2.62-2.58 (m, 1H), 2.60 (d, J=9.3 Hz, 1H), 2.44-2.30 (m, 4H), 1.61 (dd, J=6.9, 1.5 Hz, 3H), 1.25 (s, 3H), 1.11 (d, J=6.6 Hz, 3H), 1.02 (t, J=7.5 Hz, 3H), 0.90 (s, 9H), 0.86 (s, 9H), 0.85 (s, 9H), 0.82 (s, 9H), 0.13 (s, 3H), 0.10 (s, 3H), 0.09 (s, 6H), 0.01 (s, 3H), 0.00 (s, 9H).
¹³C NMR (75 MHz, CDCl₃) δ 209.0, 208.7, 130.9, 124.1, 76.0, 65.8, 64.9, 62.3, 61.3, 58.0, 57.2, 46.7, 36.7, 31.8, 26.2, 25.9, 25.8, 18.8, 18.3, 18.2, 18.1, 18.0, 13.1, 12.1, 7.5, −4.5, −4.6, −4.8, −4.9, −5.3, −5.4, −5.5.
MS (ESI) m/z: 851 (M+23)⁺.
[α]²⁵_D +69.5 (c 0.5, CH₂Cl₂).
R_f=0.76 (Hex:EtOAc, 4:1).

Example 50

Compounds 20a and 20c

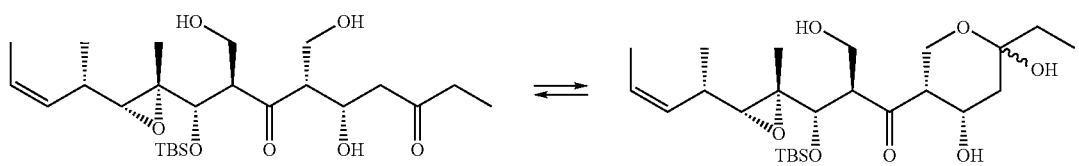

To a solution of 19a (160 mg, 0.19 mmol) in THF (6 mL) was added simultaneously TBAF (1.52 mL, 1.0 M in THF, 1.52 mmol) and AcOH (77 µL, 1.35 mmol) at 23° C. The reaction mixture was stirred at 23° C. for 16 h. H$_2$O (10 mL) was added and the mixture was extracted with EtOAc (3×10 mL). The combined organic layers were dried over Na$_2$SO$_4$, filtered, and concentrated under reduced pressure. The residue was purified by flash column chromatography on silica gel (Hex:EtOAc from 4:1 to 1:1) to obtain a tautomer equilibrium of 20a and 20c (77 mg, 82%) as a white solid.

$^1$H NMR (500 MHz, CDCl$_3$) (data of the major product) δ 5.54-5.49 (m, 1H), 5.24 (m, 1H), 4.79 (d, J=2.5 Hz, 1H), 4.30 (dd, J=12.0 Hz, 1H), 3.84 (dd, J=12.5, 4.0 Hz, 1H), 3.67-3.66 (m, 2H), 3.33 (d, J=10.0 Hz, 1H), 3.30-3.26 (m, 1H), 2.77 (ddd, J=11.5, 5.0, 2.5 Hz, 1H), 2.51 (d, J=8.5 Hz, 1H), 2.45-2.39 (m, 1H), 2.02 (dd, J=14.0, 3.5 Hz, 1H), 1.73 (dd, J=14.0, 3.0 Hz, 1H), 1.63 (dd, J=7.0, 1.5 Hz, 3H), 1.61-1.58 (m, 2H), 1.31 (s, 3H), 1.12 (d, J=6.5 Hz, 3H), 0.93 (t, J=7.5 Hz, 3H), 0.86 (s, 9H), 0.11 (s, 3H), −0.04 (s, 3H).

$^{13}$C NMR (125 MHz, CDCl$_3$) (data of the major product) δ 213.1, 130.5, 124.8, 97.3, 78.6, 65.3, 65.2, 62.2, 61.3, 55.5, 55.2, 54.7, 37.3, 34.5, 31.6, 29.7, 26.0, 18.7, 13.3, 11.4, 7.4, −4.4, −5.2.

MS (ESI) m/z: 509 (M+23)$^+$, 451 (M+H−2×H$_2$O)$^+$.
R$_f$=0.56 (Hex:EtOAc, 1:2).

Example 51

Compounds 20b and 20d

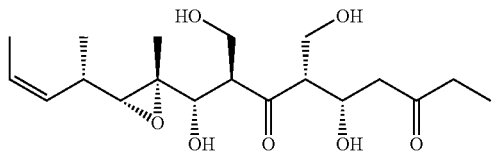

Following the procedure described in example 50, 19b (35 mg, 0.04 mmol) was converted to a tautomer equilibrium of 20b and 20d (12 mg, 60%, pale yellow oil) after purification of the crude product by flash column chromatography (Hex:EtOAc from 4:1 to 1:1).

$^1$H NMR (500 MHz, CDCl$_3$) (data of the major product) δ 5.56-5.50 (m, 1H), 5.32-5.26 (m, 1H), 4.38 (ddd, J=15.5, 11.5, 5.0 Hz, 1H), 3.86-3.76 (m, 4H), 3.53 (d, J=9.5 Hz, 1H), 3.24-3.20 (m, 1H), 2.89 (ddd, J=14.5, 11.0, 4.5 Hz, 1H), 2.59 (d, J=9.5 Hz, 1H), 2.46-2.41 (m, 1H), 2.08 (dd, J=12.5, 5.0 Hz, 1H), 1.69-1.66 (m, 2H), 1.64 (dd, J=7.0, 2.0 Hz, 3H), 1.46 (dd, J=13.0, 12.0 Hz, 1H), 1.30 (s, 3H), 1.13 (d, J=7.0 Hz, 3H), 0.97 (t, J=7.5 Hz, 3H), 0.86 (s, 3H), 0.14 (s, 3H), 0.00 (s, 3H).

$^{13}$C NMR (125 MHz, CDCl$_3$) (data of the major product) δ 213.1, 130.6, 124.7, 98.8, 77.0, 66.8, 65.1, 62.2, 60.8, 60.0, 59.0, 40.1, 35.5, 31.5, 29.7, 26.1, 18.8, 18.2, 13.3, 11.5, 7.4, −4.3, −5.0.

MS (ESI) m/z: 509 (M+23)$^+$, 451 (M+H−2×H$_2$O)$^+$.
[α]$^{25}_D$+55.0 (c 0.5, CH$_2$Cl$_2$).
R$_f$=0.51 (Hex:EtOAc, 1:2).

Example 52

Compounds 3a and 4a

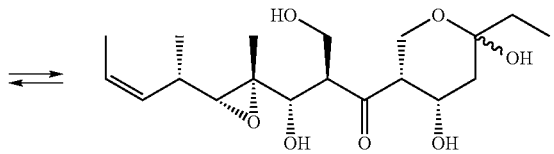

To a solution of 19a (238 mg, 0.29 mmol) in DMF (5 mL) was added simultaneously TBAF (2.9 mL, 1.0 M in THF, 2.9 mmol) and AcOH (116 µL, 2 mmol) at 23° C. The reaction mixture was stirred at 23° C. for 7 h. Saturated aqueous solution of NaHCO$_3$ (10 mL) was added and the mixture was extracted with EtOAc (3×10 mL). The combined organic layers were dried over Na$_2$SO$_4$, filtered, and concentrated under reduced pressure. The residue was purified by flash column chromatography on silica gel (Hex:EtOAc from 4:1 to 0:1) to obtain a tautomer equilibrium of 3a and 4a (25 mg, 23%) as a colourless oil.

$^1$H NMR (500 MHz, CD$_3$OD) (data of the major product) δ 5.56-5.51 (m, 1H), 5.31-5.26 (m, 1H), 4.75 (m, 1H), 4.29 (dd, J=11.5, 11.5 Hz, 1H), 3.72 (dd, J=12.5, 4.0 Hz, 1H), 3.67-3.62 (m, 2H), 3.29-3.27 (m, 1H), 3.16 (d, J=10.0 Hz, 1H), 2.89 (ddd, J=11.5, 4.5, 2.0 Hz, 1H), 2.59 (d, J=9.5 Hz, 1H), 1.93 (dd, J=14.0, 3.0 Hz, 1H), 1.75 (dd, J=14.5, 3.0 Hz, 1H), 1.65 (dd, J=6.5, 2.0 Hz, 3H), 1.56 (q, J=7.5 Hz, 2H), 1.34 (s, 3H), 1.09 (d, J=7.0 Hz, 3H), 0.92 (t, J=7.5 Hz, 3H).

$^1$H NMR (500 MHz, CDCl$_3$) (data of the major product) δ 5.55-5.48 (m, 1H), 5.27-5.20 (m, 1H), 4.74 (brd, J=2.0 Hz, 1H), 4.32 (dd, J=13.0, 13.0 Hz, 1H), 3.89 (dd, J=12.5, 4.0 Hz, 1H), 3.76 (dd, J=10.0, 9.0 Hz, 1H), 3.63 (dd, J=10.5, 3.5 Hz, 1H), 3.33 (d, J=9.5 Hz, 1H), 3.29 (dd, J=9.5, 4.0 Hz, 1H), 2.94 (ddd, J=11.5, 5.0, 2.5 Hz, 1H), 2.68 (d, J=9.0 Hz, 1H), 2.44-2.39 (m, 1H), 2.02 (dd, J=14.0, 3.0 Hz, 1H), 1.73 (dd, J=14.0, 3.0 Hz, 1H), 1.62 (dd, J=7.0, 1.5 Hz, 3H), 1.59-1.56 (m, 2H), 1.33 (s, 3H), 1.11 (d, J=6.0 Hz, 3H), 0.94 (t, J=7.5 Hz, 3H)

$^{13}$C NMR (125 MHz, CDCl$_3$) (data of the major product) δ 214.2, 130.0, 125.0, 97.3, 77.2, 66.8, 66.7, 65.2, 63.0, 55.6, 54.6, 52.9, 37.1, 34.5, 31.3, 18.6, 13.3, 11.6, 7.4. .

MS (ESI) m/z: 767 (2×M+23)⁺, 395 (M+23)⁺, 377 (M+23-H₂O)⁺.

R_f=0.24 (Hex:EtOAc, 1:2).

Example 53

Compounds 3b and 4b

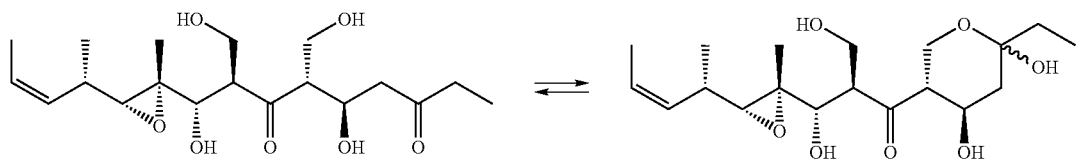

Following the procedure described in example 52, 19b (200 mg, 0.24 mmol) was converted to a tautomer equilibrium of 3b and 4b (20 mg, 21%) after purification of the crude product by flash column chromatography (Hex:EtOAc from 4:1 to 0:1).

¹H NMR (500 MHz, CDCl₃) (data of the major product) d 5.56-5.48 (m, 1H), 5.28-5.22 (m, 1H), 4.41-4.37 (m, 1H), 3.97-3.73 (m, 5H), 3.34-3.22 (m, 1H), 2.98 (ddd, J=4.5 Hz, 11.5 Hz, 14.5 Hz, 1H), 2.73 (d, J=9 Hz, 1H), 2.46-2.42 (m, 1H), 2.09 (dd, J=5 Hz, 13 Hz, 1H), 1.67 (q, J=7 Hz, 2H), 1.63 (dd, J=1.5 Hz, 7 Hz, 3H), 1.48-1.42 (m, 1H), 1.35 (s, 3H), 1.11 (d J=7 Hz, 3H), 0.96 (t, J=7 Hz, 3H).

MS (ESI) m/z: 395 (M+23)⁺, 767 (2M+23)⁺, 377 (M+23-H₂O)⁺, 337 (M+1-2H₂O)⁺, 319 (M+1-3H₂O)⁺. HRMS (TOF) Calcd for C₁₉H₃₂O₇Na: 395.2046. Found 395.2019.

R_f=0.15 (Hex:EtOAc, 1:2).

Example 54

Compound 21

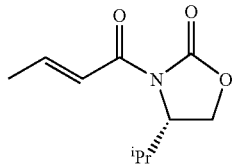

Compound 21 was prepared following the procedure described by D. A. Evans et al., *J. Am. Chem. Soc.* 1984, 106, 4261-4263.

¹H NMR (300 MHz, CDCl₃) δ 7.21 (m, 1H), 7.12 (m, 1H), 4.44 (m, 1H), 4.20 (m, 2H), 2.36 (m, 1H), 1.91 (dd, J=6.6, 1.2 Hz, 3H), 0.88 (d, J=6.9 Hz, 3H), 0.83 (d, J=6.9 Hz, 3H).

Example 55

Compound 22

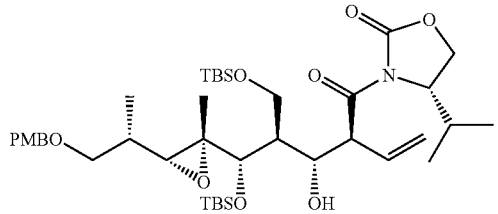

To a solution of 21 (9.39 g, 0.047 mol) in CH₂Cl₂ (75 mL) was added Bu₂BOTf (52.4 mL, 1.0 M in CH₂Cl₂, 52.4 mmol) and Et₃N (9.3 mL, 0.067 mol) at −78° C. The reaction mixture was stirred 1 h at −78° C., 15 min at 0° C. and recooled at −78° C. This solution was added over a solution of 8a (9 g, 0.016 mol) in CH₂Cl₂ (25 mL) at −50° C. and the mixture was stirred at −50° C. for an additional 10 days. Then, saturated aqueous solution of NH₄Cl (150 mL) was added and the reaction was extracted with CH₂Cl₂ (2×100 mL). The combined organic layers were dried over Na₂SO₄, filtered, and concentrated under reduced pressure. The residue was purified by flash column chromatography on silica gel (Hex:EtOAc, from 15:1 to 2:1) to afford compound 22 alone with ca. 15% of another diastereoisomer (12 g, 80%) as a colourless oil.

¹H NMR (300 MHz, CDCl₃) δ 7.20 (d, J=8.7 Hz, 2H), 6.86 (d, J=8.7 Hz, 2H), 6.20 (dt, J=17.4, 10.2 Hz, 1H), 5.25 (dd, J=11.1, 0.6 Hz, 1H), 5.20 (dd, J=19.2, 0.6 Hz, 1H), 4.47-4.33 (m, 3H), 4.28-4.09 (m, 3H), 3.95 (br d, J=3.6 Hz, 1H), 3.80 (s, 3H), 3.65-3.56 (m, 2H), 3.33 (br d, J=7.2 Hz, 2H), 2.90 (d, J=9.3 Hz, 1H), 2.45-2.35 (m, 1H), 2.33-2.23 (q, J=6.9 Hz, 1H), 1.83-1.73 (m, 1H), 1.56-1.46 (m, 1H), 1.28 (s, 3H), 1.03 (d, J=6.9 Hz, 3H), 0.90 (s, 9H), 0.87 (s, J=6.9 Hz, 3H), 0.83 (s, J=6.9 Hz, 3H), 0.82 (s, 9H), 0.09 (s, 3H), 0.08 (s, 3H), 0.06 (s, 3H), 0.05 (s, 3H).

¹³C NMR (75 MHz, CDCl₃) δ 172.9, 158.7, 153.0, 132.1, 128.7, 128.3, 118.8, 113.3, 77.0, 74.6, 72.3, 69.0, 64.7, 64.5, 63.0, 62.9, 62.7, 60.0, 58.5, 58.1, 58.0, 54.7, 50.4, 47.1, 32.9, 32.2, 30.9, 28.1, 27.9, 27.3, 25.6, 25.5, 17.8, 17.6, 14.3, 14.3, 14.2, 14.1, −5.1, −5.3, −5.8, −5.9.

MS (ESI) m/z: 786 (M+23)⁺, 764 (M+H)⁺.

R_f=0.32 (Hex:EtOAc, 4:1).

Example 56

Compound 23

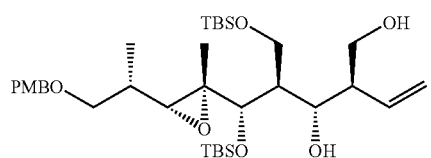

To a solution of the mixture of diastereoisomers (5:1) of 22 (3.9 g, 5.1 mmol) in THF:H₂O (5:1, 75 mL), LiBH₄ (13 mL, 2.0 M in THF, 26 mmol) was added at 0° C. The reaction mixture was stirred 30 min at 0° C. and 2.5 h at 23° C. Saturated aqueous solution of NH₄Cl (100 mL) was added and the mixture was extracted with EtOAc (3×150 mL). The combined organic layers were dried over Na₂SO₄, filtered, and concentrated under reduced pressure. The residue 23 (3.4 g) was used in the next step with no further purification.

¹H NMR (300 MHz, CDCl₃) δ 7.17 (d, J=8.4 Hz, 2H), 6.85 (d, J=9.0 Hz, 2H), 6.17-6.05 (m, 1H), 5.20 (dd, J=10.5, 1.8 Hz, 1H), 5.13 (dd, J=17.7, 1.8 Hz, 1H), 4.40-4.35 (m, 2H), 4.02 (d, J=9.6 Hz, 1H), 3.85-3.73 (m, 2H), 3.80 (s, 3H), 3.48-3.47 (m, 2H), 3.39-3.34 (m, 1H), 3.30-3.24 (m, 1H), 2.66 (d, J=9.3 Hz, 1H), 2.31-2.28 (m, 1H), 1.81-1.74 (m, 2H), 1.28 (s, 3H), 1.05 (d, J=6.6 Hz, 3H), 0.92 (s, 9H), 0.86 (s, 9H), 0.17 (s, 3H), 0.12 (s, 3H), 0.00 (s, 3H), −0.01 (s, 3H).

$^{13}$C NMR (75 MHz, CDCl$_3$) δ 159.4, 135.8, 130.3, 129.2, 118.3, 114.0, 79.1, 73.2, 73.0, 72.3, 67.2, 65.6, 64.4, 60.4, 55.4, 47.7, 46.7, 33.6, 26.2, 18.5, 18.2, 15.0, 12.9, −4.1, −5.0, −5.1, −5.4.

MS (ESI) m/z: 661 (M+23)$^+$, 639 (14+H)$^+$.

R$_f$=0.18 (Hex:EtOAc, 4:1).

Example 57

Compound 24

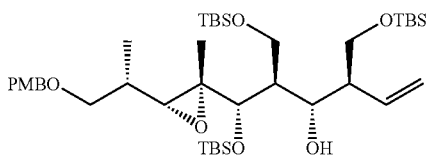

To a solution of crude 23 (5 mmol) in CH$_2$Cl$_2$ (60 mL) was added imidazole (1.02 g, 15 mmol) and TBSCl (1.13 g, 7.5 mmol) at 23° C. The reaction mixture was stirred at 23° C. for 15 min. A saturated aqueous solution of NH$_4$Cl (70 mL) was added and the reaction was extracted with CH$_2$Cl$_2$ (2×100 mL). The combined organic layers were dried over Na$_2$SO$_4$, filtered, and concentrated under reduced pressure. The residue was purified by flash column chromatography on silica gel (Hex:EtOAc, 20:1) to obtain pure compound 24 (1.7 g, 43% for two steps) as a colourless oil.

$^1$H NMR (300 MHz, CDCl$_3$) δ 7.19 (d, J=8.7 Hz, 2H), 6.86 (d, J=8.7 Hz, 2H), 5.96-5.84 (m, 1H), 5.12-5.05 (m, 2H), 4.37 (q, J=11.4 Hz, 2H), 4.0 (d, J=9.3 Hz, 1H), 3.92 (s, 1H), 3.86-3.77 (m, 2H), 3.80 (s, 3H), 3.57-3.46 (m, 3H), 3.37-3.29 (m, 2H), 2.67 (d, J=9.3 Hz, 1H), 2.42-2.36 (m, 1H), 1.83-1.76 (m, 2H), 1.30 (s, 3H), 1.06 (d, J=6.9 Hz, 3H), 0.93 (s, 9H), 0.88 (s, 9H), 0.87 (s, 9H), 0.17 (s, 3H), 0.12 (s, 3H), 0.03 (s, 9H), 0.00 (s, 3H).

$^{13}$C NMR (75 MHz, CDCl$_3$) δ 159.4, 136.0, 130.4, 129.2, 118.0, 114.0, 79.2, 73.1, 72.9, 68.2, 65.3, 64.7, 64.6, 60.7, 55.4, 49.1, 47.1, 33.6, 26.3, 26.2, 26.1, 18.5, 15.1, 12.9, −4.1, −4.9, −5.1, −5.2, −5.3.

MS (ESI) m/z: 775 (M+23)$^+$, 753 (M+H)$^+$.

[α]$^{25}_D$ −8.0 (c 0.50, CH$_2$Cl$_2$).

R$_f$=0.65 (Hex:EtOAc, 4:1).

Example 58

Compound 25a

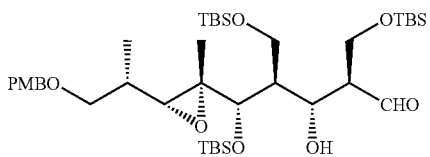

Over a solution of 24 (1.58 g, 2.09 mmol) in CH$_2$Cl$_2$ (40 mL) was bubbled a current of O$_3$ during 2 min at −78° C. Then, Ph$_3$P (1.65 g, 6.27 mmol) was added and the mixture was allowed to warm to room temperature, and the stirring was continued for 1.5 h. The mixture was concentrated under reduced pressure and the residue was purified by flash column chromatography on silica gel (Hex:EtOAc, 20:1) to afford compound 25a (1.34 g, 85%) as a colourless oil.

$^1$H NMR (300 MHz, CDCl$_3$) δ 9.77 (d, J=3.0 Hz, 1H), 7.21 (d, J=8.7 Hz, 2H), 6.89 (d, J=8.7 Hz, 2H), 4.39 (s, 2H), 4.18 (dd, J=9.9, 7.8 Hz, 1H), 4.08 (m, 1H), 4.04-4.03 (m, 1H), 3.90 (dd, J=9.9, 6.0 Hz, 1H), 3.81 (s, 3H), 3.73-3.68 (m, 2H), 3.55-3.50 (dd, J=10.5, 3.3 Hz, 1H), 3.40-3.27 (m, 2H), 2.67 (d, J=9.3 Hz, 1H), 2.62 (m, 1H), 1.98-1.92 (m, 1H), 1.83-1.74 (m, 1H), 1.27 (s, 3H), 1.05 (d, J=6.9 Hz, 3H), 0.92 (s, 9H), 0.86 (s, 9H), 0.85 (s, 9H), 0.17 (s, 3H), 0.11 (s, 3H), 0.05 (s, 6H), 0.02 (s, 3H), 0.00 (s, 3H).

$^{13}$C NMR (75 MHz, CDCl$_3$) δ 205.6, 159.4, 130.3, 129.4 114.1, 79.2, 73.2, 72.9, 70.4, 65.5, 64.0, 61.7, 60.9, 55.8, 55.4, 47.4, 33.6, 26.2, 26.0, 18.4, 18.2, 15.0, 12.9, −4.1, −5.0, −5.2, −5.3, −5.3, −5.4.

MS (ESI) m/z: 777 (M+23)$^+$.

[α]$^{25}_D$ −7.9 (c 0.52, CH$_2$Cl$_2$).

R$_f$ 0.67 (Hex:EtOAc, 4:1).

Example 59

Compound 25b

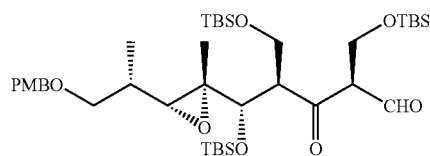

To a solution of 25a (1.34 mg, 1.78 mmol) in CH$_2$Cl$_2$ (50 mL) was added Dess-Martin periodinane (1.5 mg, 3.56 mmol) and catalytic amount of NaHCO$_3$ at 23° C. The reaction mixture was stirred at 23° C. for 50 min. A saturated aqueous solution of NaHCO$_3$ (60 mL) was added and the mixture was extracted with CH$_2$Cl$_2$ (3×70 mL). The combined organic layers were dried over Na$_2$SO$_4$, filtered, and concentrated under reduced pressure to give aldehyde 25b which was used in the next step with no further purification.

$^1$H-NMR (300 MHz, CDCl$_3$): δ 9.59 (d, J=2.7 Hz, 1H), 7.23 (d, J=8.6 Hz, 2H), 6.88 (d, J=8.6 Hz, 2H), 4.36-4.48 (m, 2H), 4.22-4.29 (m, 1H), 3.98-4.07 (m, 1H), 3.81-3.88 (m, 1H), 3.80 (s, 3H), 3.64-3.78 (m, 2H), 3.32-3.45 (m, 4H), 2.47 (d, J=9.3 Hz, 1H), 1.68-1.81 (m, 1H), 1.24 (s, 3H), 1.03 (d, J=6.7 Hz, 3H), 0.92 (s, 9H), 0.91 (s, 9H), 0.90 (s, 9H), 0.06 (s, 3H), 0.05 (s, 3H), 0.03 (s, 3H), 0.02 (s, 3H), −0.01 (s, 3H), −0.02 (s, 3H).

R$_f$=0.69 (Hex:EtOAc, 4:1).

Example 60

Compounds 26a and 26b

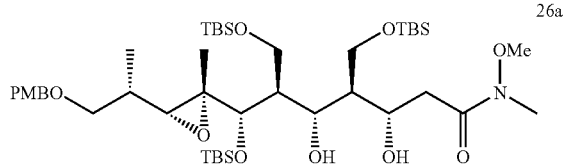

-continued

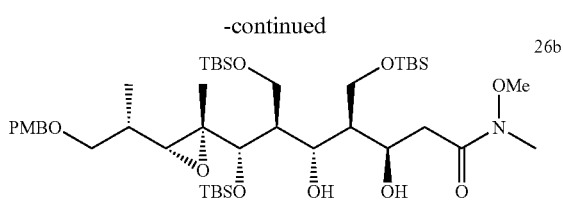

To a solution of N-methoxy-N-methylacetamide (70 µL g, 0.65 mmol) in THF (2 mL) at −78° C. was added bis-(trimethylsilyl)-lithiumamid (0.65 mL, 1.0 M in THF, 0.65 mmol) and the reaction mixture was stirred for 1 h at that temperature. Then, a solution of 25a (165 mg, 0.22 mmol) in THF (4 mL) was added over the previous solution and the reaction mixture was stirred for an additional 1 h at −78° C. Then, a saturated aqueous solution of NH$_4$Cl (30 mL) was added and the reaction was extracted with EtOAc (3×50 mL). The combined organic layers were dried over Na$_2$SO$_4$, filtered, and concentrated under reduced pressure. The residue was purified by flash column chromatography on silica gel (Hex:EtOAc from 4:1 to 1:1) to yield 26a and 26b (1:2) as colourless oils (139 mg, in a combined 74% of yield).

$^1$H NMR (300 MHz, CDCl$_3$) mix of diastereoisomers δ 7.19-7.25 (m, 2H), 6.82-6.89 (m, 2H), 4.58-4.63 (m, 1H), 4.36-4.55 (m, 2H), 4.01-4.08 (m, 1H), 5.75-5.98 (m, 3H), 3.80 (s, 1.98H), 3.79 (s, 1.02H), 3.65 (s, 1.98H), 3.64 (s, 1-02H), 3.44-3.65 (m, 2H), 3.25-3.32 (m, 2H), 3.17 (s, 1.02H), 3.16 (s, 1.98H), 2.80-2.88 (m, 1H), 2.69 (d, J=9.3 Hz, 0.66H), 2.68 (d, J=9.0 Hz, 0.34H), 2.65-2.74 (m, 1H), 2.00-2.09 (m, 1H), 1.74-1.88 (m, 2H), 1.69 (br s, 1H), 1-34 (s, 1.02H), 1.25 (s, 1.98H), 1.07 (m, 3H), 0.92 (s, 5.94H), 0.90 (s, 3.06H), 0.89 (s, 3.06H), 0.88 (s, 5.94H), 0.85 (s, 3.06H), 0.83 (s, 5.94H), −0.02-0.18 (m, 18H).

MS (ESI) m/z: 880 (M+23)$^+$, 858 (M+1)$^+$.

R$_f$=0.09 (Hex:EtOAc, 4:1).

Example 61

Compounds 26c and 26d

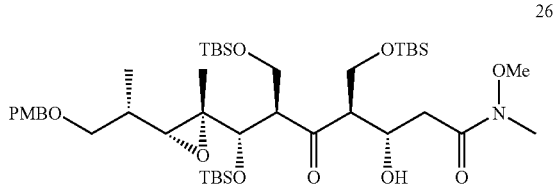

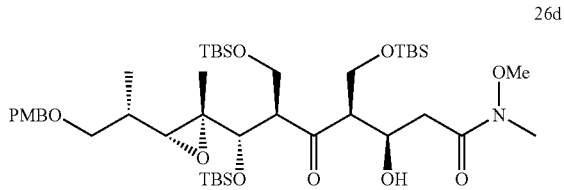

To a solution of N-methoxy-N-methylacetamide (568 µL g, 5.34 mmol) in THF (15 mL) at −78° C. was added bis-(trimethylsilyl)-lithiumamid (1.0 M in THF) (5.34 mL, 5.34 mmol) and the reaction mixture was stirred for 1 h at that temperature. Then, a solution of crude 25b (1.78 mmol) in THF (25 mL) was added over the previous solution and the reaction mixture was stirred for an additional 3 h at −78° C. Then, a saturated aqueous solution of NH$_4$Cl (50 mL) was added and the reaction was extracted with EtOAc (3×60 mL). The combined organic layers were dried over Na$_2$SO$_4$, filtered, and concentrated under reduced pressure. The residue was purified by flash column chromatography on silica gel (Hex:EtOAc from 4:1 to 2:1) to yield 26c and 26d (1:1.9) as colourless oils (910 mg, in a combined 60% of yield for two steps).

$^1$H NMR (300 MHz, CDCl$_3$) mix of diastereoisomers δ 7.25 (d, J=8.7 Hz, 4H), 6.88 (d, J=8.4 Hz, 4H), 4.64-4.60 (m, 1H), 4.48-4.36 (m, 6H), 4.10-3.82 (m, 6H), 3.80 (s, 6H), 3.76-3.71 (m, 2H), 3.66 (s, 6H), 3.61 (d, J=3.3 Hz, 1H), 3.53-3.48 (m, 2H), 3.44-3.29 (m, 6H), 3.18 (s, 6H), 3.01-2.80 (m, 3H), 2.61 (m, 1H), 2.57 (d, J=9.0 Hz, 1H), 2.53 (d, J=9.0 Hz, 1H), 1.81-1.67 (m, 2H), 1.32 (s, 3H), 1.31 (s, 3H), 1.05 (d, J=6.9 Hz, 6H), 0.89 (s, 18H), 0.87 (s, 9H), 0.86 (s, 9H), 0.85 (s, 9H), 0.84 (s, 9H), 0.1 (s, 6H), 0.07 (s, 9H), 0.06 (s, 3H), 0.02 (s, 3H), 0.01 (s, 6H), 0.00 (s, 3H), −0.01 (s, 3H), −0.01 (s, 3H).

$^{13}$C NMR (75 MHz, CDCl$_3$) δ 211.0, 172.4, 159.0, 130.1, 128.9, 113.6, 77.0, 72.6, 72.0, 71.9, 67.4, 66.1, 64.1, 64.0, 63.1, 63.0, 61.0, 60.8, 60.5, 60.1, 59.8, 58.9, 56.7, 55.1, 36.3, 33.5, 26.0, 25.7, 18.2, 18.0, 15.0, 12.5, −4.6, −4.7, −5.0, −5.1, −5.5, −5.6.

MS (ESI) m/z: 878 (M+23)$^+$.

R$_f$=0.44 (Hex:EtOAc, 2:1). Also R$_f$=0.16 (Hex:EtOAc, 4:1).

Example 62

Compounds 27a and 27b

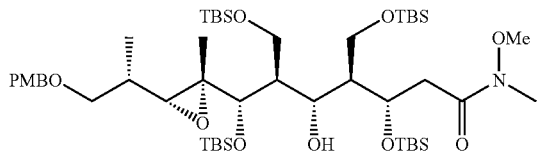

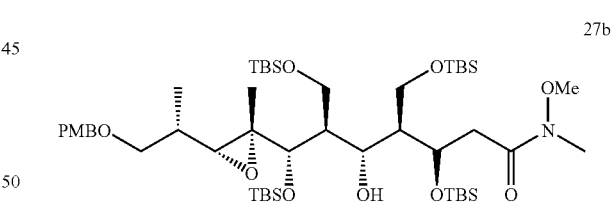

To a solution of a mixture of 26a and 26b (139 mg, 0.16 mmol) in CH$_2$Cl$_2$ (8 mL) was added 2,6-lutidine (57 µL, 0.49 mmol) and TBSOTf (56 µL, 0.24 mmol) at 0° C. The reaction mixture was stirred at 0° C. for 30 min. Then, a saturated aqueous solution of NH$_4$Cl (30 mL) was added, and the reaction was extracted with CH$_2$Cl$_2$ (2×25 mL). The combined organic layers were dried over Na$_2$SO$_4$, filtered, and concentrated under reduced pressure. The residue was purified by flash column chromatography on silica gel (Hex:EtOAc 10:1) to obtain 27a (white solid) and 27b (colourless oil) (1:2) (113 mg in a combined 72% of yield).

27a: $^1$H NMR (300 MHz, CDCl$_3$) δ 7.28 (d, J=8.7 Hz, 2H), 6.87 (d, J=8.7 Hz, 2H), 4.66 (brd, J=9.9 Hz, 1H), 4.50 (dd, J=11.7 Hz, 2H), 4.10 (brd, J=9.6 Hz, 1H), 3.92 (d, J=6.6 Hz, 2H), 3.80 (s, 3H), 3.66 (s, 3H), 3.64-3.59 (m, 2H), 3.42-3.85

(m, 1H), 3.35-3.32 (m, 1H), 3.15 (s, 3H), 3.01-2.96 (m, 1H), 2.74 (d, J=9.3 Hz, 1H), 2.70-2.67 (m, 1H), 2.08-2.03 (m, 1H), 1.92 (bs, 1H), 1.79-1.70 (m, 1H), 1.37 (s, 3H), 1.07 (d, J=6.6 Hz, 3H), 0.91 (s, 9H), 0.90 (s, 9H), 0.88 (s, 9H), 0.85 (s, 9H), 0.16 (s, 3H), 0.12 (s, 3H), 0.08 (s, 3H), 0.03 (s, 6H), 0.02 (s, 6H), 0.00 (s, 3H).

MS (ESI) m/z: 994 (M+23)$^+$.

$R_f$=0.34 (Hex:EtOAc, 4:1).

27b: $^1$H NMR (300 MHz, CDCl$_3$) δ 7.24 (d, J=8.7 Hz, 2H), 6.86 (d, J=8.7 Hz, 2H), 4.82-4.80 (m, 1H), 4.43 (q, J=11.4 Hz, 2H), 3.96-3.92 (m, 1H), 3.80 (s, 3H), 3.76-3.75 (m, 1H), 3.66 (s, 3H), 3.69-3.58 (m, 3H), 3.46 (dd, J=9.0, 6.3 Hz, 1H), 3.31 (dd, J=9.0, 7.2 Hz, 1H), 3.15 (s, 3H), 3.00-2.93 (m, 1H), 2.69 (d, J=8.7 Hz, 1H), 2.69-2.62 (m, 1H), 2.02-1.94 (m, 2H), 1.80-1.73 (m, 1H), 1.65 (s, 1H), 1.33 (s, 3H), 1.09 (d, J=6.6 Hz, 3H), 0.91 (s, 9H), 0.89 (s, 9H), 0.87 (s, 9H), 0.85 (s, 9H), 0.17 (s, 3H), 0.12 (s, 3H), 0.10 (s, 3H), 0.07 (s, 3H), 0.05 (s, 3H), 0.03 (s, 3H), 0.02 (s, 3H), 0.02 (s, 3H).

MS (ESI) m/z: 994 (M+23)$^+$.

$R_f$=0.46 (Hex:EtOAc, 4:1).

Example 63

Compound 27c

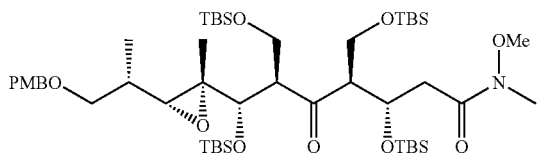

To a solution of 27a (36 mg, 0.04 mmol) in CH$_2$Cl$_2$ (4 mL) was added Dess-Martin periodinane (63 mg, 0.15 mmol) and catalytic amount of NaHCO$_3$ at 23° C. The reaction mixture was stirred at 23° C. for 1.5 h. Saturated aqueous solution of NaHCO$_3$ (10 mL) was added and the mixture was extracted with CH$_2$Cl$_2$ (3×10 mL). The combined organic layers were dried over Na$_2$SO$_4$, filtered, and concentrated under reduced pressure. The residue was purified by flash column chromatography on silica gel (Hex:EtOAc, 10:1) to obtain 27c (26 mg, 72%) as a pale yellow oil. This compound is also obtained by protection of 26c with TBSOTf and lutidine with a quantitative yield under standard condition.

$^1$H NMR (300 MHz, CDCl$_3$) δ 7.22 (d, J=8.7 Hz, 2H), 6.86 (d, J=8.7 Hz, 2H), 4.80-4.78 (m, 1H), 4.41 (q, J=11.4 Hz, 2H), 4.15 (d, J=4.5 Hz, 2H), 3.80 (s, 3H), 3.75-3.67 (m, 2H), 3.64 (s, 3H), 3.61-3.50 (m, 3H), 3.39 (dd, J=9.3, 7.2 Hz, 1H), 3.29 (dd, J=9.3, 6.6 Hz, 1H), 3.15 (bs, 3H), 2.99-2.96 (m, 1H), 2.67 (d, J=9.3 Hz, 1H), 2.54 (br d, J=5.1 Hz, 1H), 1.33 (s, 3H), 1.06 (d, J=6.3 Hz, 3H), 0.90 (s, 9H), 0.85 (s, 18H), 0.84 (s, 9H), 0.09 (s, 3H), 0.08 (s, 3H), 0.06 (s, 3H), 0.02 (s, 3H), 0.01 (s, 6H), −0.01 (s, 3H).

$^{13}$C NMR (75 MHz, CDCl$_3$), δ 210.2, 172.5, 159.1, 130.2, 128.9, 113.7, 76.1, 72.6, 72.1, 67.0, 64.0, 63.8, 61.5, 61.0, 60.8, 58.1, 55.1, 54.2, 36.7, 33.6, 29.6, 26.0, 25.9, 25.8, 25.7, 18.2, 18.1, 18.0, 17.9, 15.1, 13.4, −4.8, −4.9, −4.9, −5.4, −5.5, −5.5, −5.6.

MS (ESI) m/z: 992 (M+23)$^+$, 970 (M+1)$^+$.

$[\alpha]^{25}_D$−45.1 (c 0.50, CH$_3$Cl)

$R_f$=0.38 (Hex:EtOAc, 4:1). .

Example 64

Compound 27d

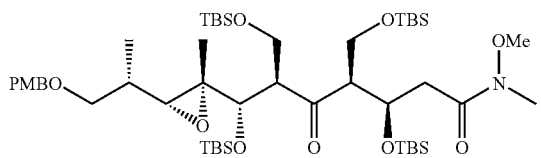

To a solution of 27b (77 mg, 0.08 mmol) in CH$_2$Cl$_2$ (3 mL) was added Dess-Martin periodinane (63 mg, 0.15 mmol) and catalytic amount of NaHCO$_3$ at 23° C. The reaction mixture was stirred at 23° C. for 1.5 h. Saturated aqueous solution of NaHCO$_3$ (10 mL) was added and the mixture was extracted with CH$_2$Cl$_2$ (3×10 mL). The combined organic layers were dried over Na$_2$SO$_4$, filtered, and concentrated under reduced pressure. The residue was purified by flash column chromatography on silica gel (Hex:EtOAc, 10:1) to obtain 27d (51 mg, 66%) as a pale yellow oil. This compound is also obtained by protection of 26d with TBSOTf and lutidine with a quantitative yield under standard condition.

$^1$H NMR (300 MHz, CDCl$_3$) δ 7.23 (d, J=8.7 Hz, 2H), 6.87 (d, J=8.7 Hz, 2H), 4.47 (d, J=12.0 Hz, 1H), 4.36 (d, J=12.0 Hz, 1H), 3.99-3.83 (m, 3H), 3.80 (s, 3H), 3.69-3.58 (m, 2H), 3.68 (s, 3H), 3.42-3.36 (m, 2H), 3.26 (dd, J=9.3, 6.3 Hz, 1H), 3.17 (bs, 3H), 3.07 (dt, J=9.3, 3.3 Hz, 1H), 2.90-2.87 (m, 1H), 2.59 (d, J=9.0 Hz, 1H), 2.17 (br d, J=14.1 Hz, 1H), 1.31 (s, 3H), 1.05 (d, J=6.6 Hz, 3H), 0.90 (s, 9H), 0.88 (s, 9H), 0.85 (s, 9H), 0.84 (s, 9H), 0.18 (s, 3H), 0.12 (s, 3H), 0.08 (s, 3H), 0.07 (s, 3H), 0.06 (s, 3H), −0.01 (s, 6H), −0.02 (s, 3H).

$^{13}$C NMR (75 MHz, CDCl$_3$) δ 209.2, 172.1, 159.2, 130.2, 129.0, 113.8, 76.3, 72.5, 71.8, 68.2, 64.2, 63.0, 61.3, 60.9, 60.0, 59.3, 57.7, 55.1, 36.4, 34.0, 29.6, 26.4, 25.9, 25.8, 25.7, 18.7, 18.1, 17.9, 15.3, 12.4, −4.3, −4.4, −5.1, −5.2, −5.5, −5.6, −5.7.

MS (ESI) m/z: 992 (M+23)$^+$.

$[\alpha]^{25}_D$+47.6 (c 0.5, CH$_3$Cl).

$R_f$=0.45 (Hex:EtOAc, 4:1).

Example 65

Compound 28a

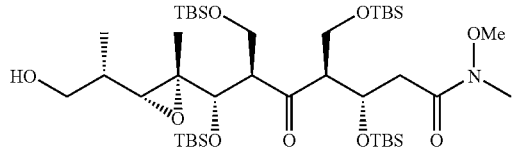

To a solution of 27c (390 mg, 0.4 mmol) in a mixture of CH$_2$Cl$_2$:H$_2$O (4:0.2 mL) was added 2,3-dichloro-5,6-dicyano-1,4-benzoquinone (274 mg, 1.2 mmol) at 23° C. The reaction mixture was stirred at 23° C. for 18 min. Saturated aqueous solution of NaHCO$_3$ (15 mL) was added and the mixture was extracted with CH$_2$Cl$_2$ (3×15 mL). The combined organic layers were dried over Na$_2$SO$_4$, filtered, and concentrated under reduced pressure. The residue was solved in MeOH and NaBH$_4$ (74 mg, 2 mmol) was added and the reaction was stirred at 23° C. for 30 min. Then, the reaction was concentrated under reduced pressure. A saturated aqueous solution of NaHCO$_3$ (20 mL) was added and the mixture was extracted with CH$_2$Cl$_2$ (3×30 mL). The combined organic layers were dried over Na$_2$SO$_4$, filtered, and concentrated under reduced pressure. The residue was purified by flash column chromatography on silica gel (Hex:EtOAc, 4:1) to obtain 28a (220 mg, 65%) as a white solid.

$^1$H NMR (300 MHz, CDCl$_3$) δ 4.77-4.72 (m, 1H), 4.10-3.99 (m, 2H), 3.86-3.84 (m, 2H), 3.65 (s, 3H), 3.62-3.59 (m, 1H), 3.56-3.48 (m, 3H), 3.15 (s, 3H), 2.99-2.95 (m, 1H), 2.76-2.75 (m, 1H), 2.58-2.55 (m, 1H), 2.52 (br d, J=3.3 Hz, 1H), 2.46 (d, J=9.3 Hz, 1H), 1.67 (bs, 1H), 1.37 (s, 3H), 1.01 (d, J=6.9 Hz, 3H), 0.90 (s, 9H), 0.89 (s, 9H), 0.86 (s, 9H), 0.85 (s, 9H), 0.12 (s, 3H), 0.11 (s, 3H), 0.08 (s, 3H), 0.07 (s, 3H), 0.06 (s, 3H), 0.03 (s, 3H), 0.02 (s, 3H), 0.01 (s, 3H).

$^{13}$C NMR (75 MHz, CDCl$_3$) δ 211.8, 172.1, 76.9, 67.1, 65.1, 64.8, 63.4, 61.5, 61.2, 61.1, 58.5, 57.3, 36.6, 35.8, 32.0, 29.6, 26.0, 25.9, 25.8, 25.7, 18.2, 18.1, 17.9, 14.3, 13.7, −4.6, −4.8, −5.2, −5.4, −5.5, −5.6.

MS (ESI) m/z: 872 (M+23)$^+$.

[α]$^{25}_D$ −32.9 (c 0.50, CH$_3$Cl).

R$_f$=0.31 (Hex:EtOAc, 4:1).

Example 66

Compound 28b

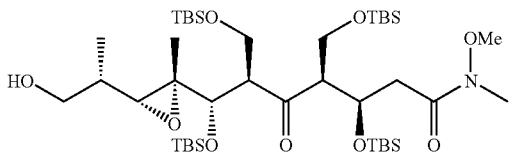

To a solution of 27d (718 mg, 0.74 mmol) in a mixture of CH$_2$Cl$_2$:H$_2$O (10:0.5 mL) was added 2,3-dichloro-5,6-dicyano-1,4-benzoquinone (504 mg, 2.22 mmol) at 23° C. The reaction mixture was stirred at 23° C. for 17 min. Saturated aqueous solution of NaHCO$_3$ (15 mL) was added and the mixture was extracted with CH$_2$Cl$_2$ (3×15 mL). The combined organic layers were dried over Na$_2$SO$_4$, filtered, and concentrated under reduced pressure. The residue was solved in MeOH and NaBH$_4$ (110 mg, 3 mmol) was added and the reaction was stirred at 23° C. for 20 min. Then, the reaction was concentrated under reduced pressure. A saturated aqueous solution of NaHCO$_3$ (20 mL) was added and the mixture was extracted with CH$_2$Cl$_2$ (3×30 mL). The combined organic layers were dried over Na$_2$SO$_4$, filtered, and concentrated under reduced pressure. The residue was purified by flash column chromatography on silica gel (Hex:EtOAc, 4:1) to obtain 28b (374 mg, 60%) as a white solid.

$^1$H NMR (300 MHz, CDCl$_3$) δ 4.75-4.72 (m, 1H), 4.02-3.92 (m, 2H), 3.88 (dd, J=10.5, 3.9 Hz, 1H), 3.71-3.65 (m, 1H), 3.67 (s, 3H), 3.61-3.54 (m, 2H), 3.49 (d, J=6.3 Hz, 1H), 3.45-3.39 (m, 1H), 3.16 (bs, 3H), 3.13-3.08 (m, 1H), 2.84 (br dd, J=15.9, 8.7 Hz, 1H), 2.48 (d, J=9.0 Hz, 1H), 2.46-2.44 (m, 1H), 1.72-1.67 (m, 1H), 1.31 (s, 3H), 1.09 (d, J=6.6 Hz, 3H), 0.90 (s, 9H), 0.89 (s, 9H), 0.86 (s, 9H), 0.85 (s, 9H), 0.16 (s, 3H), 0.12 (s, 3H), 0.09 (s, 3H), 0.08 (s, 3H), 0.07 (s, 3H), 0.06 (s, 3H), 0.02 (s, 3H), 0.01 (s, 3H).

$^{13}$C NMR (75 MHz, CDCl$_3$) δ 212.6, 172.0, 76.4, 67.6, 65.2, 65.0, 62.9, 61.2, 61.1, 60.8, 59.9, 59.5, 37.1, 36.2, 32.0, 29.6, 26.0, 25.9, 25.8, 25.6, 18.3, 18.1, 18.0, 18.0, 14.4, 13.5, −3.6, 4.4, −4.8, −4.9, −5.0, −5.5, −5.6, −5.7.

MS (ESI) m/z: 872 (M+23)$^+$.

[α]$^{25}_D$ +21.6 (c 0.52, CH$_3$Cl)

R$_f$=0.31 (Hex:EtOAc, 4:1). .

Example 67

Compound 29a

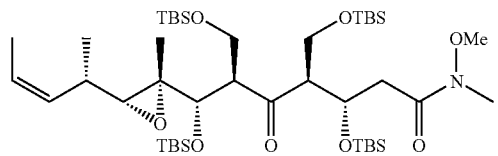

To a solution of 28a (162 mg, 0.19 mmol) in CH$_2$Cl$_2$ (5 mL) was added Dess-Martin periodinane (202 mg, 0.47 mmol) and catalytic amount of NaHCO$_3$ at 23° C. The reaction mixture was stirred at 23° C. for 40 min. A saturated aqueous solution of NaHCO$_3$ (15 mL) was added and the mixture was extracted with CH$_2$Cl$_2$ (3×20 mL). The combined organic layers were dried over Na$_2$SO$_4$, filtered, and concentrated under reduced pressure to give the corresponding aldehyde (R$_f$=0.32, Hex:EtOAc, 4:1). Meanwhile, to a suspension of ethyl triphenylphosphonium bromide (565 mg, 1.94 mmol) in toluene (7 mL) was added potassium t-butoxide (1.24 mL, 1.0 M in THF, 1.24 mmol) at 0° C. The resulting orange solution was stirred at 0° C. for 25 min and then cooled to −78° C. Then, a solution of the fresh crude aldehyde in toluene (5 mL) was added dropwise to the previous suspension at −78° C. and the mixture was allowed to reach 23° C. during 14 h. The reaction mixture was diluted with CH$_2$Cl$_2$ (20 mL) and washed with a saturated NaHCO$_3$ solution (30 mL). The organic phase was dried over MgSO4, filtered, and concentrated in vacuo. The residue was purified by flash column chromatography on silica gel (Hex:EtOAc, from 20:1) to obtain 29a (105 mg, 64% for 2 steps) as a white solid.

$^1$H NMR (300 MHz, CDCl$_3$) δ 5.52-5.46 (m, 1H), 5.26-5.19 (m, 1H), 4.88-4.87 (m, 1H), 4.20-4.09 (m, 2H), 3.70-3.65 (m, 1H), 3.64 (s, 3H), 3.60-3.57 (m, 3H), 3.42 (d, J=8.4 Hz, 1H), 3.15 (bs, 3H), 2.79-2.75 (m, 1H), 2.58 (d, J=9.6 Hz, 1H), 2.43-2.39 (m, 2H), 1.62 (dd, J=6.6, 1.5 Hz, 3H), 1.29 (s, 3H), 1.10 (d, J=6.6 Hz, 3H), 0.91 (s, 9H), 0.86 (s, 9H), 0.85 (s, 9H), 0.84 (s, 9H), 0.10 (s, 3H), 0.09 (s, 6H), 0.08 (s, 3H), 0.01 (s, 3H), 0.00 (s, 3H), −0.01 (s, 3H), −0.02 (s, 3H).

$^{13}$C NMR (75 MHz, CDCl$_3$) δ 211.0, 171.9, 130.5, 124.0, 66.6, 64.8, 62.6, 61.9, 61.6, 60.6, 57.0, 53.7, 36.2, 31.1, 29.2, 25.7, 25.5, 25.4, 25.3, 18.4, 17.8, 17.7, 17.6, 12.7, 11.8, −5.1, −5.2, −5.3, −5.4, −5.8, −5.9, −6.0.

MS (ESI) m/z: 882 (M+23)$^+$.

[α]$^{25}_D$ −6.1 (c 0.50, CH$_2$Cl$_2$).

R$_f$=0.44 (Hex:EtOAc, 4:1).

Example 68

Compound 29b

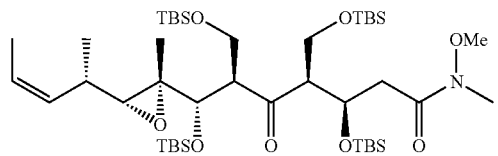

To a solution of 28b (318 mg, 0.37 mmol) in CH$_2$Cl$_2$ (8 mL) was added Dess-Martin periodinane (397 mg, 0.93 mmol) and catalytic amount of NaHCO$_3$ at 23° C. The reaction mixture was stirred at 23° C. for 40 min. A saturated aqueous solution of NaHCO$_3$ (30 mL) was added and the mixture was extracted with CH$_2$Cl$_2$ (3×40 mL). The combined organic layers were dried over Na$_2$SO$_4$, filtered, and concentrated under reduced pressure to give the corresponding aldehyde (R$_f$=0.42, Hex:EtOAc, 4:1). Meanwhile, to a suspension of ethyl triphenylphosphonium bromide (1.1 g, 3.77 mmol) in toluene (12 mL) was added potassium t-butoxide (2.43 mL, 1M in THF, 2.34 mmol) at 0° C. The resulting orange solution was stirred at 0° C. for 25 min and then cooled to −78° C. Then, a solution of the fresh crude aldehyde in toluene (6 mL) was added dropwise to the previous suspension at −78° C. and the mixture was allowed to reach 23° C. during 15 h. The reaction mixture was diluted with CH$_2$Cl$_2$ (20 mL) and washed with a saturated NaHCO$_3$ solution (30 mL). The organic phase was dried over MgSO4, filtered, and concentrated in vacuo. The residue was purified by flash column chromatography on silica gel (Hex:EtOAc 20:1) to obtain 29b (195 mg, 60% for 2 steps) as a white solid.

$^1$H NMR (300 MHz, CDCl$_3$) δ 5.50-5.42 (m, 1H), 5.29-5.25 (m, 1H), 4.81-4.78 (m, 1H), 3.93 (dd, J=11.4, 3.6 Hz, 1H), 3.81 (m, 2H), 3.67 (s, 3H), 3.64-3.56 (m, 2H), 3.43-3.39 (m, 1H), 3.17 (bs, 3H), 3.03-3.00 (m, 1H), 2.96-2.88 (m, 1H), 2.65 (d, J=9.0 Hz, 1H), 2.46-2.35 (m, 1H), 2.10 (br d, J=14.7 Hz, 1H), 1.61 (dd, J=6.9, 1.8 Hz, 1H), 1.28 (s, 3H), 1.11 (d, J=6.9 Hz, 3H), 0.90 (s, 9H), 0.87 (s, 9H), 0.85 (s, 9H), 0.84 (s, 9H), 0.18 (s, 3H), 0.14 (s, 3H), 0.08 (s, 3H), 0.06 (s, 3H), 0.01 (s, 3H), −0.02 (s, 3H), −0.03 (s, 3H).

$^{13}$C NMR (75 MHz, CDCl$_3$) δ 209.0, 172.0, 131.0, 124.2, 76.3, 68.1, 65.0, 62.6, 61.4, 61.3, 59.6, 59.4, 57.2, 36.3, 31.8, 29.7, 26.4, 25.9, 25.8, 25.7, 18.9, 18.7, 18.1, 18.0, 17.9, 13.2, 11.9, −4.3, −4.4, −5.1, −5.2, −5.4, −5.5, −5.6.

MS (ESI) m/z: 882 (M+23)$^+$.

[α]$^{25}$$_D$+70.2 (c 0.50, CH$_2$Cl$_2$).

R$_f$=0.77 (Hex:EtOAc, 4:1).

Example 69

Compound 30a

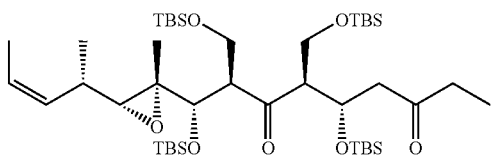

To a solution of 29a (80 mg, 0.093 mmol) in THF (1.5 mL) was added BrMgEt (0.28 mL, 1M in THF, 0.28 mmol) at 23° C. The reaction mixture was stirred at 23° C. for 3 h. Saturated aqueous solution of NaHCO$_3$ (10 mL) was added and the mixture was extracted with CH$_2$Cl$_2$ (3×15 mL). The combined organic layers were dried over Na$_2$SO$_4$, filtered, and concentrated under reduced pressure. The residue was purified by flash column chromatography on silica gel (Hex: EtOAc, 20:1) to obtain 30a (54 mg, 71%) as a white solid.

$^1$H NMR (300 MHz, CDCl$_3$) δ 5.54-5.44 (m, 1H), 5.26-5.18 (m, 1H), 4.83 (ddd, J=9.6, 4.2, 21. Hz, 1H), 4.13 (dd, J=9.6, 7.2 Hz, 1H), 4.05 (dd, J=9.6, 3.9 Hz, 1H), 3.67 (dd, J=8.7, 6.6 Hz, 1H), 3.59-3.57 (m, 2H), 3.38 (d, J=9.0 Hz, 1H), 2.75-70 (m, 1H), 2.55 (d, J=9.3 Hz, 1H), 2.46-2.43 (m, 5H), 1.62 (dd, J=6.6, 1.8 Hz, 3H), 1.28 (s, 3H), 1.10 (d, J=6.3 Hz, 3H), 1.01 (t, J=7.2 Hz, 3H), 0.91 (s, 9H), 0.86 (s, 9H), 0.85 (s, 9H), 0.82 (s, 9H), 0.10 (s, 3H), 0.09 (s, 6H), 0.08 (s, 3H), 0.01 (s, 3H), 0.00 (s, 3H), −0.01 (s, 3H), −0.03 (s, 3H).

$^{13}$C NMR (75 MHz, CDCl$_3$) δ 212.5, 209.2, 131.1, 124.7, 78.2, 66.6, 65.5, 63.2, 62.6, 62.4, 57.5, 54.3, 53.6, 47.3, 36.7, 31.8, 29.9, 26.3, 26.1, 26.0, 19.0, 18.5, 18.3, 18.2, 13.4, 12.4, 7.8, −4.3, −4.4, −4.7, −4.8, −5.1, −5.2, −5.3.

MS (ESI) m/z: 851 (M+23)$^+$.

[α]$^{25}$$_D$−25.4 (c 0.50, CH$_2$Cl$_2$).

R$_f$=0.86 (Hex:EtOAc, 4:1).

Example 70

Compound 30b

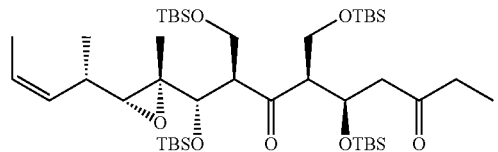

To a solution of 29b (110 mg, 0.13 mmol) in THF (1.5 mL) was added BrMgEt (0.38 mL, 1M in THF, 0.38 mmol) at 23° C. The reaction mixture was stirred at 23° C. for 4 h. Saturated aqueous solution of NaHCO$_3$ (10 mL) was added and the mixture was extracted with CH$_2$Cl$_2$ (3×15 mL). The combined organic layers were dried over Na$_2$SO$_4$, filtered, and concentrated under reduced pressure. The residue was purified by flash column chromatography on silica gel (Hex: EtOAc, 20:1) to obtain 30b (70 mg, 65%) as a colourless oil.

$^1$H NMR (300 MHz, CDCl$_3$) δ 5.52-5.41 (m, 1H), 5.28-5.20 (m, 1H), 4.76-4.72 (m, 1H), 3.85-3.73 (m, 3H), 3.70 (d, J=10.2 Hz, 1H), 3.48-3.41 (m, 2H), 3.05-3.00 (dt, J=10.2, 3.3 Hz, 1H), 2.80 (dd, J=15.6, 10.5 Hz, 1H), 2.64 (d, J=9.3 Hz, 1H), 2.45-2.40 (m, 3H), 2.38-2.12 (m, 1H), 1.61 (dd, J=6.9, 1.8 Hz, 3H), 1.29 (s, 3H), 1.11 (d, J=6.3 Hz, 3H), 1.01 (t, J=7.2 Hz, 3H), 0.89 (s, 18H), 0.84 (s, 18H), 0.19 (s, 3H), 0.14 (s, 3H), 0.05 (s, 3H), 0.03 (s, 6H), 0.01 (s, 3H), 0.00 (s, 3H), −0.04 (s, 3H).

$^{13}$C NMR (75 MHz, CDCl$_3$) δ 209.5, 209.3, 131.0, 124.3, 76.0, 67.6, 64.9, 62.4, 61.3, 59.8, 58.9, 57.3, 45.5, 38.1, 31.9, 29.7, 26.3, 25.9, 25.8, 25.7, 19.0, 18.7, 18.1, 18.0, 17.8, 13.3, 11.9, 7.4, −4.1, −4.2, −5.1, −5.2, −5.4, −5.5, −5.6, −5.7.

MS (ESI) m/z: 851 (M+23)$^+$.

[α]$^{25}$$_D$+80.9 (c 0.50, CH$_2$Cl$_2$).

R$_f$=0.71 (Hex:EtOAc, 4:1).

Example 71

Compounds 31a and 31c

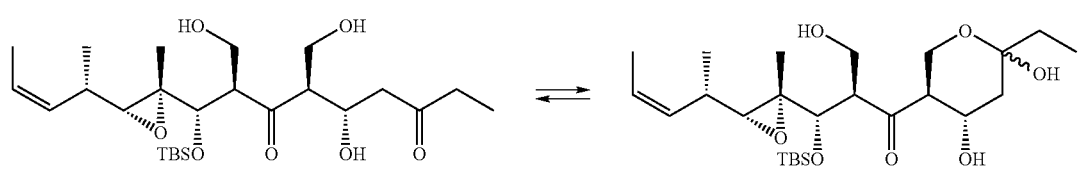

Following the procedure described in example 50, 30a (48 mg, 0.058 mmol) was converted to a tautomer equilibrium of 31a and 31c (20 mg, 70%, colourless oil) after purification of the crude product by flash column chromatography (Hex:EtOAc from 4:1 to 1:1).

¹H NMR (500 MHz, CDCl₃) (data of the major product) d 5.55-5.49 (m, 1H), 5.29-5.24 (m, 1H), 4.28 (ddd, J=15.5, 11.0, 4.5 Hz, 1H), 3.97 (dd, J=11.5, 11.5 Hz, 2H), 3.76 (dd, J=11.5, 3.5 Hz, 1H), 3.67-3.65 (m, 1H), 3.62 (d, J=10.0 Hz, 1H), 3.35-3.31 (m, 1H), 2.86-2.80 (m, 1H), 2.60 (d, J=9.0 Hz, 1H), 2.44-2.37 (m, 1H), 2.09 (dd, J=12.5, 4.5 Hz, 1H), 1.70-1.65 (m, 2H), 1.62 (dd, J=7.0, 2.0 Hz, 3H), 1.45 (br t, J=11.5 Hz, 1H), 1.30 (s, 3H), 1.11 (d, J=7.0 Hz, 3H), 0.96 (t, J=7.5 Hz, 3H), 0.89 (s, 9H), 0.16 (s, 3H), 0.05 (s, 3H).

¹³C NMR (125 MHz, CDCl₃) (data of the major product) δ 214.7, 130.5, 124.8, 98.7, 78.2, 66.9, 65.0, 61.8, 60.5, 59.6, 59.2, 57.7, 39.9, 35.6, 31.4, 26.1, 18.7, 18.4, 13.3, 11.6, 7.4, −4.4, −4.7.

MS (ESI) m/z: 509 (M+23)⁺, 451 (M+1-2×H₂O)⁺.
$R_f$=0.4 (Hex:EtOAc, 1:2).

Example 72

Compounds 31b and 31d

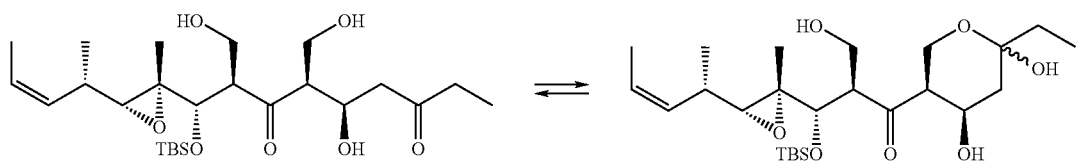

Following the procedure described in example 50, 30b (45 mg, 0.054 mmol) was converted to a tautomer equilibrium of 31b and 31d (13 mg, 50%, colourless oil) after purification of the crude product by flash column chromatography (Hex:EtOAc from 4:1 to 1:1).

¹H NMR (500 MHz, CDCl₃) (data of the major product) δ 5.59-5.46 (m, 1H), 5.28 (m, 1H), 4.62 (bs, 1H), 4.22 (dd, J=11.5, 11.5 Hz, 1H), 4.10 (dd, J=12.0, 5.0 Hz), 3.70-3.60 (m, 2H), 3.48 (d, J=10.0 Hz, 1H), 3.24-3.17 (m, 1H), 2.94 (ddd, J=11.5, 5.0, 2.0 Hz, 1H), 2.61 (d, J=9.5 Hz, 1H), 2.47-2.41 (m, 1H), 2.03 (dd, J=14.5, 3.5 Hz,), 1.66 (dd, J=7.0, 1.5 Hz, 3H), 1.63-1.61 (m, 2H), 1.58 (dd, J=14.0, 3.0 Hz, 1H), 1.32 (s, 3H), 1.14 (d, J=6.0 Hz, 3H), 0.97 (t, J=7.5 Hz, 3H), 0.87 (s, 9H), 0.15 (s, 3H), 0.00 (s, 3H).

¹³C NMR (125 MHz, CDCl₃) (data of the major product) δ 216.3, 130.5, 124.9, 97.2, 78.4, 65.9, 65.2, 62.0, 60.7, 55.7, 55.4, 54.7, 37.1, 34.2, 31.4, 26.0, 18.7, 18.2, 13.3, 11.4, 7.4, −4.3, −5.2.

MS (ESI) m/z: 509 (M+23)⁺, 451 (M+1-2×H₂O)⁺.
$R_f$=0.42 (Hex:EtOAc, 1:2).

Example 73

Compounds 3c and 4c

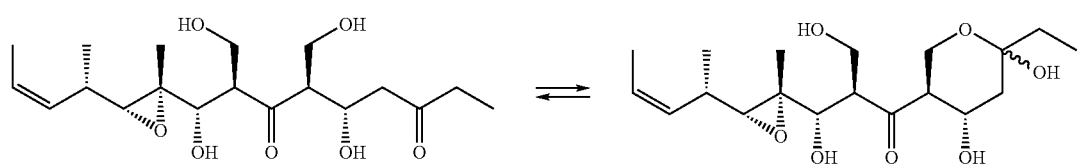

Following the procedure described in example 52, 31a (48 mg, 0.058 mmol) was converted to a tautomer equilibrium of 3c and 4c (5 mg, 22%) after purification of the crude product by flash column chromatography (Hex:EtOAc from 4:1 to 0:1).

¹H NMR (500 MHz, CDCl₃) (data of the major product) δ 5.56-5.49 (m, 1H), 5.28-5.23 (m, 1H), 4.36 (ddd, J=15.0, 11.0, 5.0 Hz, 1H), 3.97-3.66 (m, 4H), 3.62 (d, J=10.0 Hz, 1H), 3.25-3.18 (m, 1H), 2.98 (ddd, J=14.0, 10.0, 4.0 Hz, 1H), 2.78 (d, J=9.0 Hz, 1H), 2.45-2.40 (m, 1H), 2.09 (dd, J=13.0, 5.0 Hz, 1H), 1.67 (q, J=7.5 Hz, 2H), 1.63 (dd, J=1.5 Hz, 7 Hz, 3H), 1.48-1.42 (m, 1H), 1.33 (s, 3H), 1.12 (d J=7.0 Hz, 3H), 0.96 (t, J=7.5 Hz, 3H).

¹³C NMR (125 MHz, CDCl₃) (data of the major product) δ 215.4, 130.0, 125.0, 98.7, 77.3, 67.0, 62.8, 60.8, 60.0, 59.0, 40.1, 35.5, 31.3, 23.9, 19.7, 18.6, 13.3, 11.3, 7.4.

MS (ESI) m/z: 767 (2×M+23)⁺, 395 (M+23)⁺, 337 (M+1-2×H₂O)⁺.

$R_f$=0.16 (Hex:EtOAc, 1:2).

Example 74

Compounds 3d and 4d

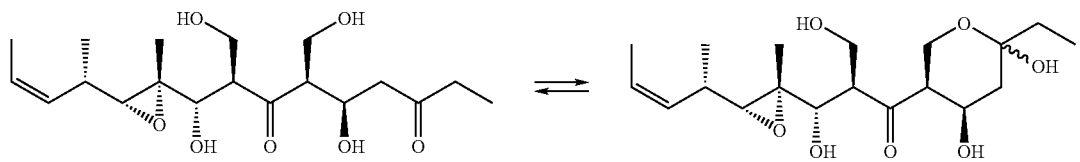

Following the procedure described in example 52, 31b (150 mg, 0.18 mmol) was converted to a tautomer equilibrium of 3d and 4d (10 mg, 15%) after purification of the crude product by flash column chromatography (Hex:EtOAc from 4:1 to 0:1).

$^1$H NMR (500 MHz, CH$_3$OD) (data of the major product) δ 5.57-5.51 (m, 1H), 5.32-5.26 (m, 1H), 4.80 (m, 1H), 4.26 (dd, J=11.5, 11.5 Hz, 1H), 3.98-3.60 (m, 3H), 3.31-3.29 (m, 1H), 3.24 (d, J=10 Hz, 1H), 2.80 (ddd, J=11.5, 4.5, 2.5 Hz, 1H), 2.59 (d, J=9.5 Hz, 1H), 1.95 (dd, J=14.0, 3.5 Hz, 1H), 1.75 (dd, J=14.5, 3.0 Hz, 1H), 1.65 (dd, J=6.5, 15. Hz, 3H), 1.56 (q, J=7.5 Hz, 2H), 1.34 (s, 3H), 1.10 (d, J=7.0 Hz, 3H), 0.92 (t, J=7.5 Hz, 3H).

$^1$H NMR (500 MHz, CDCl$_3$) (data of the major product) δ 5.56-5.50 (m, 1H), 5.36 (s, 1H), 5.27-5.21 (m, 1H), 4.76 (bs, 1H), 4.29 (dd, J=11.5, 11.5 Hz, 1H), 3.87 (dd, J=12.5, 4.0 Hz, 1H), 3.73-3.62 (m, 3H), 3.46 (d, J=10.0 Hz, 1H), 2.90 (ddd, J=11.5, 4.5, 2.0 Hz, 1H), 2.74 (d, J=9.5 Hz, 1H), 2.01 (dd, J=13.5, 3.5 Hz, 1H), 1.70 (dd, J=14.0, 2.5 Hz, 1H), 1.62 (dd, J=7.0, 2.0 Hz, 3H), 1.61-1.59 (m, 2H), 1.34 (s, 3H), 1.11 (d, J=6.5 Hz, 3H), 0.95 (t, J=7.0 Hz, 3H).

$^{13}$C NMR (125 MHz, CDCl$_3$) (data of the major product) δ 214.9, 130.0, 125.1, 96.9, 77.1, 67.1, 65.4, 62.8, 60.9, 55.3, 54.9, 52.7, 37.4, 34.2, 31.3, 18.6, 13.3, 11.4, 7.5.

MS (ESI) m/z: 767.2 (2×M+23)$^+$, 395.3 (M+23)$^+$, 377.3 (M+23−H$_2$O)$^+$, 337 (M+1−2×H$_2$O)$^+$, 319.3 (M+1−3×H$_2$O)$^+$.

R$_f$=0.22 (Hex:EtOAc, 1:2).

Example 75

Compound 32

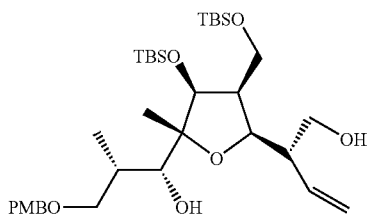

This compound was obtained as a side product in the preparation of 34 from 11a. To a solution of 11a (1.72 g, 2.69 mmol) in acetone (10 mL) was added dimethoxypropane (10 mL) and camphorsulfonic acid (94 mg, 0.4 mmol) and the mixture was stirred for 1 h at 23° C. (until TLC revealed total consumption of the starting material). Et$_3$N (0.56. mL, 4 mmol) was then added and the mixture was stirred for 30 min. Solvents were removed under reduced pressure and the mixture was subjected to flash column chromatography on silica gel (Hex:EtOAc, from 10:1 to 3:1) affording furano 32 (0.6 g, 35%) as a colourless oil.

$^1$H NMR (300 MHz, CDCl$_3$) δ 7.23 (d, J=8.8 Hz, 2H), 6.87 (d, J=8.8 Hz, 2H), 5.72-5.65 (m, 1H), 5.09-5.06 (m, 2H), 4.42 (s, 2H), 4.44-4.39 (m, 1H), 3.90 (dd, J=10.0, 2.0 Hz, 1H), 3.84-3.78 (m, 2H), 3.80 (s, 3H), 3.60 (dd, J=6.0, 5.5 Hz, 1H), 3.51-3.42 (m, 3H), 3.36-3.32 (m, 2H), 2.76-2.73 (m, 1H), 2.63-2.58 (m, 1H), 2.13-2.09 (m, 1H), 1.98 (d, J=4.5 Hz, 1H), 1.02 (d, J=6.8 Hz, 3H), 0.99 (s, 3H), 0.92 (s, 9H), 0.90 (s, 9H), 0.11 (s, 3H), 0.10 (s, 3H), 0.09 (s, 3H), 0.07 (s, 3H).

$^{13}$C NMR (75 MHz, CDCl$_3$) δ 159.1, 137.4, 130.5, 129.1, 116.3, 113.7, 83.6, 78.7, 77.7, 77.1, 75.4, 72.7, 64.9, 58.6, 55.2, 49.6, 34.4, 25.8, 25.7, 18.1, 18.0, 17.5, 12.5, −4.7, −5.1, −5.5, −5.6.

MS (ESI) m/z: 661.4 (M+23)$^+$.

R$_f$=0.35 (Hex:EtOAc, 4:1).

Example 76

Compounds 33 and 42

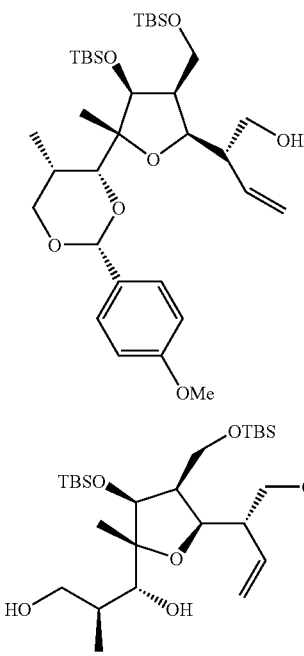

To a solution of furane 32 (246 mg, 0.346 mmol) in CH$_2$Cl$_2$ (10 mL) and water (0.5 mL) was added 2,3-dichloro-5,6-dicyano1,4-benzoquinone (236 mg, 1.04 mmol) and the reaction mixture was vigorously stirred for 1 h at 23° C. The reaction was hydrolysed by addition of aqueous NaHCO$_3$ (20 mL) and the solution was extracted with CH$_2$Cl$_2$ (2×20 mL).

The combined organic layers were dried over $Na_2SO_4$, filtered and concentrated in vacuo. The residue was dissolved in MeOH (5 mL) and treated with $NaBH_4$ (30 mg) for 30 min at 23° C. After this time, solvents were removed under reduced pressure, and the residue was dissolved in $CH_2Cl_2$, hydrolysed with aqueous $NH_4Cl$ and extracted with $CH_2Cl_2$ (2×20 mL). The combined organic layers were dried over $Na_2SO_4$, filtered and concentrated in vacuo. The residue was purified by flash column chromatography on silica gel (Hex:EtOAc, from 4:1 to 2:1) to obtain compounds 33 (88 mg, 40%) and 42 (77 mg, 42%) as colourless oils.

33: $^1$H NMR (300 MHz, $CDCl_3$) δ 5.82-5.75 (m, 1H), 5.46 (s, 1H), 5.13-5.09 (s, 2H), 4.48 (d, J=6.5 Hz, 1H), 4.07-4.04 (m, 1H), 3.99 (dd, J=4.5, 4.0 Hz, 1H), 3.97-3.94 (m, 1H), 3.91 (d, J=2.5 Hz, 1H), 3.88-3.79 (m, 2H), 3.81 (s, 3H), 3.62 (dd, J=6.0, 5.0 Hz, 1H), 3.50-3.43 (m, 1H), 3.28-3.22 (m, 1H), 2.76-2.67 (m, 2H), 1.76-1.71 (m, 1H), 1.26 (d, J=7.0 Hz, 3H), 1.08 (s, 3H), 0.91 (s, 9H), 0.87 (s, 9H), 0.10 (s, 3H), 0.08 (s, 3H), 0.04 (s, 3H), −0.07 (s, 3H).

$^{13}$C NMR (75 MHz, $CDCl_3$) δ 159.8, 137.4, 131.3, 127.4, 116.3, 113.5, 102.1, 86.4, 83.4, 79.4, 77.0, 75.4, 65.1, 58.7, 55.2, 49.9, 46.2, 30.6, 29.7, 25.8, 18.6, 18.1, 13.3, −4.3, −5.2, −5.4, −5.5.

MS (ESI) m/z: 659.2 $(M+23)^+$.

$R_f$=0.31 (Hex:EtOAc, 4:1).

42: $^1$H NMR (300 MHz, $CDCl_3$) δ 5.68-5.55 (m, 1H), 5.18-5.12 (m, 2H), 4.41 (d, J=6.7 Hz, 1H), 3.94-3.77 (m, 3H), 3.70-3.36 (m, 3H), 3.14 (d, J=8.6 Hz, 1H), 2.82-2.77 (m, 1H), 2.64-2.59 (m, 1H), 2.04-2.03 (m, 1H), 1.89-1.82 (m, 1H), 1.04 (s, 3H), 0.97 (d, J=6.7 Hz, 3H), 0.92 (s, 9H), 0.90 (s, 9H), 0.13 (s, 3H), 0.11 (s, 6H), 0.09 (s, 3H).

$^{13}$C NMR (75 MHz, $CDCl_3$) δ 136.3, 118.4, 82.9, 80.3, 79.7, 79.1, 66.4, 64.7, 58.4, 49.5, 47.0, 39.1, 26.1, 26.0, 18.4, 18.3, 16.5, 15.2, −4.4, −5.0, −5.2, −5.3.

MS (ESI) m/z: 541.2 $(M+23)^+$, 519.3 $(M+1)^+$.

$R_f$=0.06 (Hex:EtOAc, 4:1).

Example 77

Compound 34

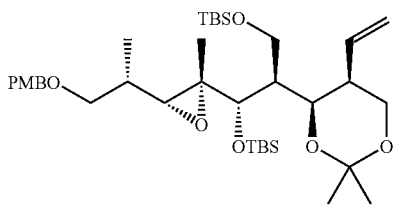

To a solution of 11a (1.72 g, 2.69 mmol) in acetone (10 mL) was added dimethoxypropane (10 mL) and camphorsulfonic acid (94 mg, 0.4 mmol) and the mixture was stirred for 1 h at 23° C. (until TLC revealed total consumption of the starting material). $Et_3N$ (0.56 mL, 4 mmol) was then added and the mixture was stirred for 30 min. Solvents were removed under reduced pressure and the mixture was subjected to flash column chromatography on silica gel (Hex:EtOAc, from 10:1 to 3:1) affording acetonide 34 (1.16 g mg, 64%) as a colourless oil.

$^1$H NMR (300 MHz, $CDCl_3$) δ 7.20 (d, J=8.4 Hz, 2H), 6.87 (d, J=8.4 Hz, 2H), 6.30-6.17 (m, 1H), 5.13 (dd, J=10.2, 2.1 Hz, 1H), 5.09 (dd, J=16.8, 2.1 Hz, 1H), 4.37 (ss, J=15.6, 1.7 Hz, 2H), 4.19 (dd, J=7.2, 2.1 Hz, 1H), 4.10 (dd, J=11.4, 2.7 Hz, 1H), 3.80 (s, 3H), 3.68 (d, J=6.0 Hz, 1H), 3.64-3.57 (m, 2H), 3.49 (dd, J=10.2, 6.0 Hz, 1H), 3.39-3.28 (m, 2H), 2.55 (d, J=9.3 Hz, 1H), 2.27 (d, J=9.6 Hz, 1H), 2.04-1.72 (m, 2H), 1.43 (s, 3H), 1.36 (s, 3H), 1.27 (3, 3H), 1.06 (d, J=6.9 Hz, 3H), 0.92 (s, 9H), 0.86 (s, 9H), 0.12 (s, 3H), 0.07 s, 3H), 0.00 (s, 3H), −0.01 (s, 3H).

$^{13}$C NMR (75 MHz, $CDCl_3$) δ 159.1, 137.2, 130.1, 129.1, 117.1, 113.7, 98.8, 76.5, 72.9, 72.7, 67.8, 66.2, 64.8, 64.5, 58.4, 55.2, 44.9, 44.0, 33.5, 29.8, 26.1, 25.9, 18.8, 18.3, 18.0, 14.9, 13.2, −4.5, −4.6, −5.3, −5.5.

MS (ESI) m/z: 701 $(M+23)^+$.

$R_f$=0.67 (Hex:EtOAc, 4:1).

Example 78

Compound 35a

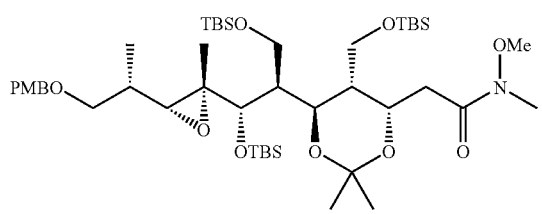

To a solution of 14a (32 mg, 0.037 mmol) in acetone (1.5 mL) was added dimethoxypropane (1.5 mL) and camphorsulfonic acid (0.85 mg, 0.0037 mmol) and the mixture was stirred for 1 h at 23° C. (until TLC revealed total consumption of the starting material). $Et_3N$ (14 μL, 0.01 mmol) was then added and the reaction was stirred for 30 min. Solvents were removed under reduced pressure and the mixture was subjected to flash column chromatography on silica gel (Hex:EtOAc, 4:1) affording acetonide 35a (27 mg, 81%) as a colourless oil.

$^1$H NMR (300 MHz, $CDCl_3$) δ 7.25 (d, J=8.8 Hz, 2H), 6.87 (d, J=8.8 Hz, 2H), 4.49-4.38 (m, 3H), 3.82-3.74 (m, 2H), 3.80 (s, 3H), 3.70-3.30 (m 3H), 3.18 (s, 3H), 2.96 (d, J=9.1 Hz, 1H), 2.74-2.60 (m, 1H), 2.52 (d, J=8.6 Hz, 1H), 2.56-2.46 (m, 1H), 2.42-2.36 (m, 1H), 2.04-1.90 (m, 1H), 1.82-1.58 (m 2H), 1.32 (s, 3H), 1.30 (s, 3H), 1.25 (s, 3H), 1.12 (d, J=6.5 Hz, 3H), 0.92 (s, 9H), 0.89 (s, 9H), 0.87 (s, 9H), 0.17 (s, 3H), 0.10 (s, 3H), 0.08 (s, 3H), 0.05 (s, 3H), 0.03 (s, 3H), 0.02 (s, 3H).

$^{13}$C NMR (75 MHz, $CDCl_3$) δ 173.1, 159.4, 130.7, 129.4, 114.0, 100.9, 78.2, 73.0, 72.2, 67.2, 65.6, 64.0, 63.4, 61.4, 60.8, 59.8, 55.5, 50.5, 46.5, 39.0, 33.4, 30.0, 26.5, 26.3, 25.2, 25.5, 18.7, 18.4, 18.3, 15.4, 12.0, −3.4, −4.8, −5.2, −5.4, −5.7.

MS (ESI) m/z: 921 $(M+23)^+$.

$R_f$=0.24 (Hex:EtOAc, 4:1).

Example 79

Compound 35b

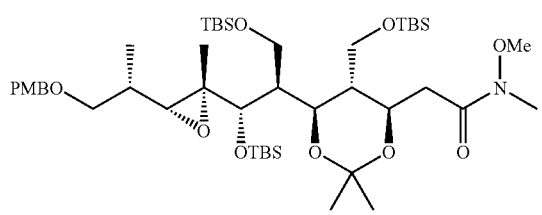

To a solution of 14b (40 mg, 0.047 mmol) in acetone (1.5 mL) was added dimethoxypropane (1.5 mL) and camphorsulfonic acid (1 mg, 0.0047 mmol) and the mixture was stirred for 1 h at 23° C. (until TLC revealed total consumption of the starting material). Et$_3$N (14 µL, 0.01 mmol) was then added and the mixture was stirred for 30 min. Solvents were removed under reduced pressure and the mixture was subjected to flash column chromatography on silica gel (Hex: EtOAc, 4:1) affording acetonide 35b (40 mg, 95%) as a colourless oil.

$^1$H NMR (300 MHz, CDCl$_3$) δ 7.25 (d, J=8.8 Hz, 2H), 6.87 (d, J=8.8 Hz, 2H), 4.42 (dd, J=22.7, 11.3 Hz, 2H), 4.36-4.20 (m, 1H), 4.05 (d, J=11.5 Hz, 1H), 3.80 (s, 3H), 3.82-3.74 (m, 1H), 3.70 (s, 3H), 3.52-3.42 (m, 4H), 3.38-3.33 (m, 1H) 3.19 (s, 3H), 3.07 (d, J=8.0 Hz, 1H) 2.70 (br s, 1H), 2.48 (d, J=8.6 Hz, 1H), 2.04-1.92 (m, 2H), 1.86-1.76 (m, 1H), 1.28 (s, 3H), 1.27 (s, 3H), 1.25 (s, 3H), 1.10 (d, J=6.7 Hz, 3H), 0.91 (s, 9H), 0.90 (s, 9H), 0.87 (s, 9H), 0.15 (s, 3H), 0.09 (s, 3H), 0.07 (s, 3H), 0.03 (s, 3H), 0.02 (s, 3H), 0.01 (s, 3H). $^{13}$CNMR (75 MHz, CDCl$_3$) δ 172.8, 159.4, 130.7, 129.4, 114.0, 97.7, 77.5, 73.1, 72.6, 69.4, 67.7, 64.2, 63.9, 61.7, 61.4, 60.0, 55.5, 47.4, 42.7, 33.3, 30.0, 29.9, 26.4, 26.3, 26.2, 20.2, 18.6, 18.4, 18.3, 15.3, 12.0, −3.4, −3.6, −4.8, −5.2, −5.4, −5.7.

MS (ESI) m/z: 921 (M+23)$^+$.

R$_f$=0.27 (Hex:EtOAc, 4:1).

Example 80

Compound 36a

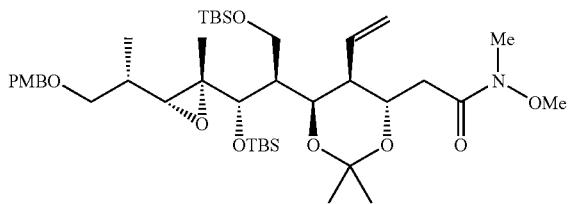

To a solution of 38a (26 mg, 0.035 mmol) in acetone (1 mL) was added dimethoxypropane (1 mL) and camphorsulfonic acid (1 mg, 0.0047 mmol) and the mixture was stirred for 1 h at 23° C. (until TLC revealed total consumption of the starting material). Et$_3$N (14 µL, 0.01 mmol) was then added and the mixture was stirred for 30 min. Solvents were removed under reduced pressure and the mixture was subjected to flash chromatography on silica gel (Hex:EtOAc, 3:1) affording acetonide 36a (18 mg, 70%) as a colourless oil.

$^1$H NMR (300 MHz, CDCl$_3$) δ 7.20 (d, J=8.6 Hz, 2H), 6.87 (d, J=8.6 Hz, 2H), 5.784-5.71 (m, 1H), 5.11-4.97 (m, 2H), 4.41-4.30 (m, 2H), 4.12 (dd, J=7.0, 5.2 Hz, 1H), 3.96-3.90 (m, 1H), 3.81 (s, 3H), 3.68 (s, 3H), 3.70-3.61 (m, 2H), 3.46-3.41 (m, 1H), 3.33 (d, J=6.7 Hz, 2H), 3.17 (s, 3H), 2.82-2.74 (m, 1H), 2.56 (d, J=9.3 Hz, 1H), 2.54-2.49 (m, 1H), 2.41-2.34 (m, 1H), 1.85-1.60 (m, 2H), 1.34 (s, 3H), 1.29 (s, 3H), 1.25 (s, 3H), 1.07 (d, J=6.7 Hz, 3H), 0.94 (s, 9H), 0.86 (s, 9H), 0.12 (s, 3H), 0.10 (s, 3H), 0.01 (s, 3H), 0.00 (s, 3H).

$^{13}$C NMR (75 MHz, CDCl$_3$) δ 172.8, 159.4, 137.1, 130.5, 129.3, 118.7, 114.0, 101.6, 73.1, 72.8, 68.9, 66.2, 65.2, 64.7, 61.4, 59.0, 55.5, 53.5, 43.8, 33.8, 29.9, 26.5, 26.2, 25.0, 24.1, 18.7, 18.3, 15.3, 13.8, −4.1, −4.3, −5.0, −5.1.

MS (ESI) m/z: 802 (M+23)$^+$, 780 (M+1)$^+$.

R$_f$=0.18 (Hex:EtOAc, 4:1).

Example 81

Compound 36b

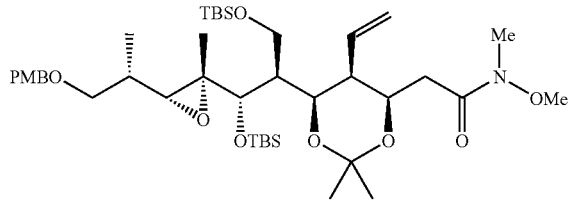

To a solution of 38b (34 mg, 0.046 mmol) in acetone (1 mL) were added dimethoxypropane (1 mL) and camphorsulfonic acid (1 mg, 0.0047 mmol) and the mixture was stirred for 1 h at 23° C. (until TLC revealed total consumption of the starting material). Et$_3$N (14 µL, 0.01 mmol) was then added and the reaction was stirred for 30 min at 23° C. Solvents were removed under reduced pressure and the mixture was subjected to flash column chromatography on silica gel (Hex: EtOAc, 3:1) affording acetonide 36b (33 mg, 92%) as a colourless oil.

$^1$H NMR (300 MHz, CDCl$_3$) δ 7.20 (d, J=8.6 Hz, 2H), 6.86 (d, J=8.6 Hz, 2H), 5.95-6.08 (m, 1H), 5.02-5.25 (m, 2H), 4.42-4.53 (m, 1H), 4.38 (s, 2H), 4.26-4.28 (m, 1H), 3.80 (s, 3H), 3.58-3.69 (m, 2H), 3.65 (s, 3H), 3.41-3.46 (m, 1H), 3.32 (d, J=6.7 Hz, 2H), 3.14 (s, 3H), 2.59-2.67 (m, 1H), 2.55 (d, J=9.1 Hz, 1H), 2.31 (d, J=10.4 Hz, 1H), 2.17-2.29 (m, 1H), 1.64-1.80 (m, 2H), 1.47 (s, 3H), 1.33 (s, 3H), 1.25 (s, 3H), 1.06 (d, J=6.7 Hz, 3H), 0.92 (s, 9H), 0.86 (s, 9H), 0.11 (s, 3H), 0.08 (s, 3H), 0.00 (s, 3H), −0.02 (s, 3H).

$^{13}$C NMR (75 MHz, CDCl$_3$) δ 171.2, 159.4, 134.5, 130.6, 129.3, 113.9, 99.5, 76.5, 73.0, 72.9, 69.2, 64.4, 61.4, 58.7, 55.4, 48.3, 45.5, 36.6, 33.7, 30.1, 29.9, 26.3, 26.1, 19.7, 18.6, 15.2, 13.6, −4.3, −5.1, −5.2.

MS (ESI) m/z: 780.7 (M+1)$^+$, 802.7 (M+23)$^+$.

R$_f$=0.20 (Hex:EtOAc, 4:1).

Example 82

Compound 37

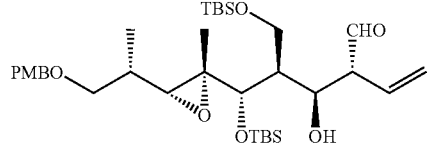

To a solution of diol 11a (300 mg, 0.47 mmol) in CH$_2$Cl$_2$ (10 mL) was added Dess-Martin periodinane (DMP) (0.24 g, 0.56 mmol) and the mixture was stirred at 0° C. for 1 h and for additional 30 min at 23° C. A saturated aqueous solution of NaHCO$_3$ (20 mL) was added and the mixture was extracted with CH$_2$Cl$_2$ (2×20 mL). The combined organic layers were dried over Na$_2$SO$_4$, filtered and evaporated under reduced pressure. The residue 37 was used in the next step without further purification.

$^1$H-NMR (300 MHz, CDCl$_3$): δ 9.45 (d, J=2.6 Hz, 1H), 7.21 (d, J=8.6 Hz, 2H), 6.87 (d, J=8.6 Hz, 2H), 5.75-5.84 (m, 1H), 5.19-5.37 (m, 2H), 4.55-4.58 (m, 1H), 4.40 (s, 2H), 3.81 (s, 3H), 3.45-3.88 (m, 4H), 3.38 (d, J=8.7 Hz, 2H), 3.15-3.20

(m, 1H), 2.55 (d, J=9.1 Hz, 1H), 1.67-1.84 (m, 2H), 1.25 (s, 3H), 1.06 (d, J=6.5 Hz, 3H), 0.91 (s, 9H), 0.87 (s, 9H), 0.16 (s, 3H), 0.10 (s, 3H), 0.05 (s, 3H), 0.04 (s, 3H).

MS (ESI) m/z: 659.7 (M+23). $R_f$=0.56 (Hex:EtOAc, 4:1).

Example 83

Compounds 38a and 38b

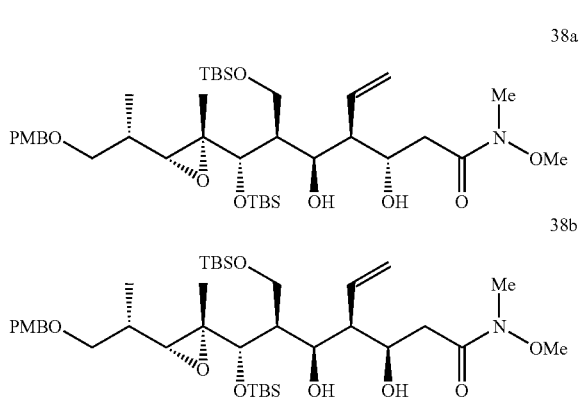

To a solution of N-methoxy-N-methyl acetamide (0.158 mL, 1.41 mmol) in dry THF (5 mL) at −78° C. was added lithium bis(trimethylsilyl)amide (1.41 mL, 1.0 M in THF, 1.41 mmol) and the reaction mixture was stirred for 1 h at this temperature. Then, a solution of crude aldehyde 37 (0.47 mmol) in THF (10 mL) was added over the previous solution and the reaction mixture was stirred for an additional 1 h at −78° C. Then, a saturated aqueous solution on NH$_4$Cl (30 mL) was added and the mixture was extracted with EtOAc (3×50 mL). The combined organic layers were dried over Na$_2$SO$_4$, filtered and concentrated in vacuo. The residue was purified by flash column chromatography on silica gel (Hex:EtOAc from 5:1 to 1:1) to yield 38a and 38b (38:62) as colourless oils (146 mg, 42% overall yield for two steps from 11a).

38a: $^1$H NMR (300 MHz, CDCl$_3$) δ 7.25 (d, J=8.6 Hz, 2H), 6.87 (d, J=8.6 Hz, 2H), 5.81-5.86 (m, 1H), 5.07-5.22 (m, 2H), 4.46-4.50 (m, 1H), 4.44 (dd, J=24.4 and 11.5 Hz, 2H), 4.05-4.16 (m, 1H), 3.65-3.94 (m, 3H), 3.79 (s, 3H), 3.53 (d, J=4.7 Hz, 1H), 3.32-3.44 (m, 2H), 3.15-3.23 (m, 1H), 3.17 (s, 3H), 2.68-2.75 (m, 1H), 2.62 (d, J=9.3 Hz, 1H), 2.18-2.24 (m, 1H), 2.09-2.15 (m, 1H), 1.82-1.93 (m, 2H), 1.24 (s, 3H), 1.04 (d, J=6.7 Hz, 3H), 0.91 (s, 9H), 0.86 (s, 9H), 0.14 (s, 3H), 0.08 (s, 3H), 0.04 (s, 3H), 0.02 (s, 3H).

$^{13}$C NMR (75 MHz, CDCl$_3$) δ 174.5, 159.3, 139.5, 136.4, 130.7, 129.3, 118.9, 114.0, 77.0, 73.0, 72.7, 69.9, 68.4, 64.9, 64.2, 61.4, 61.3, 55.4, 55.0, 48.7, 36.5, 33.8, 32.1, 29.9, 26.3, 26.0, 18.4, 18.1, 15.1, 14.1, −4.2, −5.0, −5.1, −5.2.

MS (ESI) m/z: 740.5 (M+1)$^+$, 762.6 (M+23)$^+$.

$R_f$=0.08 (Hex:EtOAc, 4:1).

38b: $^1$H NMR (300 MHz, CDCl$_3$): δ 7.23 (d, J=8.6 Hz, 2H), 6.85 (d, J=8.6 Hz, 2H), 5.95-6.08 (m, 1H), 5.04-5.30 (m, 2H), 4.43 (dd, J=11.8, 11.8 Hz, 2H), 4.29-4.33 (m, 1H), 4.12 (br s, 1H), 3.78-3.89 (m, 2H), 3.79 (s, 3H), 3.57-3.72 (m, 1H), 3.65 (s, 3H), 3.33-3.44 (m, 2H), 3.15 (s, 31), 2.59 (d, J=9.1 Hz, 1H), 2.46-2.62 (m, 1H), 1.73-1.89 (m, 2H), 1.24 (s, 3H), 1.06 (d, J=6.7 Hz, 3H), 0.91 (s, 9H), 0.86 (s, 9H), 0.15 (s, 3H), 0.08 (s, 3H), 0.04 (s, 3H), 0.03 (s, 3H).

$^{13}$C NMR (75 MHz, CDCl$_3$) δ 171.4, 159.3, 135.4, 130.6, 129.4, 119.2, 113.9, 77.6, 73.0, 72.8, 72.7, 70.3, 64.8, 64.3, 61.4, 60.8, 55.4, 52.8, 47.4, 36.7, 33.6, 29.9, 26.3, 18.4, 18.2, 15.0, 14.0, −4.2, −5.0, −5.1, −5.2.

MS (ESI) m/z: 740.6 (M+1)$^+$, 762.6 (M+23)$^+$. $R_f$=0.10 (Hex:EtOAc, 4:1).

Example 84

Compound 39a

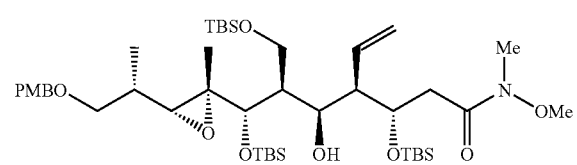

To a solution of 38a (106 mg, 0.143 mmol) in CH$_2$Cl$_2$ (8 mL) at 0° C. was added 2,6-lutidine (0.051 mL, 0.44 mmol) and TBSOTf (0.05 mL, 0.22 mmol) successively. The reaction mixture was stirred at this temperature for 1 h. Aqueous solution of NaHCO$_3$ (20 mL) was then added and extracted with CH$_2$Cl$_2$ (2×20 mL). The combined organic layers were dried over Na$_2$SO$_4$, filtered and concentrated in vacuo. The residue was purified by flash column chromatography on silica gel (Hex:EtOAc, 10:1) to obtain compound 39a (79 mg, 65%) as a colourless oil.

$^1$H NMR (300 MHz, CDCl$_3$) δ 7.23 (d, J=8.6 Hz, 2H), 6.88 (d, J=8.6 Hz, 2H), 5.82-5.94 (m, 1H), 5.07-5.20 (m, 2H), 4.44 (dd, J=18.8, 11.9 Hz, 1H), 4.37-4.41 (m, 2H), 3.91-3.95 (m, 1H), 3.80 (s, 3H), 3.67-3.79 (m, 2H), 3.64 (s, 3H), 3.30-3.40 (m, 2H), 3.13 (s, 3H), 3.07 (d, J=4.4 Hz, 1H), 2.66-2.76 (m, 1H), 2.59 (d, J=9.1 Hz, 1H), 2.47 (dd, J=15.6, 3.4 Hz, 1H), 2.27-2.34 (m, 1H), 1.68-1.82 (m, 2H), 1.25 (s, 3H), 1.05 (d, J=6.7 Hz, 3H), 0.91 (s, 9H), 0.86 (s, 9H), 0.85 (s, 9H), 0.14 (s, 3H), 0.05 (s, 3H), 0.03 (s, 3H), 0.02 (s, 3H).

$^{13}$C NMR (75 MHz, CDCl$_3$) δ 172.5, 159.1, 135.8, 130.4, 129.0, 118.4, 113.8, 76.7, 72.9, 72.6, 70.3, 69.0, 64.6, 61.4, 60.4, 56.0, 55.4, 47.3, 33.8, 29.9, 26.4, 26.1, 26.0, 18.5, 18.3, 18.1, 15.2, 14.0, −4.1, −4.2, −4.5, −5.0, −5.1.

MS (ESI) m/z: 854.4 (M+1)$^+$, 876.2 (M+23)$^+$.

$R_f$=0.53 (Hex:EtOAc, 4:1).

Example 85

Compound 39b

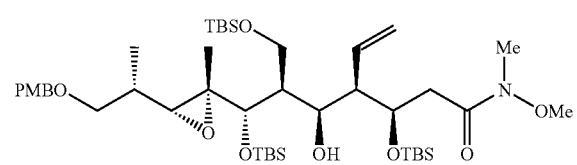

To a solution of 38b (89 mg, 0.12 mmol) in CH$_2$Cl$_2$ (8 mL) at 0° C. was added 2,6-lutidine (0.042 mL, 0.36 mmol) and TBSOTf (0.041 mL, 0.18 mmol) successively. The reaction mixture was stirred at this temperature for 1 h. A saturated aqueous solution of NaHCO$_3$ (20 mL) was then added and the mixture was extracted with CH$_2$Cl$_2$ (2×20 mL). The combined organic layers were dried over Na$_2$SO$_4$, filtered and concentrated in vacuo. The residue was purified by flash column chromatography on silica gel (Hex:EtOAc, 10:1) to obtain compound 39b (86 mg, 84%) as a colourless oil.

$^1$H NMR (300 MHz, CDCl$_3$) δ 7.24 (d, J=8.6 Hz, 2H), 6.87 (d, J=8.6 Hz, 2H), 5.89-6.01 (m, 1H), 5.03-5.25 (m, 2H), 4.40

(dd, J=18.4, 11.4 Hz, 2H), 4.16-4.22 (m, 3H), 3.79-3.86 (m, 1H), 3.79 (s, 3H), 3.63-3.70 (m, 1H), 3.67 (s, 3H), 3.27-3.44 (m, 3H), 3.16 (s, 3H), 2.70-2.80 (m, 1H), 2.6 (d, J=9.1 Hz, 1H), 2.51-2.58 (m, 1H), 2.27-2.32 (m 1H), 1.65-1.89 (m, 2H), 1.26 (s, 3H), 1.09 (d, J=6.7 Hz, 3H), 0.92 (s, 9H), 0.87 (s, 9H), 0.86 (s, 9H), 0.13 (s, 3H), 0.10 (s, 3H), 0.09 (s, 3H), 0.06 (s, 3H), 0.04 (s, 3H), 0.03 (s, 3H).
$^{13}$C NMR (75 MHz, CDCl$_3$) δ 172.7, 159.4, 137.5, 130.5, 129.5, 118.5, 114.0, 76.4, 73.1, 72.7, 69.1, 64.8, 64.1, 61.5, 61.0, 55.4, 54.4, 44.4, 37.3, 34.4, 32.1, 29.9, 26.6, 26.2, 26.0, 18.9, 18.2, 17.9, 15.4, 12.7, −4.0, −4.2, −4.7, −5.0, −5.1.
MS (ESI) m/z: 854.4 (M+1)$^+$, 876.3 (M+23)$^+$.
R$_f$=0.43 (Hex:EtOAc, 4:1).

Example 86

Compound 40a

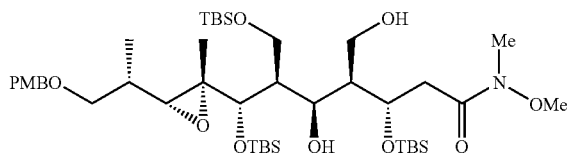

Over a solution of 39a (79 mg, 0.09 mmol) in CH$_2$Cl$_2$ (15 mL) at −78° C. was bubbled ozone until the clear solution turned to light blue (2 min). Then MeOH (15 mL) and NaBH$_4$ (15 mg, 0.4 mmol) were added and the solution was allowed to reach 23° C. during 2h. After this time, solvents were removed under reduced pressure, an the residue was dissolved in CH$_2$Cl$_2$, hydrolysed with aqueous NH$_4$Cl and extracted with CH$_2$Cl$_2$ (2×20 mL). The combined organic layers were dried over Na$_2$SO$_4$, filtered and concentrated in vacuo. The residue was purified by flash column chromatography on silica gel (Hex:EtOAc, from 4:1 to 2:1) to obtain compound 40a (10 mg, 13%) as a colorless oil.
$^1$H NMR (300 MHz, CDCl$_3$) δ 7.23 (d, J=8.6 Hz, 2H), 6.89 (d, J=8.6 Hz, 2H), 4.43 (dd, J=19.6, 11.7 Hz, 2H), 4.20-4.33 (m, 2H), 3.61-4-07 (m, 5H), 3.81 (s, 3H), 3.68 (s, 3H), 3.31-3.45 (m, 2H), 3.16 (s, 3H), 2.77-2.89 (m, 1H), 2.65 (d, J=9.3 Hz, 1H), 2.03-2.16 (m, 2H), 1-76-1.81 (m, 2H), 1.62-1.68 (m, 2H), 1.25 (s, 3H), 1.07 (d, J=6.5 Hz, 3H), 0.90 (s, 9H), 0.88 (s, 9H), 0.86 (s, 9H), 0.15 (s, 3H), 0.12 (s, 3H), 0.11 (s, 3H), 0.10 (s, 3H), 0.08 (s, 3H), 0.00 (s, 3H).
MS (ESI) m/z: 880 (M+23)$^+$.
R$_f$=0.15 (Hex:EtOAc, 4:1).

Example 87

Compound 40b

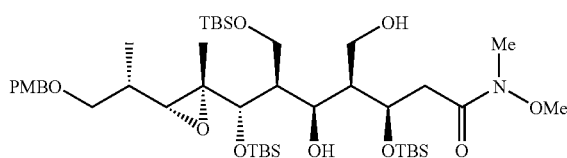

Over a solution of 39b (86 mg, 0.1 mmol) in CH$_2$Cl$_2$ (15 mL) at −78° C. was bubbled ozone until the clear solution turned to light blue (2 min). Then MeOH (15 mL) and NaBH$_4$ (15 mg, 0.4 mmol) were added and the solution was allowed to reach room temperature during 2h. After this time, solvents were removed under reduced pressure, and the residue was dissolved in CH$_2$Cl$_2$, hydrolyzed with aqueous NH$_4$Cl and extracted with CH$_2$Cl$_2$ (2×20 mL). The combined organic layers were dried over Na$_2$SO$_4$, filtered and concentrated in vacuo. The residue was purified by flash column chromatography on silica gel (Hex:EtOAc, from 4:1 to 2:1) to obtain compound 40b (50 mg, 58%) as a colorless oil.
$^1$H NMR (300 MHz, CDCl$_3$): δ 7.25 (d, J=8.6 Hz, 2H), 6.87 (d, J=8.6 Hz, 2H), 4.41 (dd, J=19.3, 11.4 Hz, 2H), 4.18-4.40 (m, 3H), 3.64-3.95 (m, 6H), 3.79 (s, 3H), 3.71 (s, 3H), 3.30-3.42 (m, 2H), 3.16 (s, 3H), 2.90-2.98 (m, 1H), 2.60 (d, J=9.1 Hz, 1H), 2.55-2.62 (m, 1H), 1.78-1.87 (m, 3H), 1.27 (s, 3H), 1.08 (d, J=6.7 Hz, 3H), 0.92 (s, 9H), 0.86 (s, 9H), 0.85 (s, 9H), 0.14 (s, 3H), 0.12 (s, 3H), 0.09 (s, 3H), 0.05 (s, 3H), 0.05 (s, 3H), 0.03 (s, 3H). $^{13}$C NMR (75 MHz, CDCl$_3$) δ 171.8, 159.2, 130.2, 129.4, 113.8, 75.8, 72.8, 72.5, 72.2, 68.7, 64.5, 63.6, 63.2, 61.4, 60.7, 55.2, 48.5, 43.0, 37.4, 34.2, 31.9, 29.7, 26.3, 25.9, 25.7, 18.6, 17.9, 17.6, 15.2, 12.5, −4.4, −4.5, −5.1, 5.2, −5.4, −5.5.
MS (ESI) m/z: 880 (M+23)$^+$.
R$_f$=0.13 (Hex:EtOAc, 4:1).

Example 88

Compound 41b

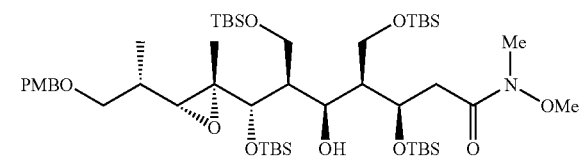

To a solution of 40b (50 mg, 0.06 mmol) in CH$_2$Cl$_2$ (8 mL) at 0° C. was added 2,6-lutidine (0.021 mL, 0.18 mmol) and TBSOTf (0.021 mL, 0.09 mmol) successively. The reaction mixture was stirred at this temperature for 1 h. A saturated aqueous solution of NaHCO$_3$ (20 mL) was then added and the mixture was extracted with CH$_2$Cl$_2$ (2×20 mL). The combined organic layers were dried over Na$_2$SO$_4$, filtered and concentrated in vacuo. The residue was purified by flash column chromatography on silica gel (Hex:EtOAc, 10:1) to obtain compound 41b (57 mg, 98%) as a colorless oil.
$^1$H NMR (300 MHz, CDCl$_3$) δ 7.23 (d, J=8.6 Hz, 2H), 6.87 (d, J=8.6 Hz, 2H), 4.65 (m, 1H), 4.41 (dd, J=15.9, 11.7 Hz, 2H), 4.17-4.21 (m, 1H), 4.04-4.11 (m, 2H), 3.79-3.86 (m, 1H), 3.80 (s, 3H), 3.66 (s, 3H), 3.25-3.31 (m, 1H), 3.16 (s, 3H), 2.72-2.84 (m, 1H), 2.62 (d, J=9.3 Hz, 1H), 2.46-2.54 (m, 1H), 1.82-2.05 (m, 1H), 1.62-1.82 (m, 2H), 1.25 (s, 3H), 1.10 (d, J=6.7 Hz, 3H), 0.92 (s, 9H), 0.91 (s, 9H), 0.87 (s, 9H), 0.83 (s, 9H), 0.16 (s, 3H), 0.11 (s, 3H), 0.10 (s, 3H), 0.08 (s, 3H), 0.07 (s, 3H), 0.05 (s, 3H), 0.03 (s, 3H). $^{13}$C NMR (75 MHz, CDCl$_3$) δ 173.1, 159.4, 130.0, 129.4, 114.0, 76.2, 72.8, 72.0, 69.2, 68.7, 64.5, 63.7, 61.9, 61.5, 55.4, 51.2, 44.5, 34.4, 29.9, 26.5, 26.2, 26.1, 18.8, 18.4, 18.1, 17.9, 15.6, 12.3, −3.8, −4.6, −4.7, −5.0, −5.1, −5.2.
MS (ESI) m/z: 972.6 (M+1)$^+$, 994.6 (M+23)$^+$.
R$_f$=0.56 (Hex:EtOAc, 4:1).

Example 89

Compounds 43 and 44

To a solution of 20b (14 mg, 0.024 mmol) in CHCl$_3$ (3 mL) was added Et$_3$N (28 μL, 0.2 mmol) and Ac$_2$O (10 μL, 0.1 mmol) at 23° C. The reaction mixture was stirred at 23° C. for 16 h. Then, the solvent was eliminated under reduced pressure and the residue was purified by flash column chromatography on silica gel (Hex:EtOAc, from 2:1 to 1:1) to obtain pure compounds 43 (6 mg, 47%) as a yellow oil and 44 (6 mg, 44%) as a white solid.

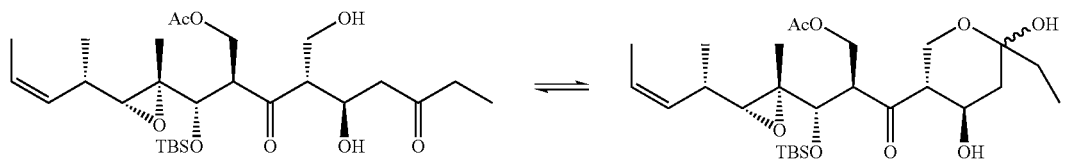

43: ¹H NMR (300 MHz, CDCl₃) (data of the mayor product) δ 5.53-5.45 (m, 1H), 5.31-5.19 (m, 1H), 4.45-4.40 (m, 2H), 3.92-3.80 (m, 3H), 3.53 (d, J=9.9 Hz, 1H), 3.27-3.21 (m, 1H), 2.76-2.66 (m, 1H), 2.56 (d, J=9.3 Hz, 1H), 2.49-2.41 (m, 1H), 2.06-2.00 (m, 1H), 2.03 (s, 3H), 1.68-1.66 (m, 3H), 1.62 (dd, J=12.0, 6.6 Hz, 3H), 1.32 (s, 3H), 1.13 (d, J=6.6 Hz, 3H), 0.97 (t, J=7.5 Hz, 3H), 0.86 (s, 9H), 0.13 (s, 3H), −0.01 (s, 3H).

MS (ESI) m/z: 551 (M+23)⁺.

R$_f$=0.39 (Hex:EtOAc, 50:50).

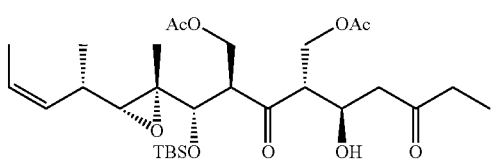

44: ¹H NMR (300 MHz, CDCl₃) δ 5.52-5.46 (m, 1H), 5.22-5.15 (m, 1H), 4.50 (dd, J=11.0, 4.5 Hz, 1H), 4.47-4.43 (m, 1H), 4.34-4.33 (m, 1H) 4.13-4.07 (m, 1H), 3.90-3.81 (m, 1H), 3.70-3.65 (m, 1H), 3.56 (d, J=9.3 Hz, 1H), 3.33-3.26 (m, 1H), 3.13-3.11 (m, 1H), 2.69-2.64 (m, 2H), 2.55 (d, J=9.0 Hz, 1H), 2.48-2.39 (m, 2H), 2.09 (s, 3H), 2.00 (s, 3H), 1.67-1.61 (m, 3H), 1.32 (s, 3H), 1.13 (d, J=6.3 Hz, 3H), 1.05 (t, J=7.2 Hz, 3H), 0.85 (s, 9H), 0.15 (s, 3H), −0.01 (s, 3H).

MS (ESI) m/z: 593 (M+23)⁺.

R$_f$=0.53 (Hex:EtOAc, 50:50).

Example 90

Compound 45

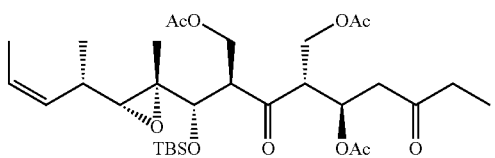

To a solution of 20b (34 mg, 0.07 mmol) in CH₂Cl₂ (0.7 mL) was added Et₃N (11.5 μL, 0.82 mmol), DMAP (5 mg, 0.041 mmol) and Ac₂O (39 μL, 0.41 mmol) at 0° C. The reaction mixture was stirred at 23° C. for 3 h. Then, 0.1N HCl was added until pH=4-5, and the reaction was extracted with CH₂Cl₂ (2×5 mL). The combined organic layers were dried over Na₂SO₄, filtered, and concentrated under reduced pressure. The residue was purified by flash column chromatography on silica gel (Hex:EtOAc, 3:1) to obtain compound 45 (17 mg, 40%) as a yellow oil.

¹H NMR (300 MHz, CDCl₃) δ 5.60-5.56 (m, 1H), 5.54-5.44 (m, 1H), 5.26-5.19 (m, 1H), 4.46 (dd, J=11.1, 5.7 Hz, 1H), 4.35 (dd, J=11.4, 3.3 Hz, 1H), 4.14 (dd, J=12.0, 6.9 Hz, 1H), 3.87 (dd, J=11.4, 8.1 Hz, 1H), 3.55-3.49 (m, 2H), 3.46-3.38 (m, 2H), 2.79-2.76 (m, 2H), 2.52 (d, J=9.3 Hz, 1H), 2.45-2.38 (m, 3H), 2.06 (s, 3H), 1.99 (s, 6H), 1.62 (dd, J=6.9, 1.8 Hz, 1H), 1.33 (s, 3H), 1.11 (d, J=6.3 Hz, 3H), 1.03 (t, J=7.2 Hz, 3H), 0.85 (s, 9H), 0.13 (s, 3H), 0.00 (s, 3H).

MS,(ESI) m/z: 635 (M+23)⁺.
Rf=0.54 (Hex:EtOAc, 50:50).

Example 91

Compound 46

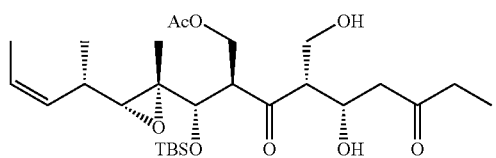 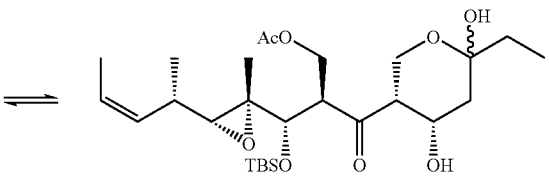

To a solution of 20a (18 mg, 0.037 mmol) in CH₂Cl₂ (3 mL) was added Et₃N (21 μL, 0.15 mmol) and Ac₂O (7 μL, 0.074 mmol) at 23° C. The reaction mixture was stirred at 23° C. for 16 h. Then, NaHCO₃ (5 mL) was added and the reaction was extracted with CH₂Cl₂ (2×5 mL). The combined organic layers were dried over Na₂SO₄, filtered, and concentrated under reduced pressure. The residue was purified by flash column chromatography on silica gel (Hex:EtOAc, from 3:1 to 2:1). to obtain compound 46 (16 mg, 82%) as a white solid.

¹H NMR (300 MHz, CDCl₃) (data of the mayor product) δ 5.55-5.45 (m, 1H), 5.26-5.19 (m, 1H), 5.06 (s, 1H), 4.56 (bs, 1H), 4.45 (dd, J=11.4, 3.6 Hz, 1H), 4.22 (t, J=11.7 Hz, 1H), 4.06 (bs, 1H), 3.97-3.82 (m, 2H), 3.47 (d, J=9.6 Hz, 1H), 3.21-3.14 (m, 1H), 2.94-2.89 (m, 1H), 2.56 (d, J=9.0 Hz, 1H), 2.06-2.98 (m, 1H), 2.02 (s, 3H), 1.63-1.58 (m, 6H), 1.30 (s, 3H), 1.13 (d, J=6.6 Hz, 3H), 0.94 (t, J=7.5 Hz, 3H), 0.85 (s, 9H), 0.13 (s, 3H), −0.01 (s, 3H). ¹³C NMR (75 MHz, CDCl₃) (data of the mayor product) δ 212.2, 170.4, 130.5, 125.3, 97.5, 77.5, 66.0, 65.6, 62.2, 62.1, 55.9, 54.2, 54.1, 37.4, 34.6, 31.6, 29.9, 26.2, 20.9, 18.9, 13.5, 11.8, 7.7, −4.2, −4.6.

MS (ESI) m/z: 551 (M+23)⁺.

Rf=0.38 (Hex:EtOAc, 2:1).

Example 92

Compounds 47 and 1

To a solution of crude 4a (20 mg, 0.054 mmol) in CHCl₃ (3 mL) was added Et₃N (22 μL, 0.16 mmol) and Ac₂O (8 μL, 0.081 mmol) at 23° C. The reaction mixture was stirred at 23° C. for 16 h. Then, the solvent was eliminated under reduced pressure and the residue was purified by flash column chromatography on silica gel (Hex:EtOAc, from 2:1 to 1:1) to obtain pure compounds 47 (10 mg, 48%) and 1 (4 mg, 44%) as yellow oils.

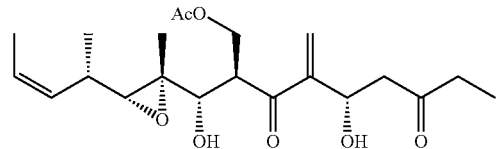

1: $^1$H NMR (500 MHz MeOD) δ 6.27 (s, 1H), 6.22 (d, J=1.2 Hz, 1H), 5.55-5.46 (m, 1H), 5.30-5.23 (m, 1H), 5.04-

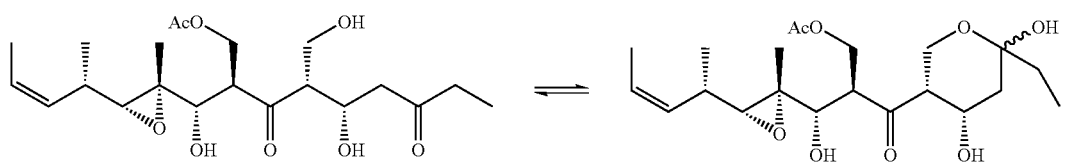

47: $^1$H NMR (500 MHz CD₃OD) (data of the hemiketal product) δ 5.50 (m, 1H), 5.26 (m, 1H), 4.57 (m, 1H), 4.28 (dd, J=12.5, 12.0 Hz, 1H), 4.15 (dd, J=11.0, 4.0 Hz, 1H), 4.00 (dd, J=11.0, 9.5 Hz, 1H), 3.69 (dd, J=12.5, 5.0 Hz, 1H), 3.40 (m, 1H), 3.13 (d, J=10.5 Hz, 1H), 2.97 (ddd, J=12.0, 5.0, 2.5 Hz, 1H), 2.62 (d, J=9.5 Hz, 1H), 2.47 (m, 1H), 1.97 (s, 3H), 1.93 (dd, J=14.0, 3.0 Hz, 1H), 1.72 (dd, J=14.0, 3.0 Hz, 1H), 1.64 (brd, J=7.0 Hz, 3H), 1.57 (d, J=7.5 Hz, 2H), 1.37 (s, 3H), 1.09 (d, J=7.0 Hz, 3H), 0.92 (t, J=7.5 Hz, 3H). $^{13}$C NMR (125 MHz CD₃OD) (data of the hemiketal product) δ 212.6, 172.6, 131.5, 126.1, 98.8, 78.6, 67.6, 66.1, 64.3, 62.9, 56.8, 56.0, 52.2, 38.6, 35.6, 32.3, 20.8, 18.8, 13.6, 11.6, 7.9.

MS (ESI) m/z: 437 (M+23)⁺.

5.01 (m, 1H), 4.32 (dd, J=10.5, 3.9 Hz, 1H), 3.88 (dd, J=9.9, 9.9 Hz, 1H), 3.76 (ddd, J=19.8, 9.9, 3.6 Hz 1H), 3.34 (d, J=9.9 Hz), 1.94 (s, 3H), 1.65 (dd, J=6.9, 1.8 Hz, 1H), 1.38 (d, J=6.6 Hz, 3H), 1.01 (t, J=7.5 Hz, 3H).

MS (ESI) m/z: 419 (M+23)⁺.

R$_f$=0.37 (Hex:EtOAc, 1:2).

Example 93

Bioassays for Antitumor Screening

The finality of these assays is to interrupt the growth of a "in vitro" tumor cell culture by means a continued exhibition of the cells to the sample to be testing.

Cell Lines

| NAME | N° ATCC | SPECIES | TISSUE | CHARACTERISTICS |
|---|---|---|---|---|
| K-562 | CCL-243 | human | leukemia | erythroleukemia (pleural effusion) |
| A-549 | CCL-185 | human | lung | lung carcinoma "NSCL" |
| SK-MEL-28 | HTB-72 | human | melanoma | malignant melanoma |
| HT-29 | HTB-38 | human | colon | colon adenocarcinoma |
| LoVo | CCL-229 | human | colon | colon adenocarcinoma |
| LoVo-Dox | | human | colon | colon adenocarcinoma (MDR) |
| DU-145 | HTB-81 | human | prostate | prostate carcinoma, not androgen receptors |
| LNCaP | CRL-1740 | human | prostate | prostate adenocarcinoma, with androgen receptors |
| SK-BR-3 | HTB-30 | human | breast | breast adenocarcinoma, Her2/neu+, (pleural effusion) |
| IGROV | | human | ovary | ovary adenocarcinoma |
| IGROV-ET | | human | ovary | ovary adenocarcinoma, characterized as ET-743 resistant cells |
| HeLa | CCL-2 | human | cervix | cervix epitheloid carcinoma |
| HeLa-APL | CCL-3 | human | cervix | cervix epitheloid carcinoma, characterized as aplidine resistant cells |
| PANC-1 | CRL-1469 | human | pancreas | pancreatic epitheloid carcinoma |

Inhibition of Cell Growth by Colorimetric Assay.

A colorimetric type of assay, using sulforhodamine B (SRB) reaction has been adapted for a quantitative measurement of cell growth and viability (following the technique described by P. A. Skehan, et al., *J. Natl. CancerInst.* 1990, 82, 1107-1112).

This form of assay employs 96 well cell culture microplates of 9 mm diameter (T. Mosmann et al., *J. of Immuological Methods* 1983, 65, 55-63; G. T. Faircloth et al., *J. of Tissue and Culture Methods* 1988, 11, 201-205). Most of the cell lines are obtained from American Type Culture Collection (ATCC) derived from different human cancer types.

Cells are maintained in RPMI 1640 10% FBS, supplemented with 0.1 g/L penicillin and 0.1 g/L streptomycin sulfate and then incubated at 37° C., 5% $CO_2$ and 98% humidity. For the experiments, cells were harvested from subconfluent cultures using trypsin and resuspended in fresh medium before plating.

Cells are seeded in 96 well microtiter plates, at $5 \times 10^3$ cells per well in aliquots of 195 μL medium, and they are allowed to attach to the plate surface by growing in drug free medium for 18 hours. Afterward, samples are added in aliquots of 5 μL in a ranging from 10 to $10^{-8}$ μg/mL, dissolved in DMSO/EtOH/PBS (0.5:0.5:99). After 48 hours exposure, the antitumor effect are measured by the SRB methodology: cells are fixed by adding 50 μL of cold 50% (wt/vol) trichloroacetic acid (TCA) and incubated for 60 minutes at 4° C. Plates are washed with deionizer water and dried. One hundred μl of SRB solution (0.4% wt/vol in 1% acetic acid) is added to each microliter well and incubated for 10 minutes at room temperature. Unbound SRB is removed by washing with 1% acetic acid. Plates are air dried and bound stain is solubilized with Tris buffer. Optical densities are read on a automated spectrophotometric plate reader at a single wavelength of 490 nm.

The values for mean +/−SD of data from triplicate wells are calculated. Some parameters for cellular responses can be calculated: GI=growth inhibition, TGI=total growth inhibition (cytostatic effect) and LC=cell killing (cytotoxic effect).

Tables 1 illustrates data on the biological activity of the compounds of the present invention.

TABLE 1

| | | Activity data (Molar) | | | | |
|---|---|---|---|---|---|---|
| | | 19a | 19b | 20a + 20c | 20b + 20d | 31b + 31d |
| DU-145 | GI50 | 1.21E−05 | 1.20E−05 | 1.07E−05 | 2.05E−05 | 2.05E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| LN-caP | GI50 | 1.21E−05 | 1.20E−05 | 8.42E−06 | 1.24E−05 | — |
| | TGI | 1.21E−05 | 1.20E−05 | 2.05E−05 | 2.05E−05 | — |
| | LC50 | 1.21E−05 | 1.20E−05 | 2.05E−05 | 2.05E−05 | — |
| IGROV | GI50 | 1.21E−05 | 1.20E−05 | 1.41E−05 | 2.05E−05 | 1.65E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| IGROV-ET | GI50 | 1.21E−05 | 1.20E−05 | 1.38E−05 | 2.05E−05 | 2.05E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| SK-BR-3 | GI50 | 1.21E−05 | 6.15E−06 | 1.11E−05 | 1.49E−05 | 2.02E−05 |
| | TGI | 1.21E−05 | 1.17E−05 | 2.05E−05 | 2.05E−05 | 2.05E−05 |
| | LC50 | 1.21E−05 | 1.20E−05 | 2.05E−05 | 2.05E−05 | 2.05E−05 |
| MEL-28 | GI50 | 1.21E−05 | 1.20E−05 | 1.63E−05 | 2.05E−05 | 2.05E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| A-549 | GI50 | 1.21E−05 | 1.20E−05 | 2.05E−05 | 2.05E−05 | 2.05E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| K-562 | GI50 | 1.21E−05 | 1.20E−05 | 7.75E−06 | 1.03E−05 | — |
| | TGI | 1.21E−05 | 1.20E−05 | 2.05E−05 | 2.05E−05 | — |
| | LC50 | 1.21E−05 | 1.20E−05 | 2.05E−05 | 2.05E−05 | — |
| PANC-1 | GI50 | 1.21E−05 | 1.20E−05 | 1.40E−05 | 9.37E−06 | 1.26E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| HT-29 | GI50 | 1.21E−05 | 1.20E−05 | 1.71E−05 | 2.05E−05 | 2.05E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| LOVO | GI50 | 1.21E−05 | 1.20E−05 | 1.04E−05 | 2.05E−05 | 2.05E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| LOVO-DOX | GI50 | 1.21E−05 | 1.20E−05 | 8.51E−05 | 2.05E−05 | 2.05E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| HELA | GI50 | 1.21E−05 | 1.20E−05 | 1.33E−05 | 2.05E−05 | 2.05E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |
| HELA-APL | GI50 | 1.21E−05 | 1.20E−05 | 1.29E−05 | 2.05E−05 | 2.05E−05 |
| | TGI | 1.21E−05 | 1.20E−05 | 2.05E−05 | 2.05E−05 | 2.05E−05 |
| | LC50 | 1.21E−05 | 1.20E−05 | 2.05E−05 | 2.05E−05 | 2.05E−05 |

| | | 30a | 30b | 3a + 4a | 3b + 4b | 3c + 4c | 3d + 4d |
|---|---|---|---|---|---|---|---|
| DU-145 | GI50 | 1.21E−05 | 1.21E−05 | 6.31E−08 | 6.52E−06 | 5.50E−07 | 2.68E−05 |
| | TGI | 1.21E−05 | 1.21E−05 | 4.03E−07 | 2.68E−05 | 4.16E−06 | 2.68E−05 |
| | LC50 | 1.21E−05 | 1.21E−05 | 2.03E−06 | 2.68E−05 | 2.68E−05 | 2.68E−05 |

TABLE 1-continued

Activity data (Molar)

| | | | | | | | |
|---|---|---|---|---|---|---|---|
| LN-caP | GI50 | — | — | 8.19E−08 | 9.29E−06 | 7.03E−07 | — |
| | TGI | — | — | 5.53E−07 | 2.68E−05 | 4.56E−06 | — |
| | LC50 | — | — | 5.32E−06 | 2.68E−05 | 2.68E−05 | — |
| IGROV | GI50 | — | — | 7.30E−08 | 5.96E−06 | 5.53E−07 | 2.05E−05 |
| | TGI | — | — | 3.76E−07 | 2.68E−05 | 3.57E−06 | 2.68E−05 |
| | LC50 | — | — | 3.92E−06 | 2.68E−05 | 2.09E−05 | 2.68E−05 |
| IGROV-ET | GI50 | 8.27E−06 | 8.27E−06 | 1.00E−07 | 6.55E−06 | 7.03E−07 | 1.71E−05 |
| | TGI | 1.21E−05 | 1.21E−05 | 1.07E−06 | 2.68E−05 | 6.95E−06 | 2.68E−05 |
| | LC50 | 1.21E−05 | 1.21E−05 | 2.68E−05 | 2.68E−05 | 2.68E−05 | 2.68E−05 |
| SK-BR-3 | GI50 | 8.56E−06 | 1.21E−05 | 3.03E−08 | 5.07E−06 | 1.16E−06 | 2.05E−05 |
| | TGI | 1.21E−05 | 1.21E−05 | 4.75E−07 | 1.09E−05 | 6.07E−06 | 2.68E−05 |
| | LC50 | 1.21E−05 | 1.21E−05 | 5.34E−06 | 2.33E−05 | 2.68E−05 | 2.68E−05 |
| MEL-28 | GI50 | 1.21E−05 | 1.21E−05 | 7.54E−08 | 5.53E−06 | 6.34E−07 | 2.68E−05 |
| | TGI | 1.21E−05 | 1.21E−05 | 8.32E−07 | 2.68E−05 | 7.25E−06 | 2.68E−05 |
| | LC50 | 1.21E−05 | 1.21E−05 | 1.20E−05 | 2.68E−05 | 2.68E−05 | 2.68E−05 |
| A-549 | GI50 | 1.21E−05 | 1.21E−05 | 1.44E−07 | 2.68E−05 | 9.13E−07 | 2.68E−05 |
| | TGI | 1.21E−05 | 1.21E−05 | 2.59E−06 | 2.68E−05 | 1.34E−05 | 2.68E−05 |
| | LC50 | 1.21E−05 | 1.21E−05 | 1.56E−05 | 2.68E−05 | 2.68E−05 | 2.68E−05 |
| K-562 | GI50 | — | — | 5.21E−07 | 1.42E−05 | 4.59E−06 | — |
| | TGI | — | — | 1.46E−06 | 1.82E−05 | 1.19E−05 | — |
| | LC50 | — | — | 8.40E−06 | 2.33E−05 | 2.68E−05 | — |
| PANC-1 | GI50 | 1.21E−05 | 1.21E−05 | 8.97E−08 | 2.68E−05 | 1.03E−06 | 1.35E−05 |
| | TGI | 1.21E−05 | 1.21E−05 | 2.95E−06 | 2.68E−05 | 1.33E−05 | 2.68E−05 |
| | LC50 | 1.21E−05 | 1.21E−05 | 2.68E−05 | 2.68E−05 | 2.68E−05 | 2.68E−05 |
| HT-29 | GI50 | — | — | 6.01E−08 | 2.21E−05 | 5.64E−07 | 2.68E−05 |
| | TGI | — | — | 1.18E−06 | 2.68E−05 | 6.69E−06 | 2.68E−05 |
| | LC50 | — | — | 2.68E−05 | 2.68E−05 | 2.68E−05 | 2.68E−05 |
| LOVO | GI50 | 6.37E−06 | 6.88E−06 | 8.22E−08 | 4.81E−06 | 7.14E−07 | 2.68E−05 |
| | TGI | 1.21E−05 | 1.21E−05 | 1.35E−06 | 1.26E−05 | 7.01E−06 | 2.68E−05 |
| | LC50 | 1.21E−05 | 1.21E−05 | 1.77E−05 | 2.68E−05 | 2.68E−05 | 2.68E−05 |
| LOVO-DOX | GI50 | 1.21E−05 | 1.21E−05 | 1.52E−07 | 9.34E−06 | 8.46E−06 | 2.68E−05 |
| | TGI | 1.21E−05 | 1.21E−05 | 1.36E−06 | 2.68E−05 | 6.18E−06 | 2.68E−05 |
| | LC50 | 1.21E−05 | 1.21E−05 | 2.68E−05 | 2.68E−05 | 2.68E−05 | 2.68E−05 |
| HELA | GI50 | 1.21E−05 | 1.21E−05 | 7.28E−08 | 8.73E−06 | 6.20E−07 | 2.68E−05 |
| | TGI | 1.21E−05 | 1.21E−05 | 5.50E−07 | 2.68E−05 | 4.78E−06 | 2.68E−05 |
| | LC50 | 1.21E−05 | 1.21E−05 | 7.14E−06 | 2.68E−05 | 2.68E−05 | 2.68E−05 |
| HELA-APL | GI50 | 1.21E−05 | 1.21E−05 | 7.33E−08 | 5.18E−06 | 5.93E−07 | 2.68E−05 |
| | TGI | 1.21E−05 | 1.21E−05 | 9.83E−07 | 2.68E−05 | 8.67E−06 | 2.68E−05 |
| | LC50 | 1.21E−05 | 1.21E−05 | 1.47E−05 | 2.68E−05 | 2.68E−05 | 2.68E−05 |

| | | 46 | 43 | 44 | 45 | 47 | 1 |
|---|---|---|---|---|---|---|---|
| DU-145 | GI50 | 9.65E−06 | 4.99E−06 | 4.99E−06 | 1.63E−05 | 8.15E−08 | 3.66E−06 |
| | TGI | 1.89E−05 | 9.66E−06 | 1.04E−05 | 1.63E−05 | 5.31E−07 | 1.02E−05 |
| | LC50 | 1.89E−05 | 1.87E−05 | 1.75E−05 | 1.63E−05 | 2.41E−05 | 2.52E−05 |
| LN-caP | GI50 | 5.24E−06 | 3.78E−06 | 3.77E−06 | 8.34E−06 | 8.13E−08 | 1.45E−06 |
| | TGI | 9.06E−06 | 7.62E−06 | 7.88E−06 | 1.63E−05 | 5.36E−07 | 6.31E−06 |
| | LC50 | 1.56E−05 | 1.54E−05 | 1.66E−05 | 1.63E−05 | 8.88E−06 | 2.52E−05 |
| IGROV | GI50 | 7.74E−06 | 4.94E−06 | 4.13E−06 | 1.63E−05 | 6.39E−08 | 1.63E−06 |
| | TGI | 1.89E−05 | 9.99E−06 | 7.67E−06 | 1.63E−05 | 5.28E−07 | 5.67E−06 |
| | LC50 | 1.89E−05 | 1.89E−05 | 1.42E−05 | 1.63E−05 | 2.41E−05 | 1.76E−05 |
| IGROV-ET | GI50 | 7.39E−06 | 4.52E−06 | 4.15E−06 | 1.58E−05 | 1.52E−07 | 3.10E−06 |
| | TGI | 1.89E−05 | 8.96E−06 | 8.09E−06 | 1.63E−05 | 1.08E−06 | 8.58E−06 |
| | LC50 | 1.89E−05 | 1.78E−05 | 1.58E−05 | 1.63E−05 | 2.41E−05 | 2.37E−05 |
| SK-BR-3 | GI50 | — | — | — | — | 2.31E−08 | 4.69E−07 |
| | TGI | — | — | — | — | 1.18E−07 | 1.11E−05 |
| | LC50 | — | — | — | — | 2.30E−06 | 3.43E−06 |
| MEL-28 | GI50 | 9.89E−06 | 3.90E−06 | 3.84E−06 | 1.63E−05 | 8.20E−08 | 2.72E−06 |
| | TGI | 1.89E−05 | 7.24E−06 | 6.96E−06 | 1.63E−05 | 9.84E−07 | 6.10E−06 |
| | LC50 | 1.89E−05 | 1.34E−05 | 1.26E−05 | 1.63E−05 | 1.29E−05 | 1.36E−05 |
| A-549 | GI50 | 1.34E−06 | 4.44E−06 | 4.01E−06 | 1.63E−05 | 1.51E−07 | 1.10E−06 |
| | TGI | 1.89E−05 | 8.49E−06 | 7.87E−06 | 1.63E−05 | 1.12E−06 | 5.04E−06 |
| | LC50 | 1.89E−05 | 1.62E−05 | 1.54E−05 | 1.63E−05 | 2.32E−05 | 2.35E−05 |
| K-562 | GI50 | 1.20E−06 | 3.59E−06 | 6.10E−06 | 1.63E−05 | 2.94E−07 | 1.99E−06 |
| | TGI | 1.89E−05 | 7.72E−06 | 1.14E−05 | 1.63E−05 | 9.99E−07 | 7.36E−06 |
| | LC50 | 1.89E−05 | 1.65E−05 | 1.75E−05 | 1.63E−05 | 1.18E−05 | 2.46E−05 |
| PANC-1 | GI50 | 7.38E−06 | 3.73E−06 | 3.73E−06 | 8.24E−06 | 9.05E−08 | 3.33E−06 |
| | TGI | 1.89E−05 | 7.02E−06 | 7.20E−06 | 1.63E−05 | 2.38E−06 | 8.40E−06 |
| | LC50 | 1.89E−05 | 1.32E−05 | 1.38E−05 | 1.63E−05 | 1.95E−05 | 2.13E−05 |
| HT-29 | GI50 | 1.50E−06 | 4.24E−06 | 6.22E−06 | 1.63E−05 | 1.06E−07 | 1.67E−06 |
| | TGI | 1.89E−05 | 8.28E−06 | 1.75E−05 | 1.63E−05 | 3.11E−06 | 5.37E−06 |
| | LC50 | 1.89E−05 | 1.62E−05 | 1.70E−05 | 1.63E−05 | 2.41E−05 | 1.34E−05 |
| LOVO | GI50 | 4.37E−06 | 4.03E−06 | 4.05E−06 | 8.26E−06 | 4.03E−08 | 1.62E−06 |
| | TGI | 1.00E−05 | 9.06E−06 | 8.99E−06 | 1.63E−05 | 3.74E−07 | 4.87E−06 |
| | LC50 | 1.89E−05 | 1.89E−05 | 1.75E−05 | 1.63E−05 | 1.77E−05 | 1.26E−05 |

TABLE 1-continued

| | | Activity data (Molar) | | | | | |
|---|---|---|---|---|---|---|---|
| LOVO-DOX | GI50 | 6.15E−06 | 3.31E−06 | 4.27E−06 | 1.05E−05 | 2.16E−07 | 3.13E−06 |
| | TGI | 1.89E−05 | 7.21E−06 | 8.90E−06 | 1.63E−05 | 2.41E−05 | 8.10E−06 |
| | LC50 | 1.89E−05 | 1.57E−05 | 1.75E−05 | 1.63E−05 | 2.41E−05 | 2.11E−05 |
| HELA | GI50 | 8.81E−06 | 4.37E−06 | 3.91E−06 | 1.63E−05 | 7.17E−08 | 1.99E−06 |
| | TGI | 1.89E−05 | 8.47E−06 | 7.59E−06 | 1.63E−05 | 4.34E−07 | 6.66E−06 |
| | LC50 | 1.89E−05 | 1.64E−05 | 1.47E−05 | 1.63E−05 | 1.35E−05 | 2.05E−05 |
| HELA-APL | GI50 | 1.01E−05 | 4.27E−06 | 3.77E−06 | 1.63E−05 | 7.96E−08 | 1.72E−06 |
| | TGI | 1.89E−05 | 9.34E−06 | 9.83E−06 | 1.63E−05 | 5.91E−07 | 6.23E−06 |
| | LC50 | 1.89E−05 | 1.89E−05 | 1.75E−05 | 1.63E−05 | 2.41E−05 | 2.20E−03 |

The invention claimed is:

1. A compound of the general formula I, a pharmaceutically acceptable salt, or a stereoisomer thereof

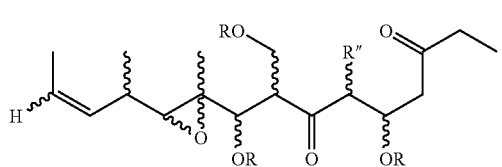

wherein each R is independently selected from the group consisting of H, SiR'$_3$, SOR', SO$_2$R', C(=O)R', C(=O)OR', C(=O)NHR', substituted or unsubstituted alkyl, substituted or unsubstituted alkenyl, substituted or unsubstituted alkynyl, aryl, heteroaryl or aralkyl;

the group R' is independently selected from substituted or unsubstituted alkyl, substituted or unsubstituted alkenyl, substituted or unsubstituted alkynyl, aminoalkyl, aryl, aralkyl and heterocyclic groups; and the group R" is selected from the group consisting of H, OH, OR', OCOR', SH, SR', SOR', SO$_2$R', NO$_2$, NH$_2$, NHR', N(R')$_2$, NHCOR', N(COR')$_2$, NHSO$_2$R', CN, halogen, C(=O)H, C(=O)R', CO$_2$H, CO$_2$R', CH$_2$OR, substituted or unsubstituted alkyl, substituted or unsubstituted haloalkyl, substituted or unsubstituted alkenyl, substituted or unsubstituted alkylidene, substituted or unsubstituted alkynyl, substituted, or unsubstituted aryl, substituted or unsubstituted aralkyl and substituted or unsubstituted heteroaromatic;

with the proviso that the compound is not a compound of formula

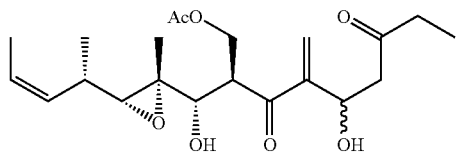

2. A compound according to claim 1, with the following stereochemistry

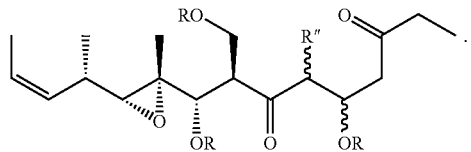

3. A compound according to claim 1, wherein R" is CH$_2$OH

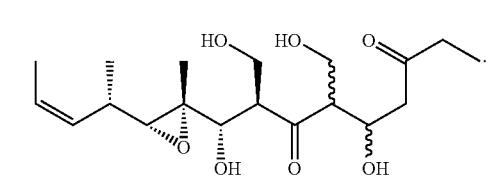

which may exist as one of the two isomeric forms at each isomeric center.

4. A compound according to claim 3, with the following stereochemistry

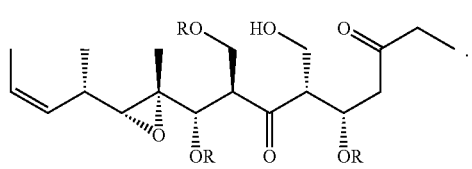

5. A compound according to claim 4, with the following stereochemistry

6. A compound according to claim 4, with the following stereochemistry

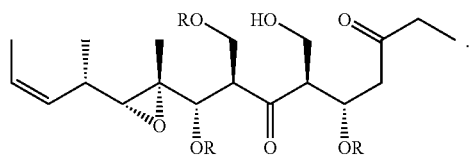

7. A compound according to claim 1 or 2, wherein R" is a substituted or unsubstituted alkylidene.

8. A compound according to claim 3, wherein at least one R is C(=O)R'.

9. A compound according to claim 8, which is of formula

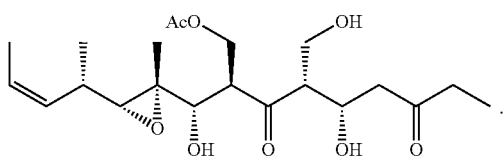

10. A compound according to claim 1, wherein at least one R is selected from the group consisting of SiR'$_3$, SOR', SO$_2$R', C(=O)R', C(=O)OR', C(=O)NHR', substituted or unsubstituted alkyl, substituted or unsubstituted alkenyl, substituted or unsubstituted alkynyl, aryl, heteroaryl or aralkyl.

11. A compound according to claim 10, wherein at least one R is selected from the group consisting of SiR'$_3$, C(=O)R', and substituted alkyl.

12. A compound according to claim 1, which is of formula

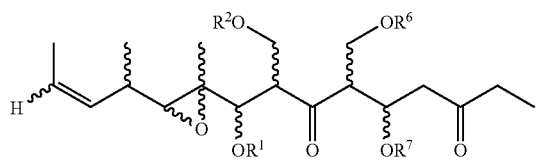

where R$^1$, R$^2$, R$^6$ and R$^7$ are each independently selected from the group consisting of SiR'$_3$, C(=O)R', and substituted alkyl.

13. A compound according to claim 12, which is of formula

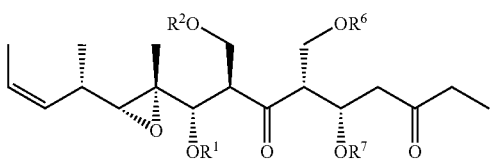

where R$^1$, R$^2$, R$^6$ and R$^7$ are as defined in claim 12.

14. A compound according to claim 12, which is of formula

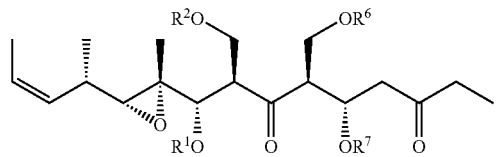

where R$^1$, R$^2$, R$^6$ and R$^7$ are as defined in claim 12.

15. A compound according to claim 12, wherein R$^1$, R$^2$, R$^6$ and R$^7$ are the same.

16. A compound according to claim 12, wherein R$^1$, R$^2$, R$^6$ and R$^7$ are chosen from TBS (tBuMe$_2$Si—), TBDPS (tBuPh$_2$Si—), TES (Et$_3$Si—), MOM (CH$_3$OCH$_2$—), MEM (CH$_3$OCH$_2$CH$_2$OCH$_2$—), SEM ((CH$_3$)$_3$SiCH$_2$CH$_2$OCH$_2$—) and Ac—(CH$_3$CO—).

17. A compound according to claim 16, wherein R$^1$, R$^2$, R$^6$ and R$^7$ are chosen from TBS (tBuMe$_2$Si—) and TBDPS (tBuPh$_2$Si—).

18. A compound according to claim 1, which is of formula

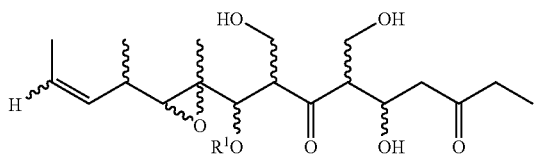

where R$^1$ is selected from the group consisting of SiR'$_3$, C(=O)R', and substituted alkyl.

19. A compound according to claim 18, which is of formula:

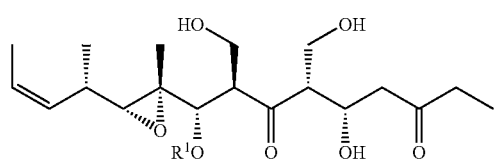

where R$^1$ is as defined in claim 18.

20. A compound according to claim 18, which is of formula:

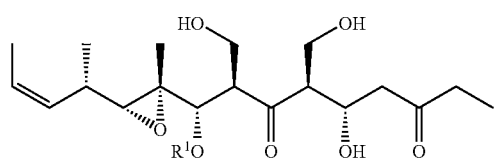

where R$^1$ is as defined in claim 18.

21. A compound according to claim 18, wherein R$^1$ is TBS (tBuMe$_2$Si—).

22. A pharmaceutical composition comprising a compound according to claim 1, and a pharmaceutically acceptable carrier.

23. A method of preparing a medicament for treating a tumor comprising combining a compound according to claim 1 with a pharmaceutically acceptable carrier.

24. A method of treating a tumor which comprises administering an effective amount of a compound according to claim 1.

25. A process for synthesis of a compound according to claim 3
which comprises removing a protecting group from an intermediate compound of formula:

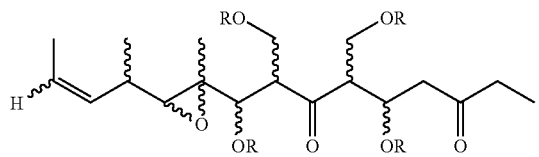

wherein each R is independently selected from the group consisting of H, SiR'$_3$, SOR', SO$_2$R', C(=O)R', C(=O)OR', C(=O)NHR', substituted or unsubstituted alkyl, substituted or unsubstituted alkenyl, substituted or unsubstituted alkynyl, aryl, heteroaryl or aralkyl, and wherein for at least one R in the product compound of claim 3 that is hydrogen, the corresponding R in the intermediate compound above is a protecting group; and wherein the group R' is as defined in claim 3, and wherein each said protecting group is independently selected from the group consisting of SiR'$_3$, C(=O)R', and substituted alkyl.

26. A process according to claim 25, wherein more than one R in the intermediate compound is a protecting group as defined in claim 25.

27. A process according to claim 25, which comprises replacing at least one moiety with hydrogen in a compound of formula:

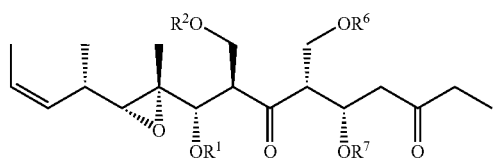

where said moiety to be replaced is selected from $R^1$, $R^2$, $R^6$, and $R^7$, and where at least one $R^1$, $R^2$, $R^6$ and $R^7$ is selected from the group consisting of SiR'$_3$, C(=O)R', and substituted alkyl, and the remaining moieties are defined as R according to claim 25.

28. A process according to claim 25, which comprises replacing at least one moiety with hydrogen in a compound of formula:

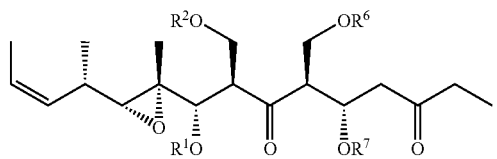

where said moiety to be replaced is selected from $R^1$, $R^2$, $R^6$, and $R^7$, and where at least one $R^1$, $R^2$, $R^6$ and $R^7$ is selected from the group consisting of SiR'$_3$, C(=O)R', and substituted alkyl, and the remaining moieties are defined as R according to claim 25.

29. A process according to any of claims 25 to 28, wherein $R^1$, $R^2$, $R^6$ and $R^7$ are the same and are each replaced with hydrogen.

30. A process according to claim 25, which comprises replacing $R^1$ with hydrogen in a compound of formula:

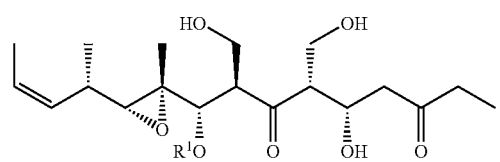

where $R^1$ is selected from the group consisting of SiR'$_3$, C(=O)R', and substituted alkyl.

31. A process according to claim 25, which comprises replacing $R^1$ with hydrogen in a compound of formula:

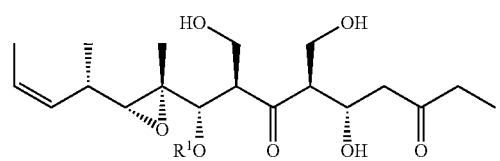

where $R^1$ is selected from the group consisting of SiR'$_3$, C(=O)R', and substituted alkyl.

32. A process for synthesis of a compound according to claim 1 which comprises derivatisation of a compound of formula:

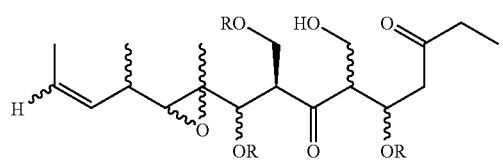

which may exist as a mixture of the ketone isomer and the hemiketal isomer, or as one of the two isomeric forms; and wherein R is as defined in claim 1.

33. A process according to claim 32 comprising the steps of Scheme 1 from compound 6

Scheme 1
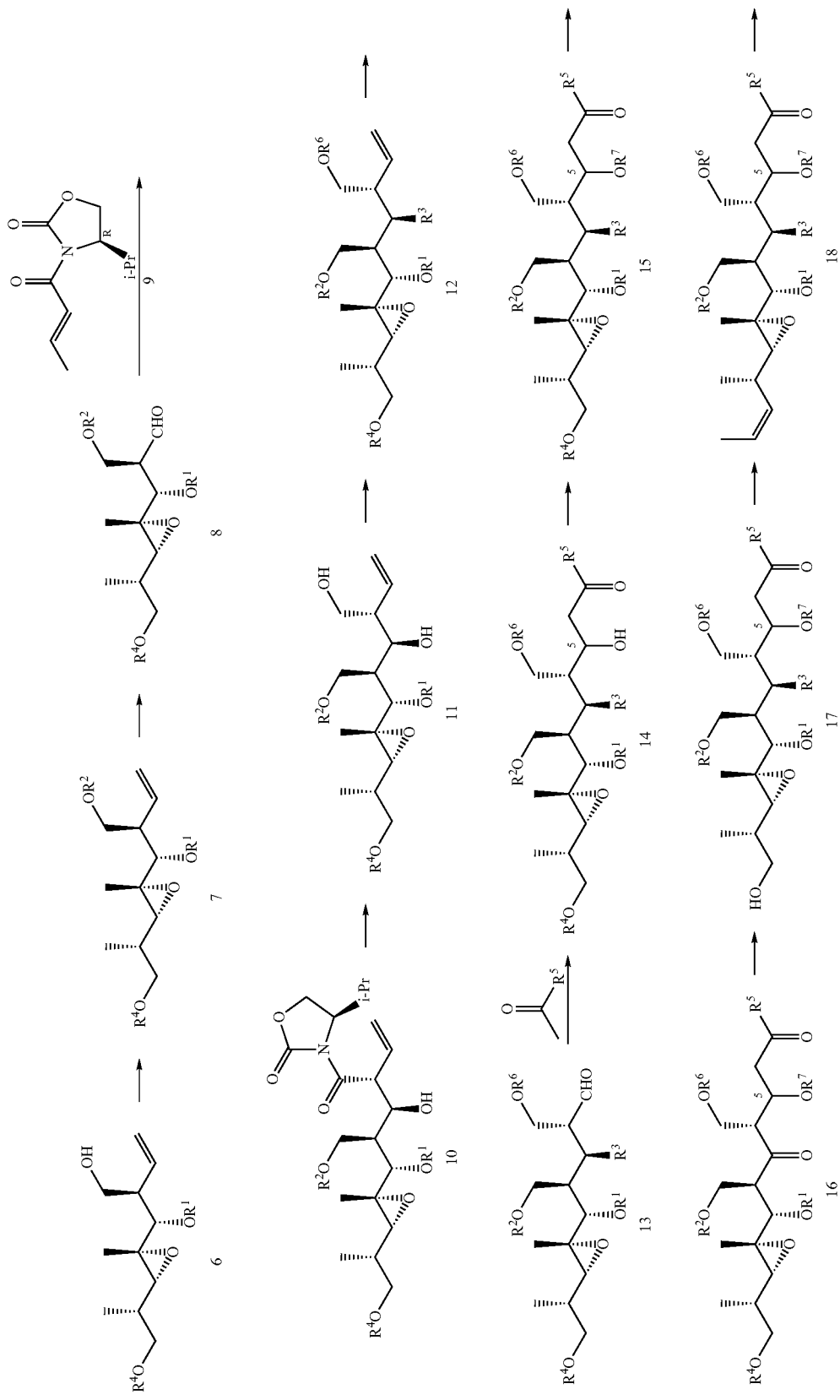

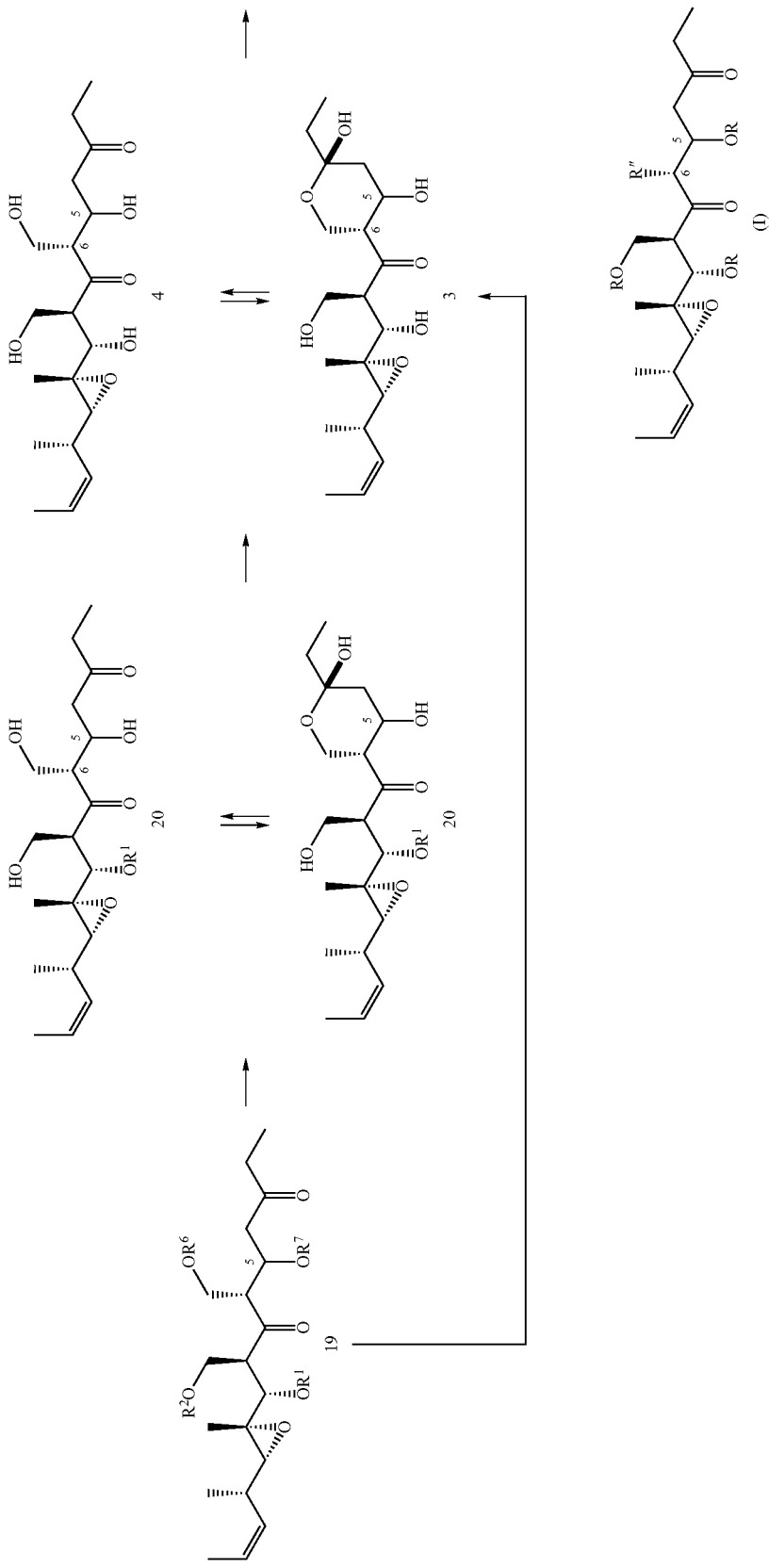

where $R^1$, $R^2$, $R^4$, $R^6$ and $R^7$ are independently defined as R as defined in claim 32.

34. A process according to claim 32 comprising the steps of Scheme 2 from compound 8

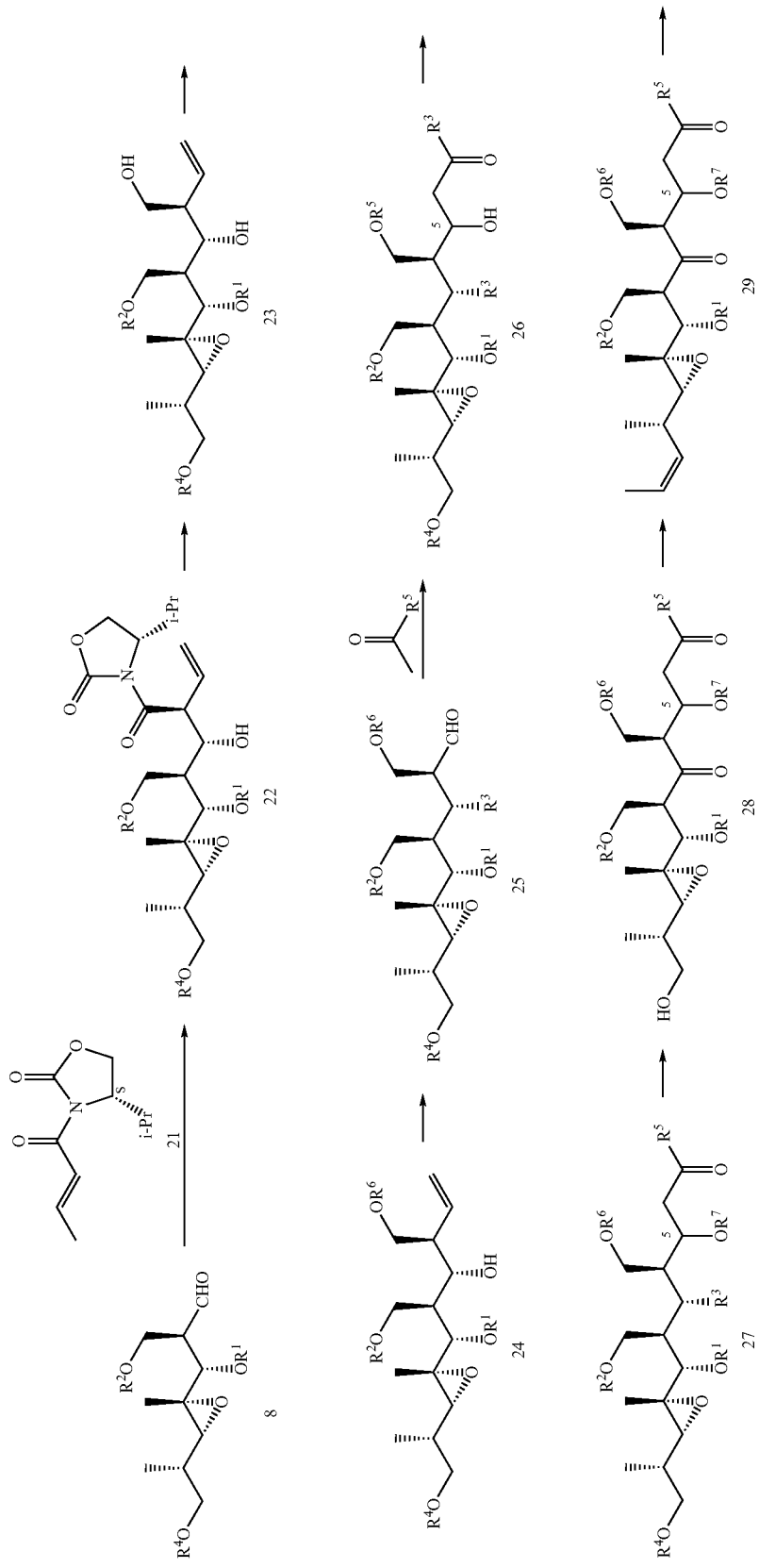
Scheme 2

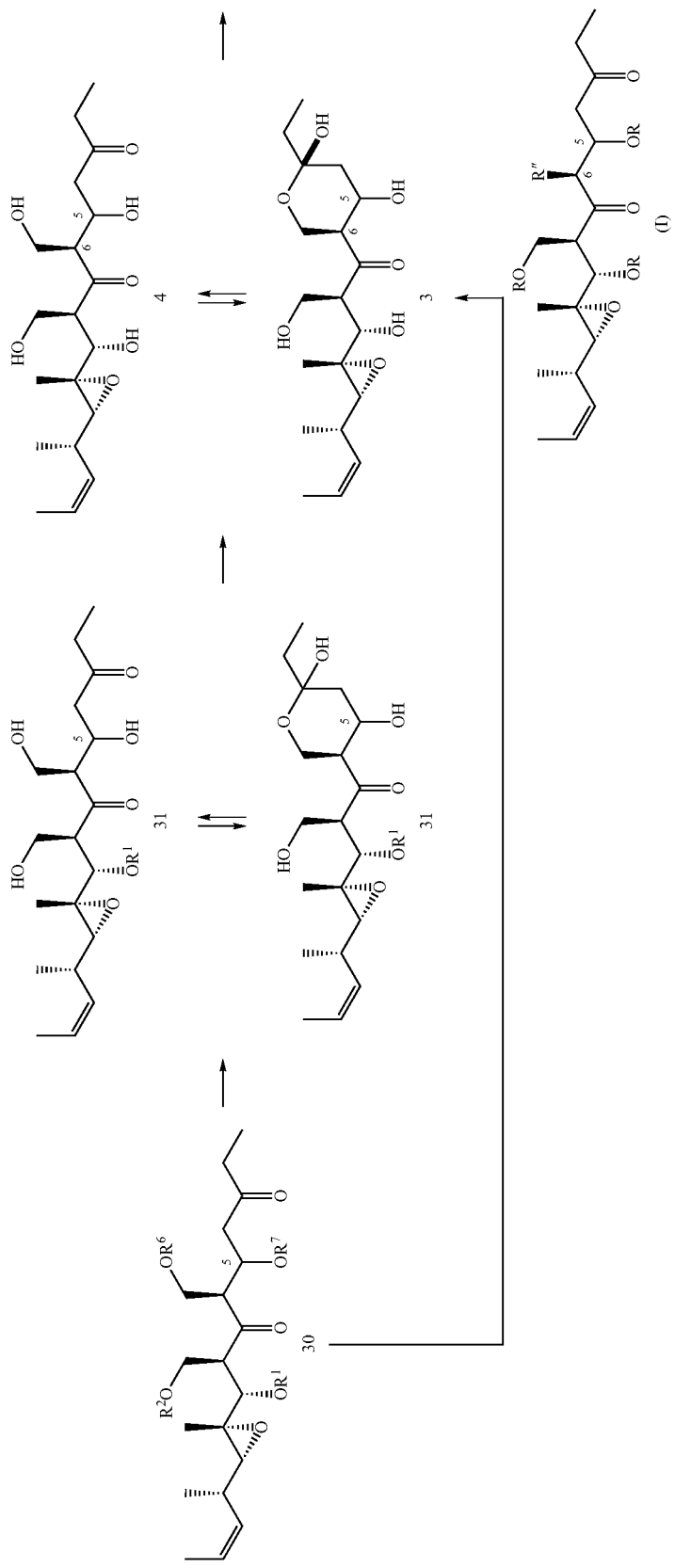

where $R^1$, $R^2$, $R^4$, $R^6$ and $R^7$ are independently defined as R as defined in claim 32.

* * * * *

UNITED STATES PATENT AND TRADEMARK OFFICE
CERTIFICATE OF CORRECTION

| | | |
|---|---|---|
| PATENT NO. | : 7,521,478 B2 | Page 1 of 1 |
| APPLICATION NO. | : 10/523172 | |
| DATED | : April 21, 2009 | |
| INVENTOR(S) | : Losada et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 329 days Delete the phrase "by 329 days" and insert -- by 775 days --

Signed and Sealed this

Thirteenth Day of April, 2010

David J. Kappos
*Director of the United States Patent and Trademark Office*